United States Patent
Detlefsen et al.

(10) Patent No.: US 12,082,848 B2
(45) Date of Patent: Sep. 10, 2024

(54) BONE ANCHORS WITH CORD RETENTION FEATURES

(71) Applicant: OrthoPediatric Corp., Warsaw, IN (US)

(72) Inventors: Rick Detlefsen, Warsaw, IN (US); Matthew Prygoski, North Liberty, IN (US); David W. Daniels, Winona Lake, IN (US); Evangelos Tozakoglou, Fort Wayne, IN (US)

(73) Assignee: OrthoPediatrics Corp., Warsaw, IN (US)

(*) Notice: Subject to any disclaimer, the term of this patent is extended or adjusted under 35 U.S.C. 154(b) by 1053 days.

(21) Appl. No.: 16/803,198

(22) Filed: Feb. 27, 2020

(65) Prior Publication Data

US 2020/0390472 A1    Dec. 17, 2020

Related U.S. Application Data

(60) Provisional application No. 62/882,238, filed on Aug. 2, 2019, provisional application No. 62/811,318, filed on Feb. 27, 2019.

(51) Int. Cl.
*A61B 17/68* (2006.01)
*A61B 17/86* (2006.01)

(52) U.S. Cl.
CPC ........ *A61B 17/685* (2013.01); *A61B 17/8605* (2013.01)

(58) Field of Classification Search
CPC .............. A61B 17/7019; A61B 17/702; A61B 17/7022; A61B 17/7026; A61B 17/7029; A61B 17/7031; A61B 17/7049; A61B 17/7053; A61B 17/7044; A61B 17/7043; A61B 17/7058; A61B 17/7007; A61B 17/0642

See application file for complete search history.

(56) References Cited

U.S. PATENT DOCUMENTS

| | | | |
|---|---|---|---|
| 5,690,629 A | 11/1997 | Asher et al. | |
| 5,863,293 A | 1/1999 | Richelsoph | |
| 5,899,905 A | 5/1999 | Errico et al. | |
| 5,925,047 A * | 7/1999 | Errico | A61B 17/7032 606/65 |
| 5,947,969 A * | 9/1999 | Errico | A61B 17/7032 606/308 |
| 6,488,683 B2 * | 12/2002 | Lieberman | A61B 17/701 606/279 |
| 7,601,166 B2 * | 10/2009 | Biedermann | A61B 17/701 606/255 |
| 7,909,826 B2 * | 3/2011 | Serhan | A61B 17/701 606/75 |
| 8,123,749 B2 | 2/2012 | Serhan et al. | |
| 8,133,262 B2 | 3/2012 | Whipple | |
| 8,157,843 B2 * | 4/2012 | Biedermann | A61B 17/7031 606/255 |
| 8,273,086 B2 | 9/2012 | Serhan et al. | |

(Continued)

OTHER PUBLICATIONS

DePuy Synthes Spine, Expedium Spin System Product Binder, 5.5 System, 2012, 24 pages.

*Primary Examiner* — Lynnsy M Summitt
(74) *Attorney, Agent, or Firm* — Gerald W. Roberts; John V. Daniluck; Dentons Bingham Greenebaum LLP

(57) ABSTRACT

Methods and apparatus for coupling two or more bones together with a flexible connector.

7 Claims, 38 Drawing Sheets

(56) References Cited

U.S. PATENT DOCUMENTS

| | | | | |
|---|---|---|---|---|
| 8,277,485 B2* | 10/2012 | Krishna | A61B 17/8685 | |
| | | | 606/246 | |
| 8,277,494 B2* | 10/2012 | Biedermann | A61B 17/7032 | |
| | | | 606/279 | |
| 8,361,130 B2* | 1/2013 | Daly | A61B 17/7032 | |
| | | | 606/313 | |
| 8,568,458 B2* | 10/2013 | Matthis | A61B 17/7037 | |
| | | | 606/264 | |
| 8,690,924 B2* | 4/2014 | Chin | A61B 17/7044 | |
| | | | 606/264 | |
| 8,740,945 B2* | 6/2014 | Hestad | A61B 17/7037 | |
| | | | 606/272 | |
| 8,795,336 B2* | 8/2014 | Biedermann | A61B 17/702 | |
| | | | 606/267 | |
| 8,814,909 B2 | 8/2014 | Fanger et al. | | |
| 8,845,700 B2 | 9/2014 | Kwak et al. | | |
| 8,888,818 B2 | 11/2014 | Serhan et al. | | |
| 9,095,379 B2 | 8/2015 | Chao et al. | | |
| 9,144,437 B2* | 9/2015 | Matthis | A61B 17/7031 | |
| 9,265,548 B2 | 2/2016 | Jones et al. | | |
| 9,326,796 B2 | 5/2016 | Harvey et al. | | |
| 9,439,681 B2 | 9/2016 | Keyer et al. | | |
| 9,492,165 B2 | 11/2016 | Serhan et al. | | |
| 9,622,789 B2* | 4/2017 | Carbone | A61B 17/7044 | |
| 9,820,782 B2 | 11/2017 | Daniels | | |
| 9,848,915 B2* | 12/2017 | Beger | A61B 17/7032 | |
| 9,872,711 B2* | 1/2018 | Hynes | A61B 17/7032 | |
| 9,895,169 B2* | 2/2018 | Faulhaber | A61B 17/7035 | |
| 9,980,752 B2* | 5/2018 | Smith | A61B 17/7035 | |
| 10,603,084 B1* | 3/2020 | Sanders | A61B 17/8695 | |
| 2008/0319490 A1* | 12/2008 | Jackson | A61B 17/7008 | |
| | | | 606/301 | |
| 2010/0094358 A1* | 4/2010 | Moore | A61B 17/809 | |
| | | | 606/319 | |
| 2012/0283779 A1* | 11/2012 | Biedermann | A61B 17/7037 | |
| | | | 606/328 | |
| 2013/0079833 A1* | 3/2013 | Biedermann | A61B 17/7019 | |
| | | | 606/308 | |
| 2013/0338715 A1 | 12/2013 | Daly et al. | | |
| 2015/0142058 A1* | 5/2015 | Hodgson | A61B 17/7053 | |
| | | | 606/255 | |
| 2017/0027616 A1 | 2/2017 | Serhan et al. | | |
| 2018/0092670 A1* | 4/2018 | Crossgrove | A61B 17/7044 | |
| 2019/0069932 A1* | 3/2019 | Chaput | A61B 17/701 | |
| 2022/0226023 A1* | 7/2022 | Mast | A61B 17/7032 | |

\* cited by examiner

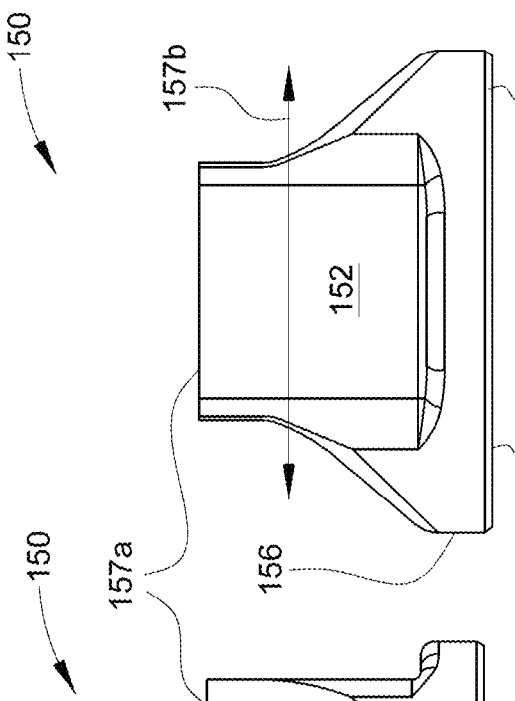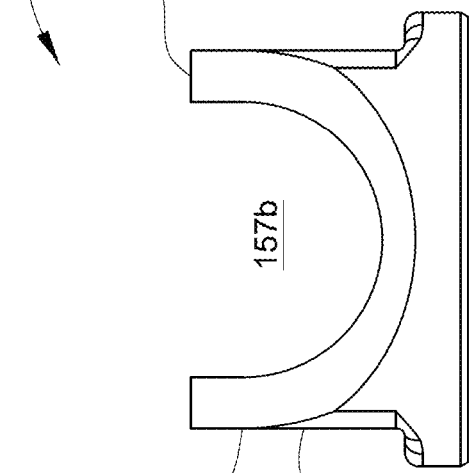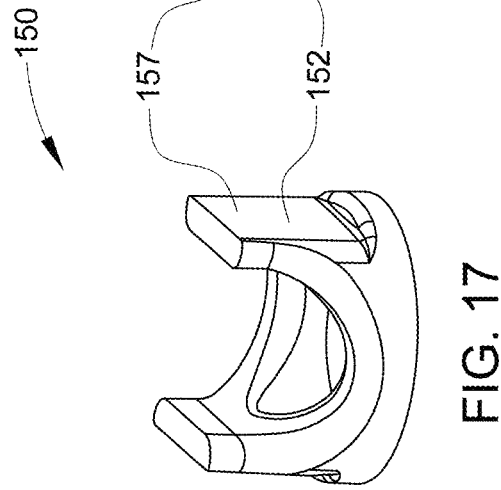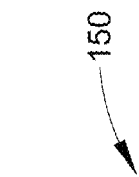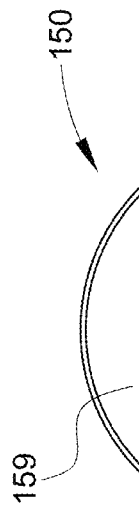

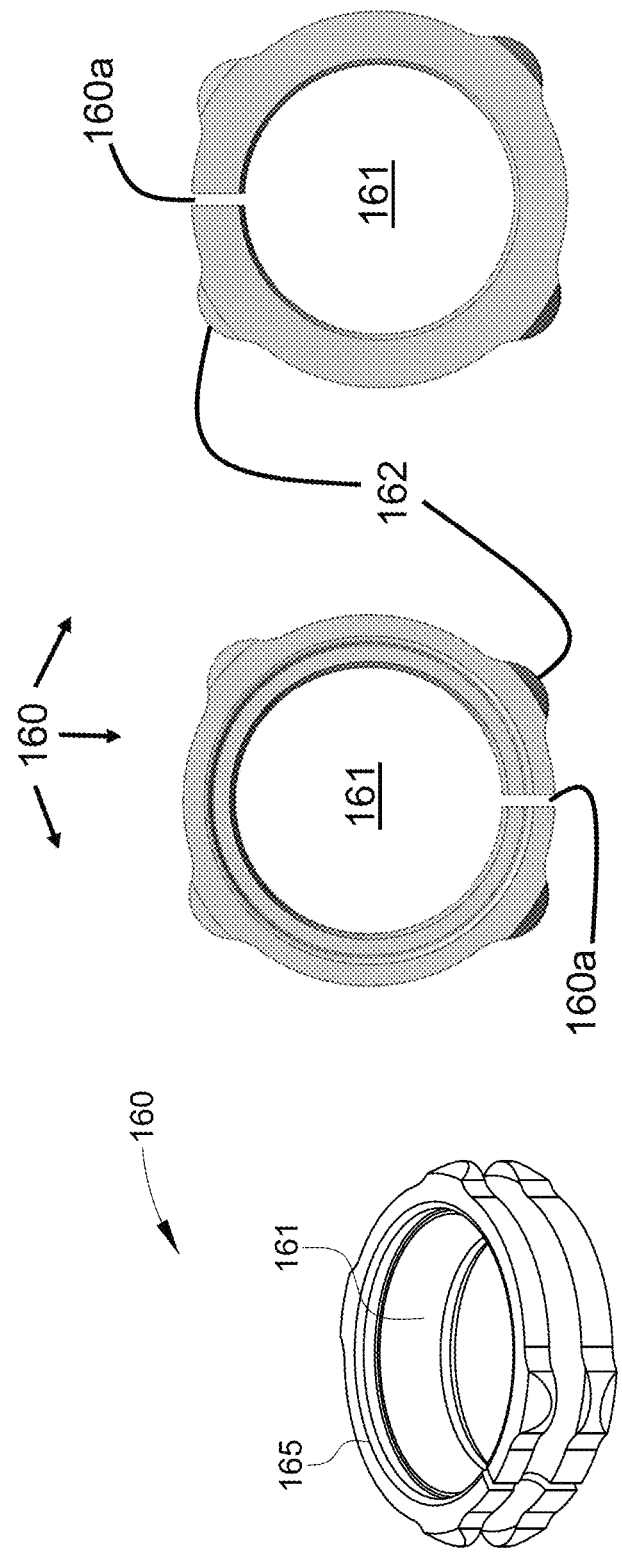
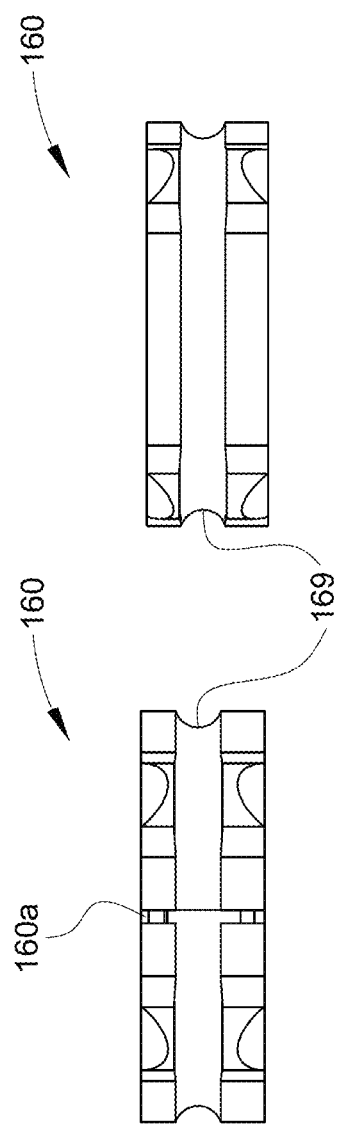

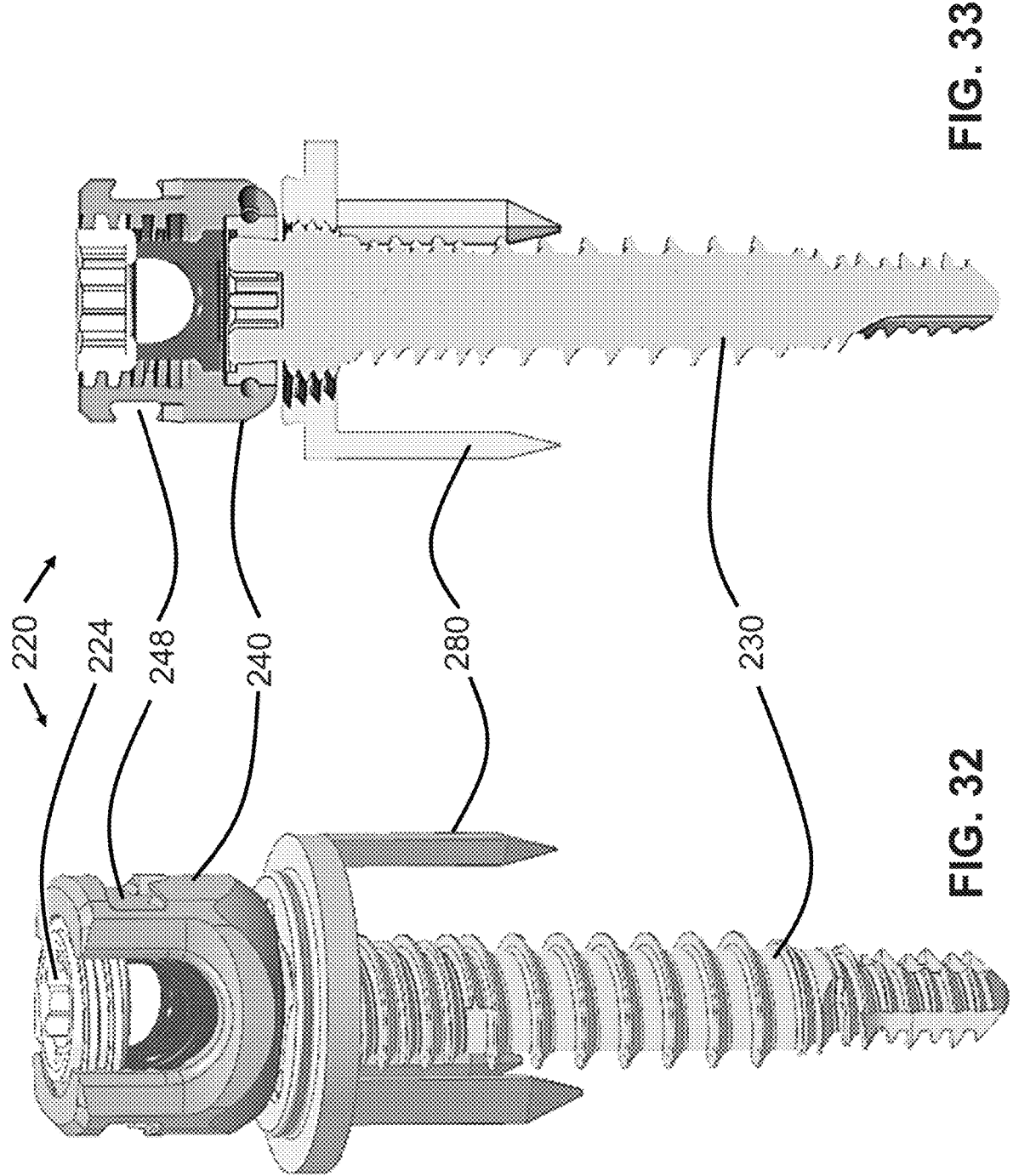

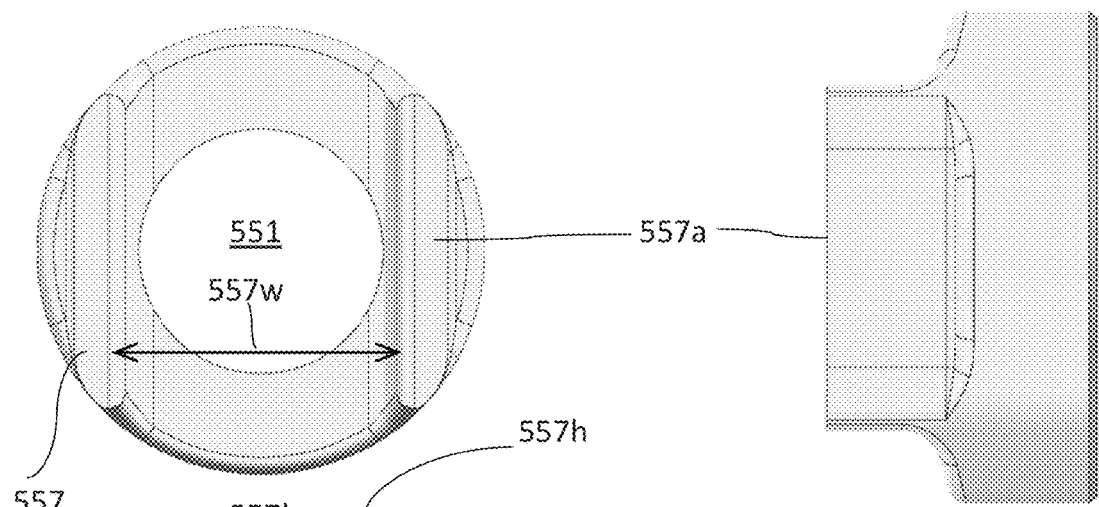
FIG. 45A
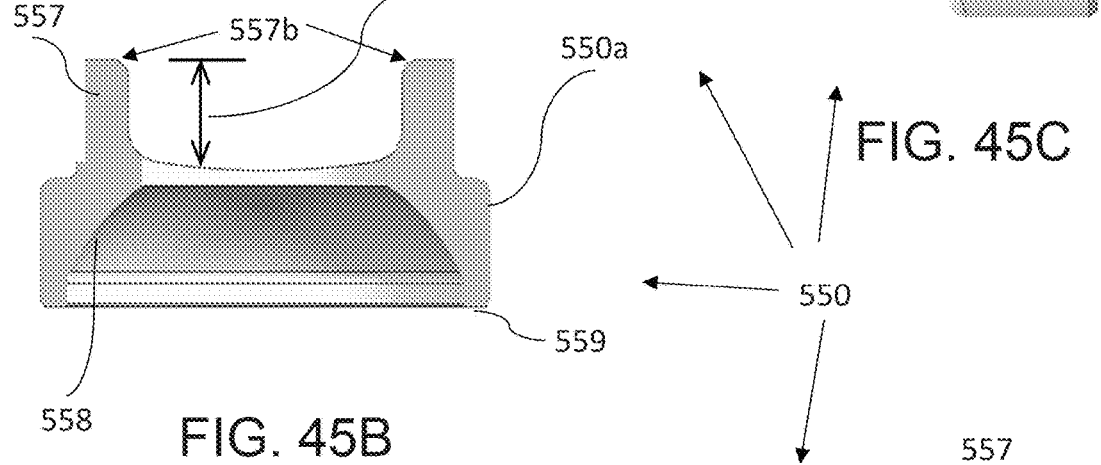
FIG. 45B
FIG. 45C
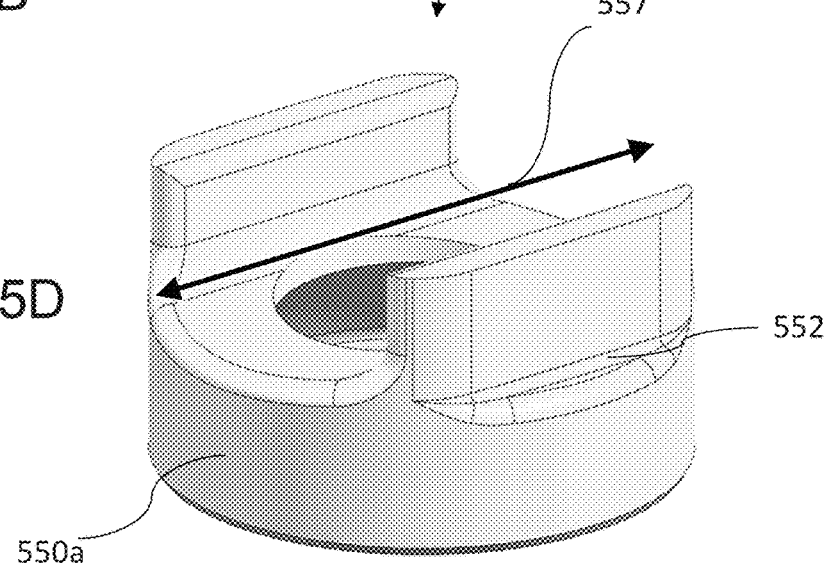
FIG. 45D

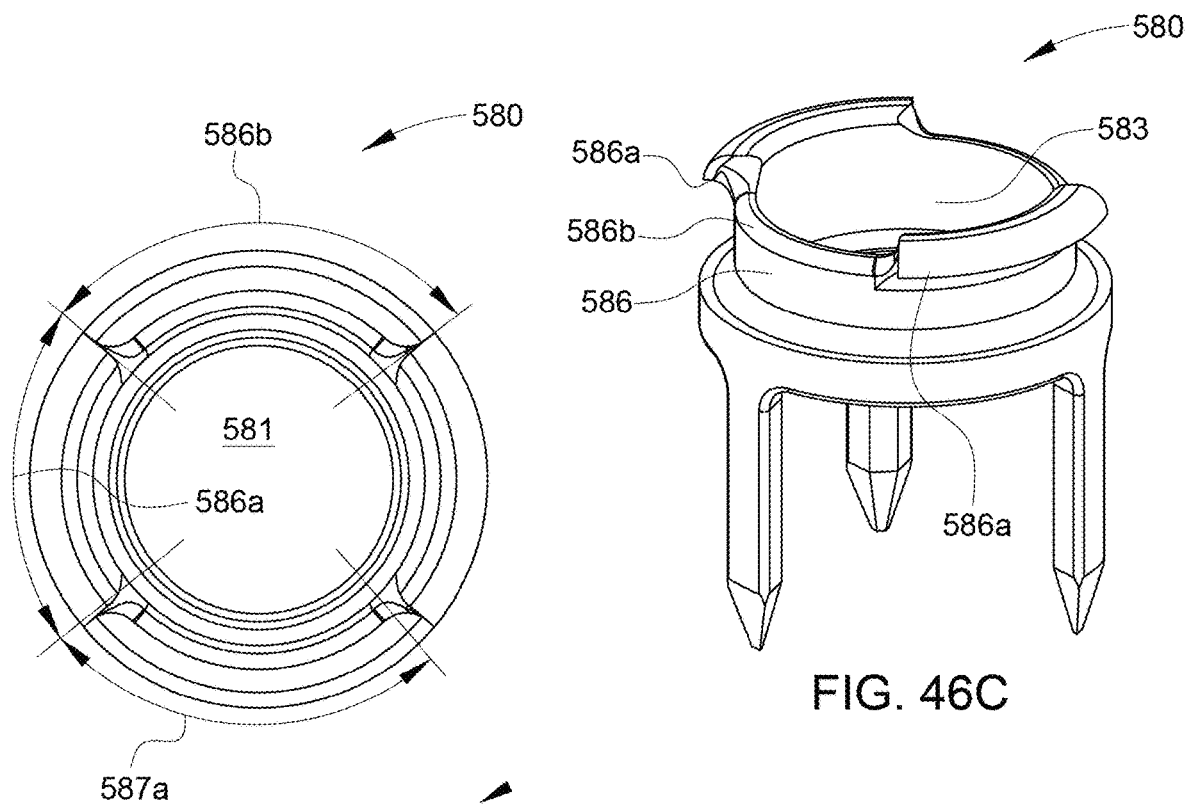

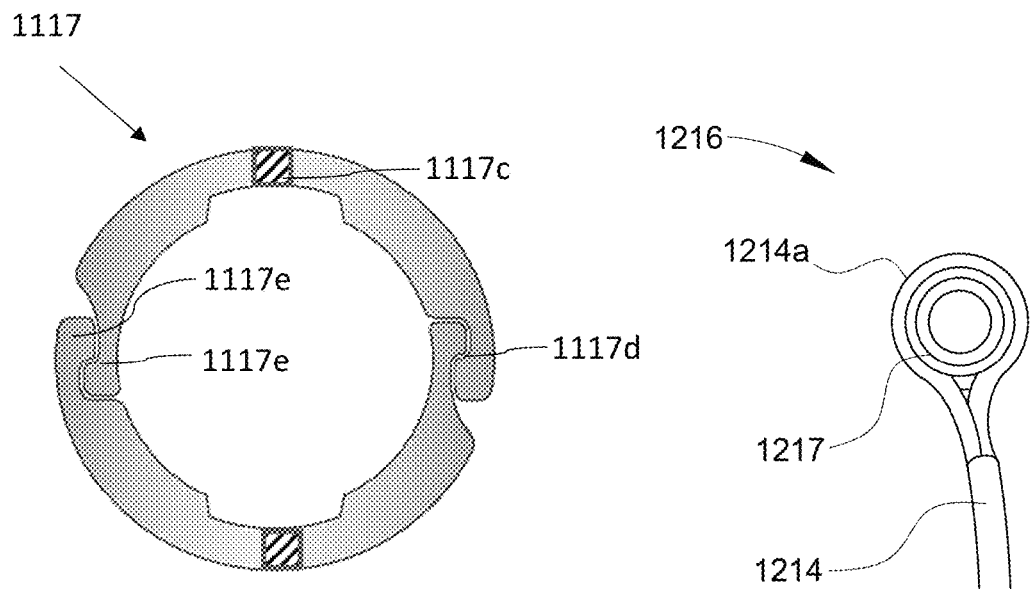
FIG. 52D
FIG. 52E
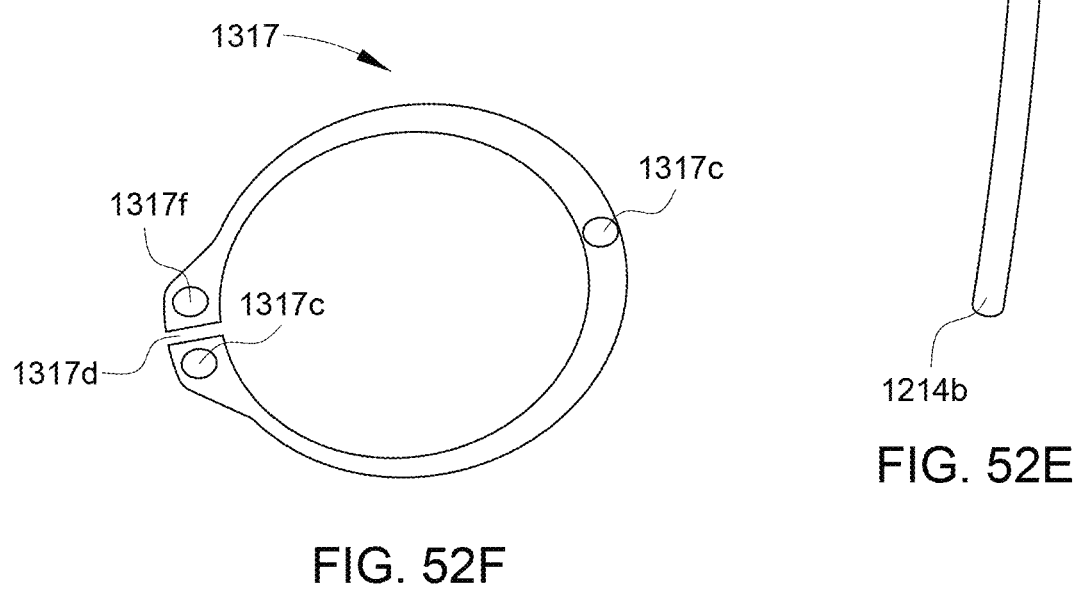
FIG. 52F

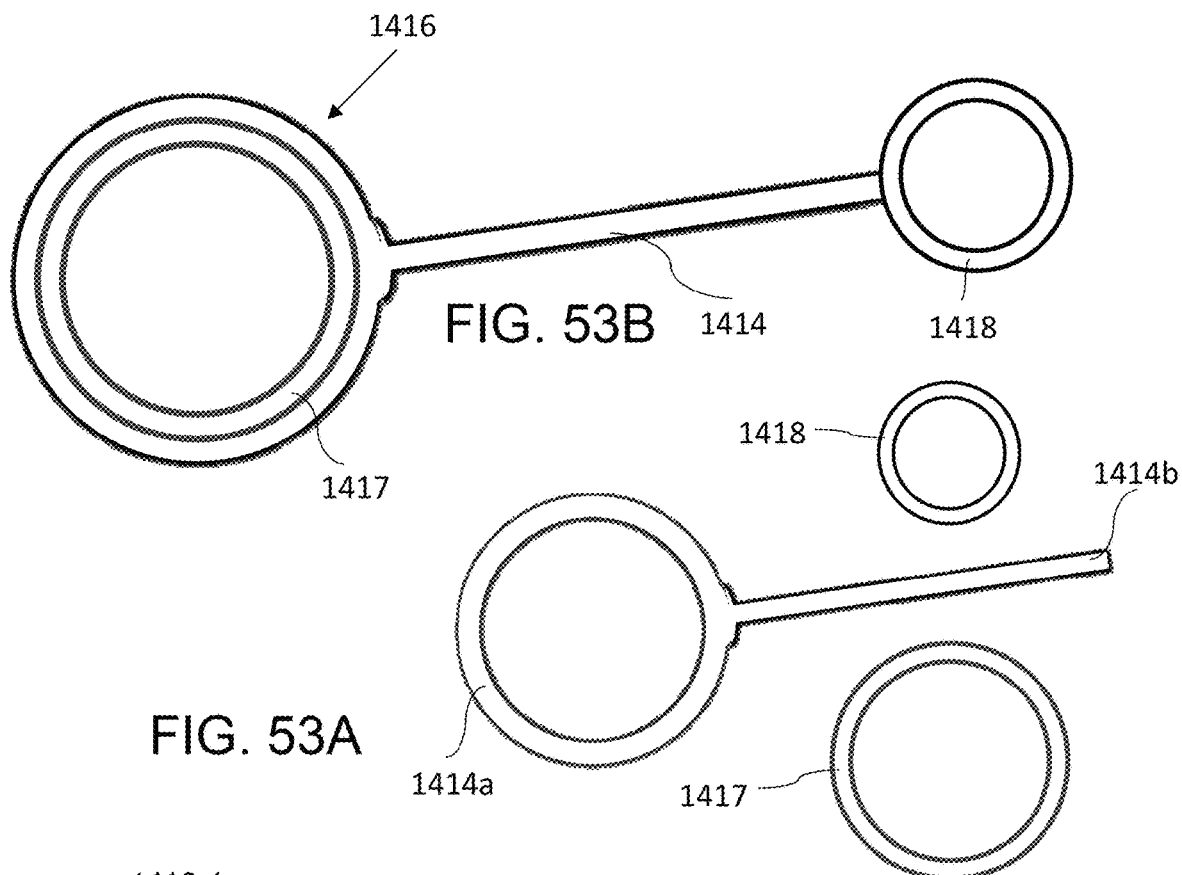
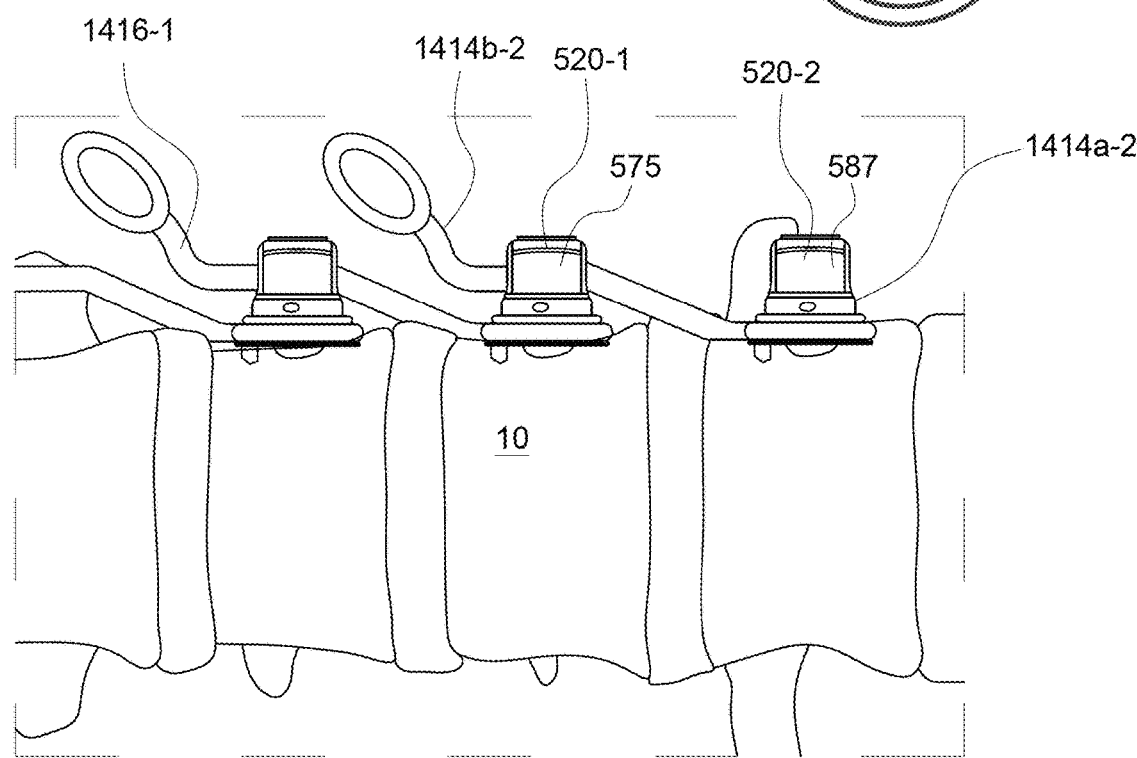

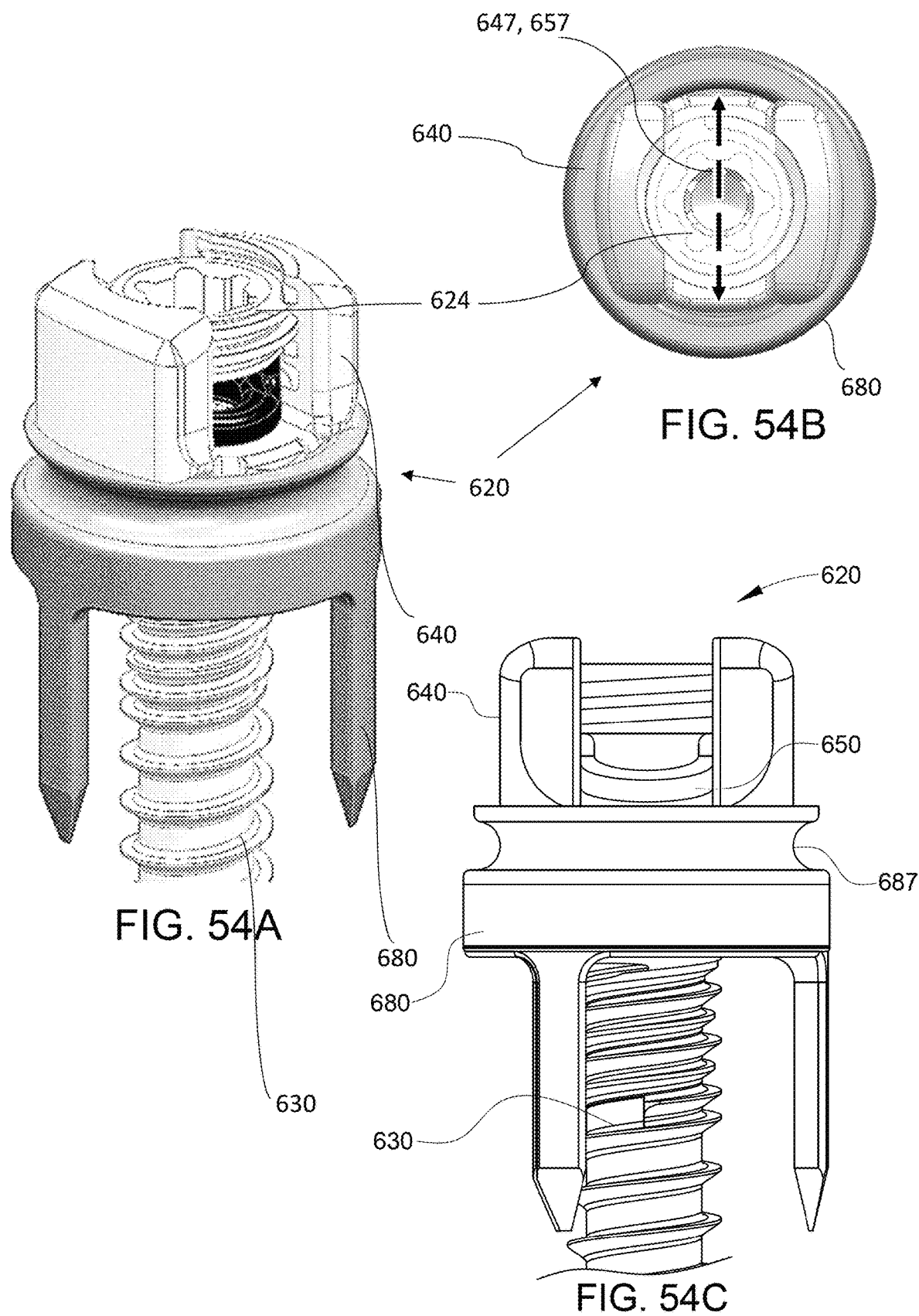

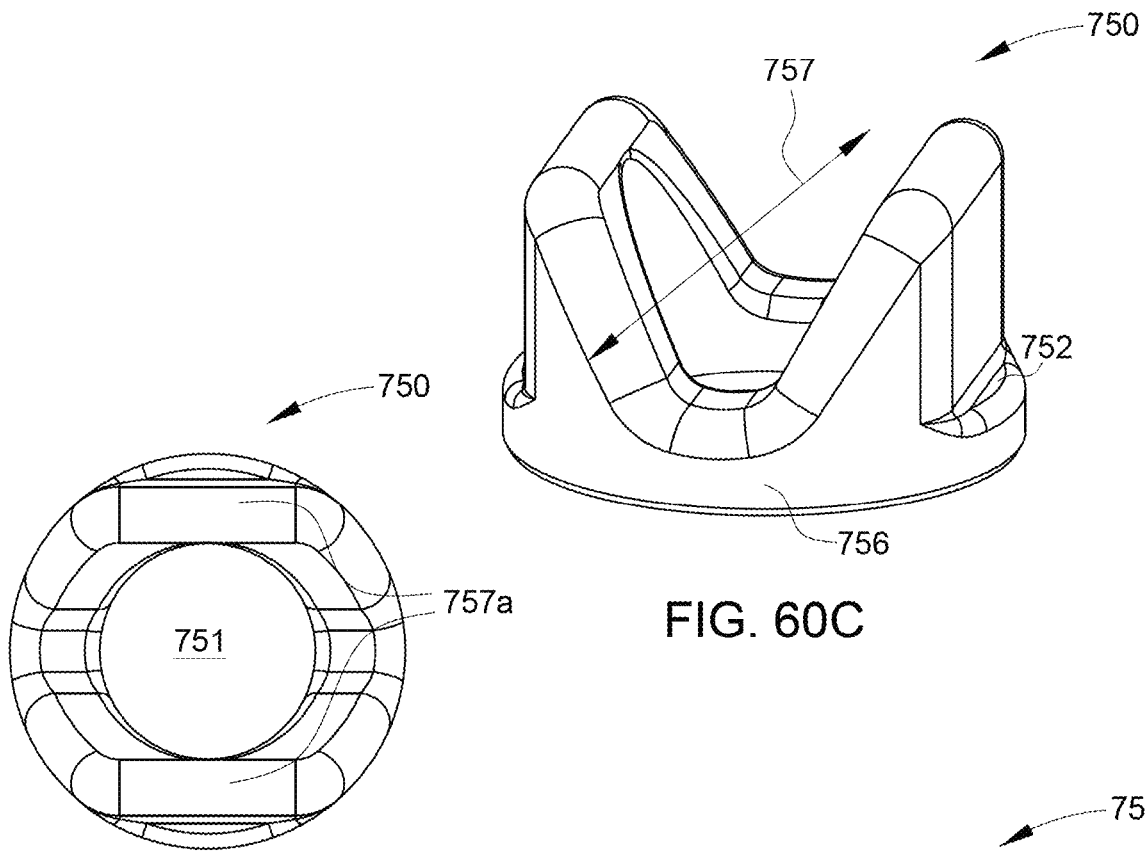
FIG. 60A
FIG. 60C
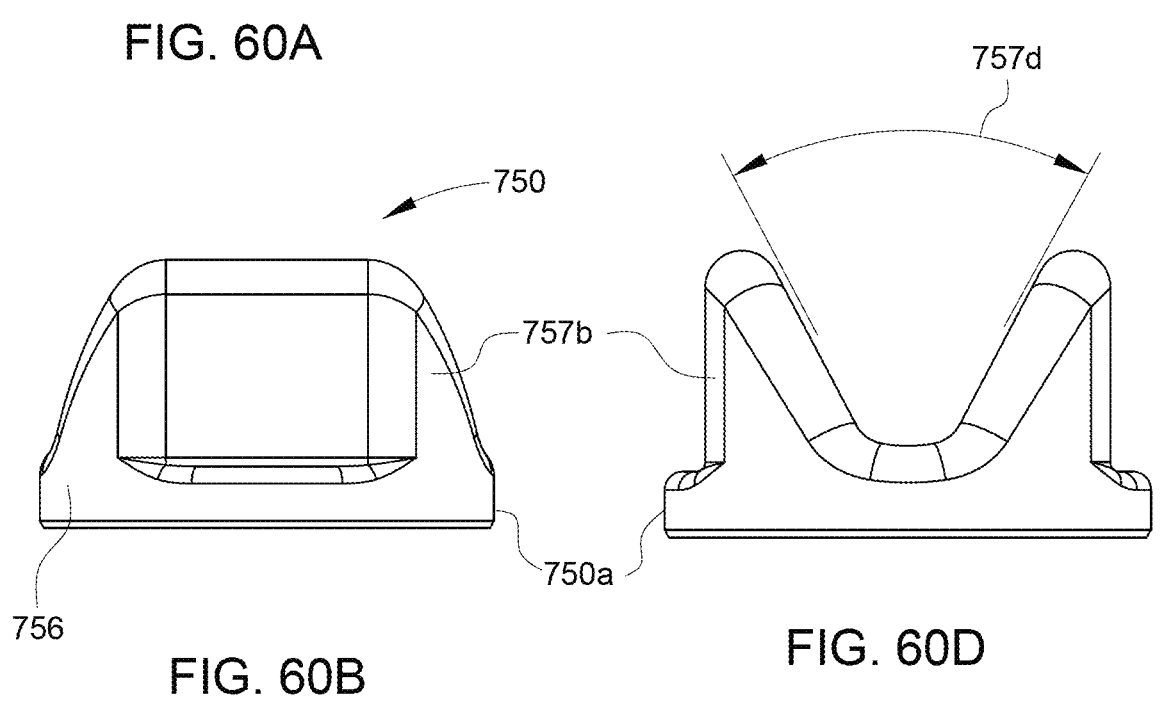
FIG. 60B
FIG. 60D

BONE ANCHORS WITH CORD RETENTION FEATURES

CROSS REFERENCE TO RELATED APPLICATIONS

This application claims the benefit of priority to U.S. Provisional Patent Application Ser. No. 62/811,318, filed Feb. 27, 2019, titled TETHERING PEDICLE FASTENER and U.S. Provisional Patent Application Ser. No. 62/882,238, filed Aug. 2, 2019, titled BONE ANCHOR WITH CORD RETENTION FEATURES, both of which are incorporated herein by reference.

FIELD OF THE INVENTION

Various embodiments pertain to devices for anchoring to bones, and especially devices for flexibly and dynamically connecting one bone to another bone.

SUMMARY OF THE INVENTION

One aspect of the present invention pertains to a bone anchor for a flexible connector. Other embodiments include a head including a top including a threaded receptacle and a pathway open to the top and adapted and configured for passage therethrough of a flexible connector. Yet other embodiments include a member including a pair of arms extending within the pathway for passage of a flexible connector, at least one of the arms including a first abutting surface. Still other embodiments include a set screw having threads adapted and configured to threadably couple to the threaded receptacle of the head, the set screw having a bottom and a second abutting surface; wherein tightening of the set screw to the head brings the first and second abutting surfaces into contact.

Another aspect of the present invention pertains to a bone anchor for a flexible connector. Other embodiments include a bone fastener having a top portion and a threaded portion adapted and configured to fasten to the bone. Yet other embodiments include a base including an aperture for receiving therein the bone fastener and a plurality of bone penetrating projections. Yet other embodiments include a head having a bottom, a top including a threaded receptacle, an internal pocket, and a pathway between the top and the bottom, and adapted and configured for passage therethrough of a flexible connector. Still other embodiments include a member including a pedestal having a bottom and received within the pocket of the head and a corridor therethrough for passage of a flexible connector including a first abutting surface. Still further embodiments include a set screw having a second abutting surface; wherein tightening of the set screw to the head frictionally captures the member between the set screw and the top of the bone fastener.

Another aspect of the present invention pertains to a bone anchor for a flexible connector. Other embodiments include a bone fastener having a top portion with a first diameter, and a threaded portion adapted and configured to fasten to the bone. Yet other embodiments include a head having a bottom, a top including a threaded receptacle, an internal pocket, an inner recess, and a pathway between the top and the bottom, the pathway being adapted and configured for passage therethrough of a flexible connector. Still further embodiments include an expandable split ring collar having a tapered aperture, wherein in an expanded state the minimum distance across the taper is greater than the first diameter, and in a compressed state the split ring collar fits within the inner recess and the minimum distance is less than the first diameter. Other embodiments include a member including a pedestal, the member being received within the pocket of the head and a pair of arms extending within the pathway of the head, the arms having a corridor therethrough for passage of a flexible connector.

Another aspect of the present invention pertains to a bone anchor for a flexible connector. Other embodiments include a base having at least one bone penetrating projection and adapted and configured to receive therethrough a bone fastener, the base including a groove extending around at least a portion of the periphery of the base, the groove being adapted and configured to receive a loop of flexible connector.

Yet another aspect of the present invention pertains to a bone anchor for a flexible connector. Other embodiments include a base having an aperture and of bone penetrating projection, the aperture adapted and configured to receive therethrough a bone fastener, the base including at least one eyelet attached to the periphery of the base adapted and configured to receive therein a portion of flexible connector.

Yet another aspect of the present invention pertains to a bone anchor for a flexible connector. Other embodiments include a base having a plurality of bone penetrating projections, the base having an attachment region adapted and configured for attachment to a flexible connector. Yet other embodiments include a separable head receivable on the base, the head including a top and a pathway open to the top and adapted and configured for passage of a flexible connector. Still further embodiments include a separable member adapted and configured to releasably couple to the head and having a corridor therebetween for passage of a flexible connector; wherein the attachment region of the base is located below the corridor.

Still yet another aspect of the present invention pertains to an apparatus for applying a force to a bone with a flexible connector. Other embodiments include a body having a top including a threaded receptacle and a first pair of opposing arms defining a first pathway therebetween adapted and configured for receiving therein a flexible connector, the first passageway having a first width proximate to the top. Yet another embodiment includes a member coupled to the head and having a second pair of opposing arms defining a second pathway therethrough for receiving therein the flexible connector, the second pathway located under the first passageway, the second pathway having a second width adjacent the first pathway that is greater than the first width.

Yet another aspect of the present invention pertains to an apparatus for applying a force to a bone with a flexible connector. Other embodiments include a body having a top and a first pair of arms, each the arm having a face that opposes the face of the other arm, the opposing faces defining a first pathway adapted and configured for compression of a flexible connector and open at the top. Yet other embodiments include a member configured to be received releasably coupled to the head, and a second pair of opposing arms defining a second open pathway therethrough for receiving therein the flexible connector, the second open pathway located under the first passageway.

Still another aspect of the present invention pertains to a bone anchor for a flexible connector having a top with a rounded portion, and a threaded portion adapted and configured to fasten to a bone. Yet other embodiments include a base for receiving therein the bone fastener, a pocket surrounding the aperture, and at least one bone penetrating projection. Still other embodiments include a head having a bottom adapted and configured to be received within the pocket, a top including a threaded receptacle, and an interior. Still other embodiments include a member including a pedestal having a bone fastener surface, the member being releasably coupled to the head, the member having a pair of arms defining a corridor therebetween for passage of a flexible connector, at least one of the arms including a first abutting surface. Yet further embodiments include a set screw having a bottom with a second abutting surface, and threads adapted and configured to threadably couple to the threaded receptacle of the head.

Yet another aspect of the present invention pertains to a bone anchor for a flexible connector. Other embodiments include a bone fastener having a top and a portion adapted and configured to fasten to a bone. Yet other embodiments include a base including a pocket, and at least one bone penetrating projection. Still further embodiments include a head having an interior adapted and configured to permit polyaxial pivoting of the bone fastener relative to the head. Yet other embodiment include a member within the head, the member having a pair of arms defining a corridor therebetween for passage of a flexible connector.

Yet another aspect of the present invention pertains to an apparatus for connection between a plurality of bone anchors. Other embodiments include a flexible connector having two free ends and a loop therebetween, the flexible connector having a length between the two free ends that is greater than the distance, wherein the flexible connector is adapted and configured to be placed in tension. Yet other embodiments include an end connector attached to at least one free end, the end connector being adapted and configured to application of a tension load onto the flexible connector.

Another aspect of the present invention pertains to an apparatus for connection between a plurality of bone anchors. Other embodiments include an anchoring ring having a circumference and an inner surface adapted and configured to be placed around a bone anchor, the anchoring ring having a first attachment location on one side of the circumference and a second attachment location on the other side of the circumference. Yet other embodiments include a first length of flexible connector having a first free end and a first other end, the first length of flexible connector being adapted and configured to be placed in tension, the first other end being coupled to the anchoring ring at the first attachment location. Still further embodiments include a second length of flexible connector having a second free end and a second other end, the second length of flexible connector being adapted and configured to be placed in tension, the second other end being coupled to the anchoring ring at the second attachment location. Yet other embodiments include an end connector attached to at least one of the first free end or the second free end, the end connector being adapted and configured to application of a tension load onto the flexible connector.

Still another aspect of the present invention pertains to an apparatus for connection between two bone anchors spaced apart by a distance. Other embodiments include a flexible connector having two ends, with one end including a loop, the flexible connector having a length between the two ends that is greater than the distance, wherein the flexible connector is adapted and configured to be placed in tension. Yet other embodiments include an end connector attached to the free end, the end connector being adapted and configured to application of a tension load onto the flexible connector, the end connector being adapted and configured to be removed from the free end after the tension load is applied.

Still yet another aspect of the present invention pertains to a bone anchor for a flexible connector having two ends, with one end including a loop, wherein the flexible connector is adapted and configured to be placed in tension, but substantially unable to withstand compression. Yet other embodiments include a base having an attachment region adapted and configured for looping attachment to the loop of the flexible connector. Still further embodiments include a separable head receivable by the base, the head including a top and a laterally extending pathway open to the top and adapted and configured for passage therethrough of the flexible connector; wherein the attachment region of the base is located below the pathway.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, the figures shown herein may have been created from scaled drawings, scaled models, or from photographs that are scalable. It is understood that such dimensions, or the relative scaling within a figure, are by way of example, and not to be construed as limiting unless so stated in a claim. Persons of ordinary skill will also recognize that CAD renderings may include lines that pertain to changes in surface geometry, and not necessarily to component features.

FIG. 17 is a top, side perspective view of a portion of the apparatus of FIG. 14.

FIG. 18 is a side elevational view of the apparatus of FIG. 17.

FIG. 19 is a side elevational view of the apparatus of FIG. 18, presented orthogonally.

FIG. 20 is a bottom plan view of the apparatus of FIG. 17.

FIG. 21 is a top plan view of the apparatus of FIG. 18, and presented orthogonally to FIG. 18.

FIG. 22 is a side, top, perspective view of a portion of the apparatus of FIG. 14.

FIG. 23 is a top plan view of the apparatus of FIG. 22.

FIG. 24 is a bottom plan view of the apparatus of FIG. 23.

FIG. 25 is a side elevational view of the apparatus of FIG. 23, and presented orthogonally to FIG. 23.

FIG. 26 is side elevational view of the apparatus of FIG. 24, and presented orthogonally to FIG. 24.

FIG. 32 is a top, side, perspective, CAD surface representation of an anchoring device according to another embodiment of the present invention.

FIG. 33 is a cross sectional view of the apparatus of FIG. 32, as presented down the centerline of the apparatus of FIG. 32.

FIG. 45A is a top plan view of a component from the apparatus of FIG. 39.

FIG. 45B is a side elevational cutaway representation of the apparatus of FIG. 45A.

FIG. 45C is a side elevational representation of the apparatus of FIG. 45A, presented orthogonally to FIG. 45A.

FIG. 45D is a top side perspective representation of the apparatus of FIG. 45A.

FIG. 46A is a top plan view of a portion of the apparatus of FIG. 39.

FIG. 46B is a side elevational view of the apparatus of FIG. 46A, and presented orthogonally to FIG. 46A.

FIG. 46C is a side, top perspective view of the apparatus of FIG. 46A.

FIG. 46D is a side elevational, cross sectional view of the apparatus of FIG. 46A.

FIG. 52D is a top plan view of an anchoring ring according to another embodiment of the present invention.

FIG. 52E is a top plan photographic representation of a tethering assembly according to another embodiment of the present invention.

FIG. 52F is a top, side, perspective photographic representation of an anchoring ring according to another embodiment of the present invention.

FIG. 53A is a top plan view of an arrangement of separate components for a tethering assembly according to another embodiment of the present invention.

FIG. 53B is a top plan view of the assembly of the devices of FIG. 53A.

FIG. 53C is a side elevational CAD representation of the apparatus of FIG. 53B being used to anchor to tether together two adjacent implanted bone anchors.

FIG. 54A is a top, side perspective CAD representation of an apparatus according to another embodiment of the present invention.

FIG. 54B is a top plan view of the apparatus of FIG. 54A.

FIG. 54C is a side elevational view of the apparatus of FIG. 54A.

FIG. 60A is a top plan view of a component of the apparatus of FIG. 57.

FIG. 60B is a side elevational view of the apparatus of FIG. 60A, and shown orthogonally to FIG. 60A.

FIG. 60C is a top, side perspective view of the apparatus of FIG. 60A.

FIG. 60D is a side elevational view of the apparatus of FIG. 60A, and shown orthogonally to FIG. 60B.

ELEMENT NUMBERING

Figure 1A:
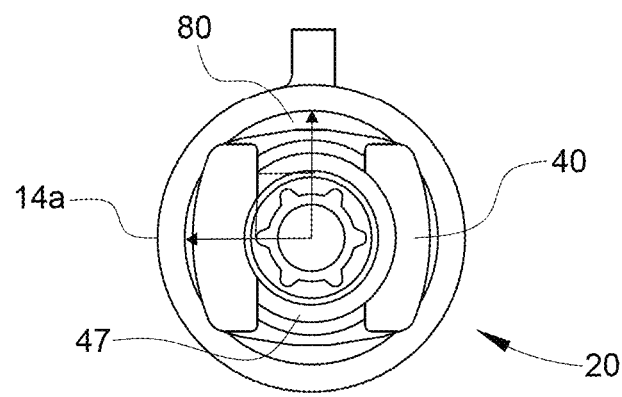
FIG. 1A is a top plan, CAD surface representation of a bone anchoring device according to one embodiment of the present invention.

The following is a list of element numbers used with all of the embodiments, and at least one noun used to describe that element. The "X" for all of these numbers is removed or replaced with a number (0 or greater) in the text and drawings of this application. Consistent with statements made elsewhere in this specification, these various 2-digit element numbers are used among multiple embodiments, and aspects of a particular element stated for one embodiment can be applied to the same element number in a different embodiment, except as shown and described differently, and as would be understood by a person of ordinary skill in the art. It is understood that none of the embodiments disclosed herein are limited to these nouns, and these element numbers can further include other words that would be understood by a person of ordinary skill reading and reviewing this disclosure in its entirety

| Element | Description |
|---|---|
| X10 | vertebra |
| X14 | flexible member, tether, sutures, cables, springs, tape, and any of woven, braided, or flat, as examples |
| a | loop |
| b | free end |
| c | interconnection angle |
| d | captured end |
| X16 | tethering assembly |
| X17 | Anchoring ring |
| a | Relieved sector |
| b | Interfering sector |
| c | Passage for flexible connector |
| d | Split end |
| e | Interlocking ends |
| f | Connector for instrument |
| X18 | End connector for instrument |
| X20 | bone anchor assembly; anchoring device |
| X21 | centerline |
| X24 | screw |
| a | abutting surface |
| b | bottom surface |
| X30 | fastener |
| X31 | staple interface |
| a | threads; locking |
| b | smooth; spherical; rounded |
| c | conical |
| d | ridges |
| X32 | head |
| a | rounded surface; spherical surface |
| X33 | tip |
| X34 | collar interface |
| X35 | threads |
| a | double lead cortical threads |
| b | single lead cancellous |
| c | double lead cortical threads |
| X36 | neck |
| X39 | top surface; saddle interface |
| a | surface |
| b | shoulder; edge |
| X40 | head assembly |
| a | body; head |
| b | base |
| X41 | central aperture |
| X42a | collar registration features |
| b | saddle registration features |
| c | staple seating o.d. |
| X43 | bottom surface |
| X45 | collar recess |
| a | Line or plane of head to fastener contact (dot - dash line) |
| X46 | saddle pocket; saddle locating feature |
| X47 | tether pathway |
| a | top surface |
| b | arm |
| c | threads, set screw |
| d | minimum distance; width between arms |
| e | opposing faces |
| X48 | outer surface; instrument interface |
| X49 | locking groove |
| a | retainer feed aperture |
| X50 | saddle member |
| a | body interface; outer diameter |
| X51 | central aperture |
| X52 | registration features |
| X56 | rim; pedestal; locating feature |
| X57 | corridor |
| a | top surface |
| b | arm |
| c | cross sectional area |
| d | narrowing groove; V-groove |
| e | Load line or plane; centroid (large dashed line) |
| H | height |
| W | width |
| X58 | fastener head interface; surface |
| X59 | bottom surface; fastener interface |
| a | pocket |
| b | ridge |
| X60 | collar |
| a | split |

| | | |
|---|---|---|
| X61 | central aperture | |
| X62 | registration features | |
| X64 | fastener interface | |
| b | smooth; rounded; spherical | |
| c | conical | |
| X65 | top surface | |
| a | relief pocket | |
| X66 | head contacting surface | |
| X69 | locking groove | |
| X70 | retainer | |
| X71 | split; free ends | |
| X80 | staple; bone anchor | |
| a | bone facing surface | |
| b | base | |
| X81 | fastener interface; aperture | |
| a | threaded | |
| b | smooth; rounded; spherical | |
| c | conical | |
| d | cylindrical | |
| e | radial clearance | |
| f | line or plane of contact (small dashed line) | |
| X83 | head receiving pocket | |
| X84 | projection | |
| X86 | groove | |
| a | overhanging circumferential lip | |
| b | relieved sector | |
| c | transverse height | |
| d | center | |
| X87 | tether pathway | |
| a | circumferential | |
| b | transverse | |
| c | load line or plane of tensile load from loop (large dashed line) | |
| X88 | eyelet | |

DETAILED DESCRIPTION OF ONE OR MORE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "various embodiments" or "preferably," refers to features and aspects that are present in at least one embodiment, but which are optional for some embodiments, it therefore being understood that use of the word "preferably" implies the term "optional."

The use of an N-series prefix for an element number (NXX.XX) refers to an element that is the same as the non-prefixed element (XX.XX), except as shown and described. As an example, an element 1020.1 would be the same as element 20.1, except for those different features of element 1020.1 shown and described. Further, common elements and common features of related elements may be drawn in the same manner in different figures, and/or use the same symbology in different figures. As such, it is not necessary to describe the features of 1020.1 and 20.1 that are the same, since these common features are apparent to a person of ordinary skill in the related field of technology. Further, it is understood that some features 1020.1 and 20.1 may be backward compatible, such that a feature of a later discussed embodiment (NXX.XX) may include features compatible with other various embodiments that were discussed earlier (MXX.XX), as would be understood by those of ordinary skill in the art. This description convention also applies to the use of prime ('), double prime ("), triple prime ('") and star or asterisk (*) suffixed element numbers. Therefore, it is not necessary to describe the features of 20.1, 20.1', 20.1", 20.1'" and 20* that are the same, since these common features are apparent to persons of ordinary skill in the related field of technology.

What follows are paragraphs that express particular embodiments of the present invention. In those paragraphs that follow, some element numbers are prefixed with an "X" indicating that the words pertain to any of the similar features shown in the drawings or described in the text. However, those of ordinary skill in the art will recognize various other non-X prefixed element numbers that discuss features applicable to other embodiments.

This document may use different words to describe the same element number, or to refer to an element number in a specific family of features (NXX.XX). It is understood that such multiple, different words are not intended to provide a redefinition of any language herein. It is understood that such words demonstrate that the particular feature can be considered in various linguistical ways, such ways not necessarily being additive or exclusive.

Figure 10:
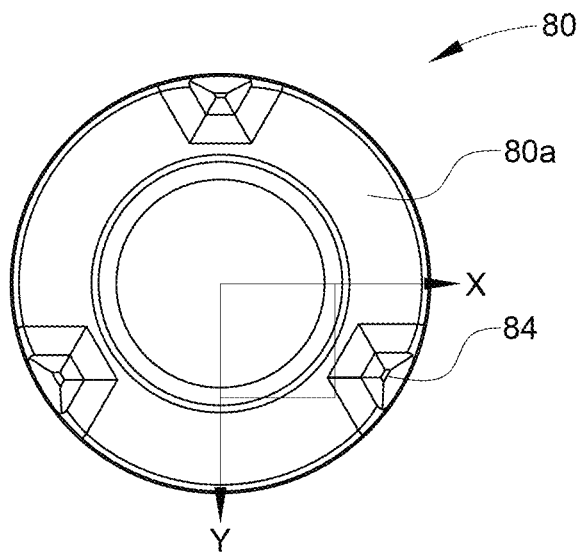
FIG. 10 is a bottom plan view of the apparatus of FIG. 8, and shown orthogonally.
Figure 11:
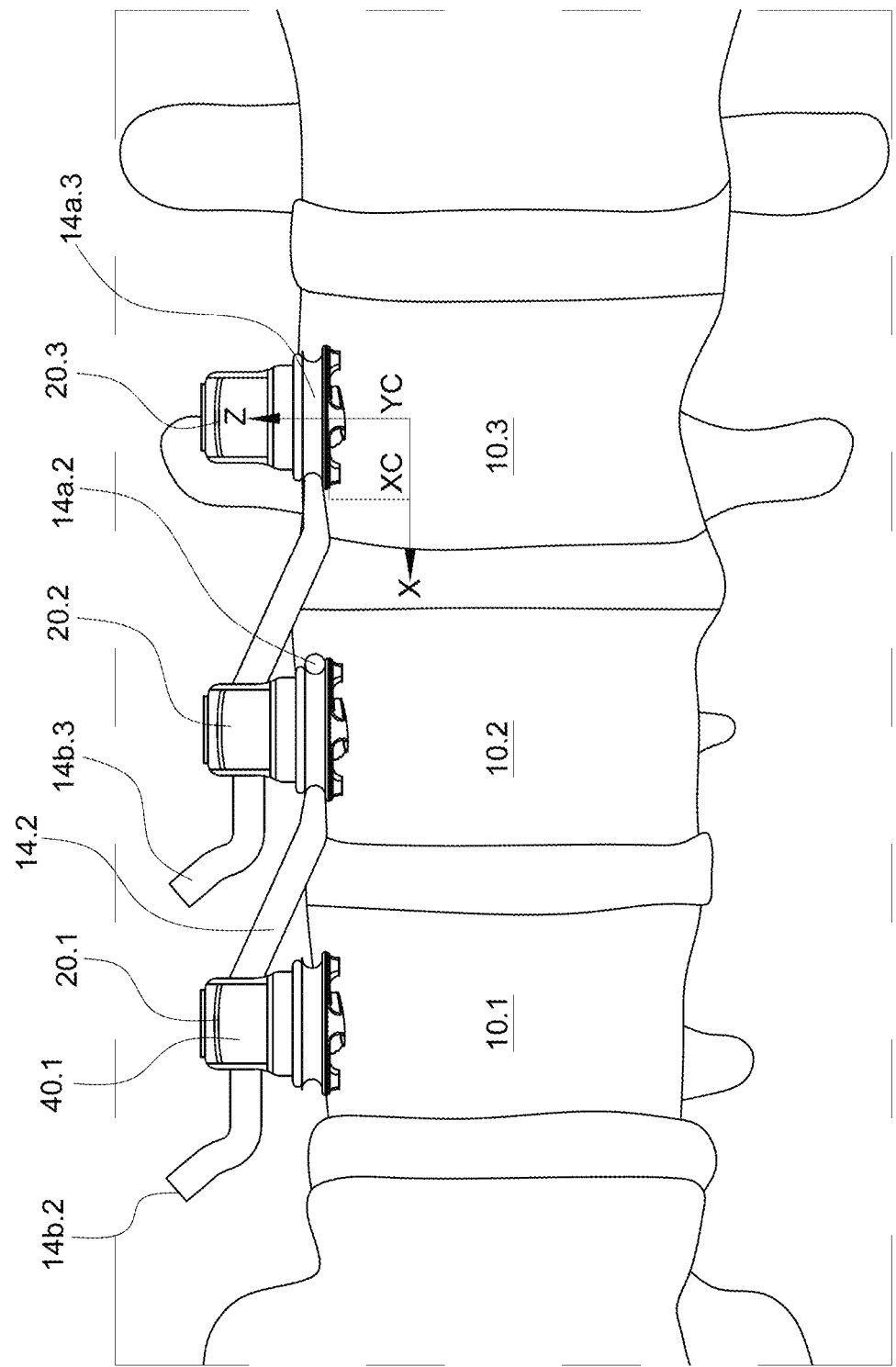
FIG. 11 is a side elevational view of adjacent vertebra that incorporate a plurality of the devices of FIG. 1B, shown tethered together in segments.

FIGS. 1-11 depict various views of a bone anchor or anchoring device 20 according to one embodiment of the present invention. In one embodiment, device 20 includes a staple X80 for attaching a loop 14a of a tether to a vertebra, and a bone fastener X30 that attaches a head assembly X40 to a vertebra. The head assembly is adapted and configured to grasp securely to an end 14b of a tether. Preferably, the combination of loop and staple are located on the same bone, and preferably coaxially with the assembly of the head and fastener. In some embodiments, one such combined assembly is located proximate to a similar or identical assembly, with the tether looped attached to the staple of one device being securely gripped by the head assembly of the other device, as shown in FIG. 11. Still further embodiments will be disclosed herein that pertain to anchors in which a head and fastener assembly is attached to a bone along with a staple, but in which the loop around the periphery of the staple is optional.

Various embodiments refer to the use of a flexible connector 14 that is adapted and configured to provide tension between two devices, but substantially unable to provide compression between the two devices, and substantially unable to provide a torque from one assembly to the other, although it will be understood that because of various spacing differences between adjacent tethering devices, the flexible connector can provide a moment between the two devices. Examples of flexible connectors include tethers, sutures, wire, and springs.

Figure 1B:
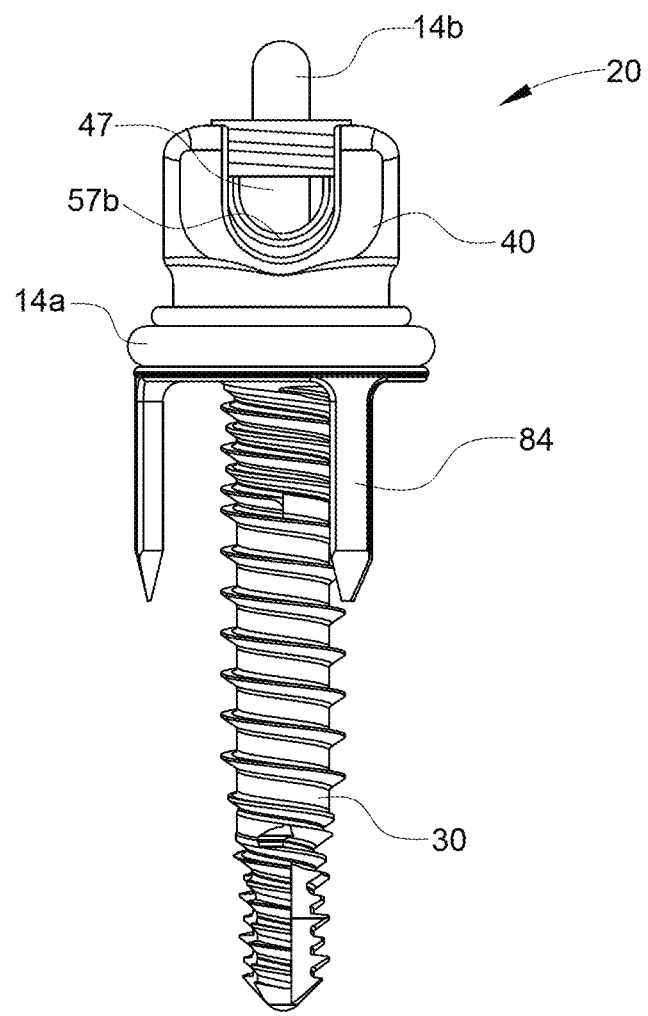
FIG. 1B is a side elevational view of the apparatus of FIG. 1A, shown orthogonally.

Referring to FIGS. 1A and 1B, it can be seen that the combined tethering assembly 20 includes a head assembly 40 including a set screw 24, internally received saddle member 50 and collar member 60. This head assembly 40 is rotatably captured (after assembly, which will be described later) to the head 32 of a bone fastener 30. After implantation, the bone fastener is securely received within an aperture and fastener interface 81 of a staple 80. The implanted device X20 is coupled to a vertebra (or other bone, in non-spinal applications) by both the threads X35 of fastener X30, and by the projections X84 of staple X80. In one embodiment, a fastener X30 includes larger double lead cortical threads 35a proximate to the point of entry of the fastener into the vertebra, a midsection with single lead cancellous threads 35b, and near the tip 33 a section of smaller double lead cortical threads 35c for connection to the distal side of the vertebra. However, it is understood that various embodiments of the present invention contemplate any manner of attaching a head X40 to a vertebra, whether by a fastener or by other means, and including fasteners having only cortical and cancellous thread, or only cortical thread. In some embodiments the head X40 may also be attached to the vertebra or bone by devices including straps.

Figure 4:
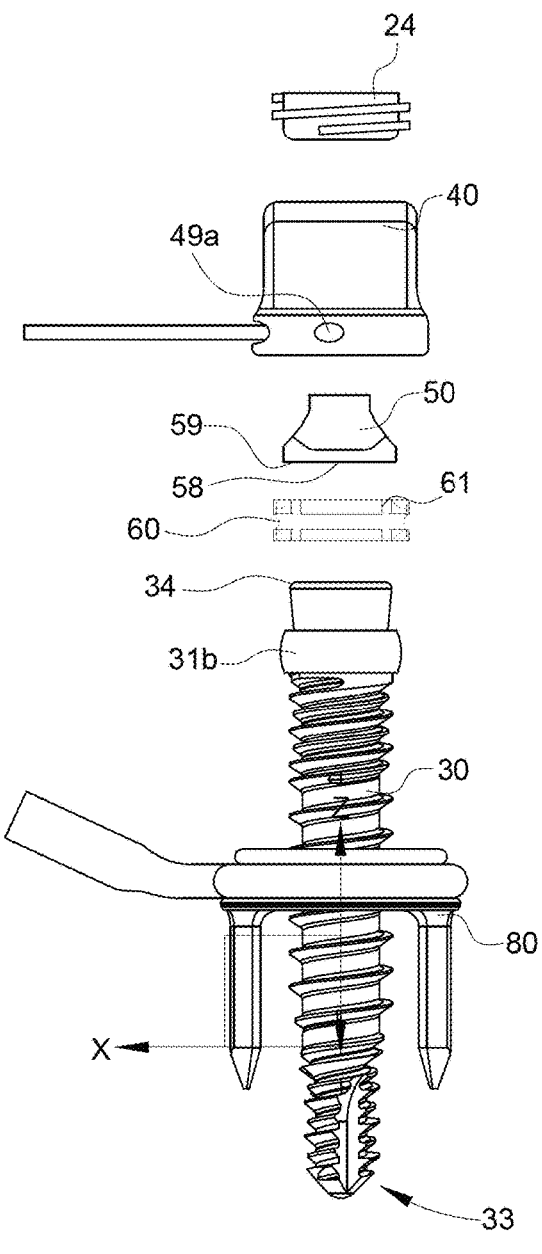
FIG. 4 is a side elevational exploded view of the apparatus of FIG. 2, as taken from the opposite side.
Figure 5:
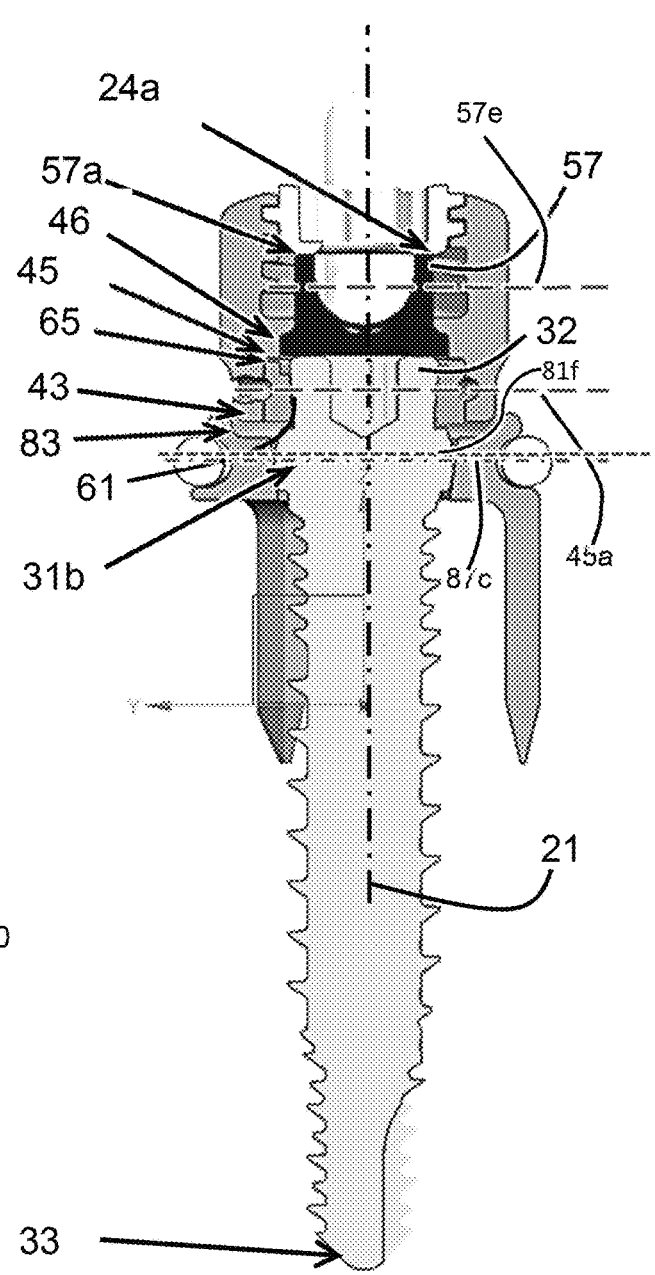
FIG. 5 is a cross sectional view of the apparatus of FIG. 1, as taken in the centerline of the device and in the plane of the figure.

FIGS. 4 and 5 show various aspects of the internal construction of device 20. A head assembly 40 includes a body 40a that is adapted and configured to receive therein a set screw 24, a saddle 50, and a collar 60, although other embodiments of the present invention contemplate a head assembly 40 having fewer internal components. The discussion of the various features of the body of head assembly 40 that interface with corresponding features of the saddle X50 and collar X60 will be described in the discussion of device 120, which in some embodiments has an arrangement of internal components, similar to that of device 20.

In one embodiment, the head assembly X40 is rotatably coupled to, and captures, head X32 of fastener X30, at the interface of the tapered outer diameter of head X32 within a conically tapered central aperture X61 (as seen in FIGS. 5 and 22). Prior to implantation in a bone, in a preferred embodiment the conical surfaces X61 and X32 are coaxial and for that reason head assembly X40 is generally free to rotate about the centerline 21. In the embodiments shown in FIGS. 5, 13, and 33, the collar X60 preferably has a substantially cylindrical outer surface that is captured within a substantially cylindrical recess 45 of the body of head X40. An embodiment 320 permitting polyaxial movement of the spherical head 332 of fastener 330 relative to a spherical inner surface 361 of collar 360 will be described later with regards to FIG. 34. It is further understood that the devices 20, 120, and 220 can likewise permit polyaxial movement in those embodiments including spherical interfaces.

Figure 6:
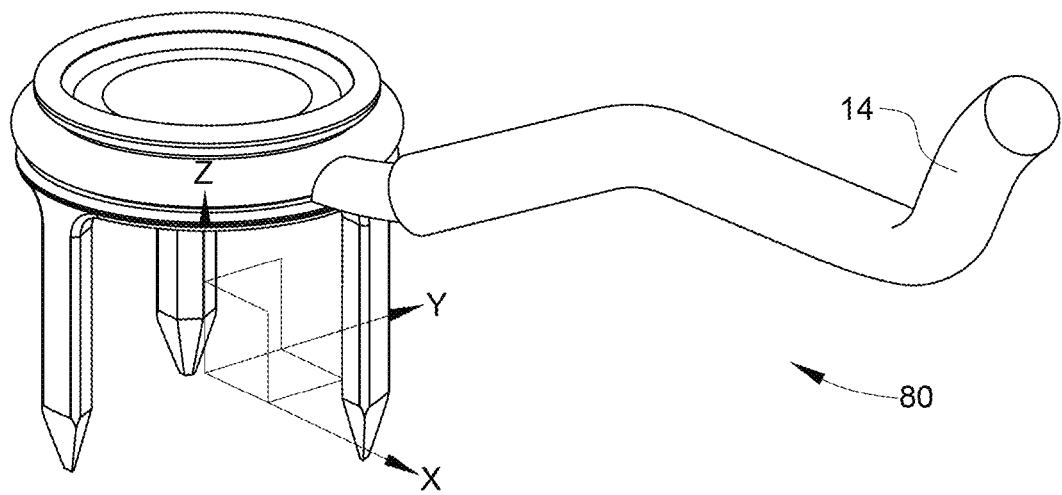
FIG. 6 is a top, perspective view of a portion of the apparatus of FIG. 3.

Referring to FIGS. 5-10, some embodiments include a staple 80 adapted and configured for fixation to a bone. Although member 80 can be coupled to the bone in any manner, in device 20 the coupling of member 80 to the bone is by way of a plurality of projections 84 that are adapted and configured to penetrate the cortical layer of bone. In some embodiments, and as best seen in FIG. 10, a member 80 preferably includes a plurality of projections 84 that are circumferentially spaced around the periphery of member 80. Further, member 80 preferably includes a circumferential groove 86 that is sized to receive within it a loop 14a of a flexible material. In some embodiments, this loop is fabricated around staple 80 during manufacturing, such that a device 20 is available to the user with a pre-attachment of a section of flexible connector 14, having both the loop 14a and a free end 14b (as best seen in FIG. 6). Yet other embodiments contemplate the looping of a flexible connector onto a member 80 at any time prior to or during implantation, and in still other embodiments a member X80 that is not looped or otherwise connected to a flexible connector.

In yet other embodiments of the present invention, the anchoring device X20 comprises a head assembly X40 that is attached to a bone in any manner, including as examples bodies X40a that include integral projections, cortical threads, interfaces for strap-type attachments, and the like. In such embodiments, there need not be a separate fastener. In still further embodiments, the anchoring device comprises a head assembly X40 and a fastener X30, but without any staple member X80.

Figure 7:
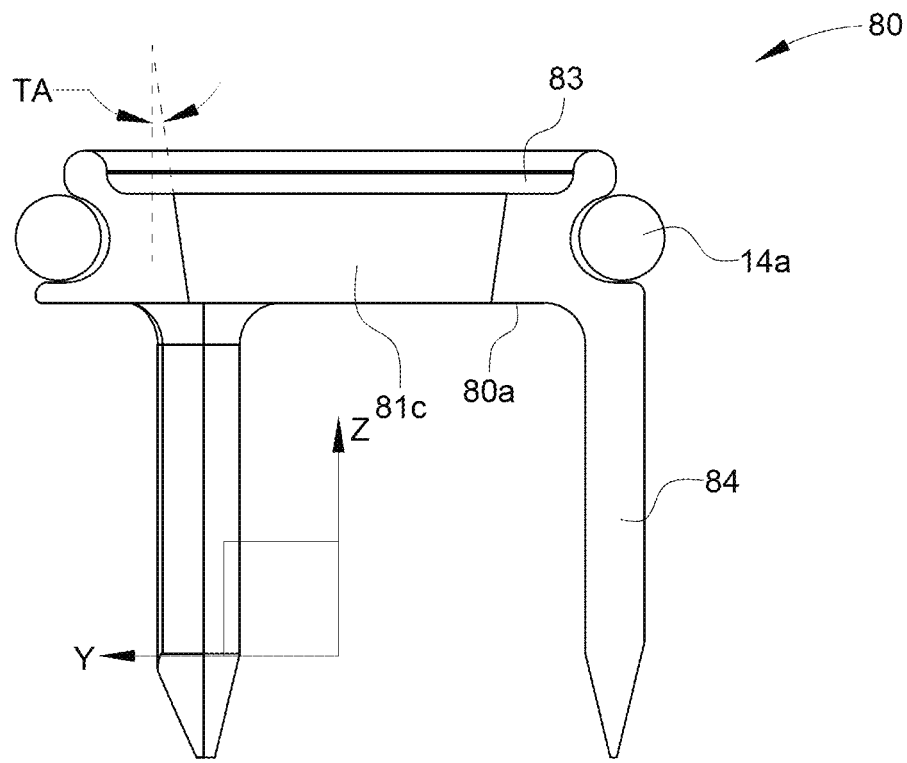
FIG. 7 is a side elevational view of a portion of the object of FIG. 5.
Figure 8:
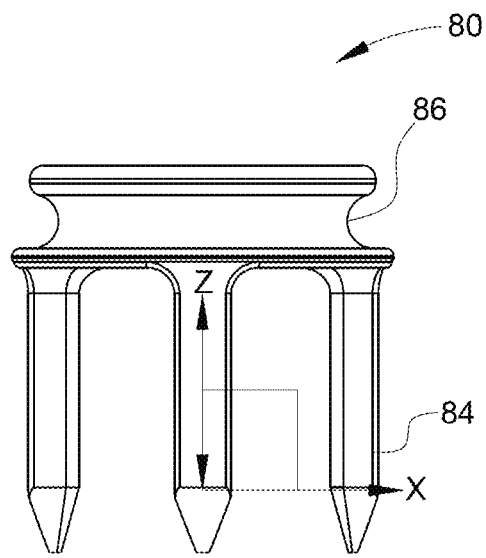
FIG. 8 is a side elevational view of a portion of the apparatus of FIG. 7.
Figure 9:
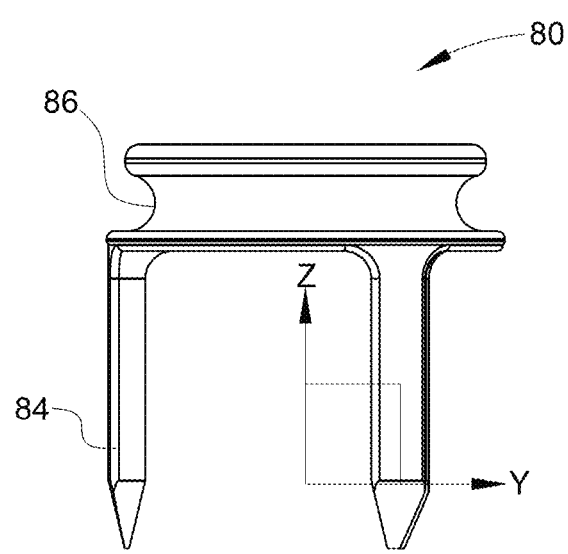
FIG. 9 is an orthogonal view of the apparatus of FIG. 8.

FIGS. 5 and 7 depict the interface between the fastener X30 and the staple X80. In one embodiment, fastener 30 includes a staple interface 31b that is preferably smooth and rounded, and in some embodiments at least partially spherical. This staple interface 31b is received within a fastener aperture 81, best seen in FIG. 7. As shown, staple 80 includes a conically shaped aperture 81c that has a maximum diameter on the top of staple 80, proximate to head receiving pocket 83. Referring to FIG. 7, it can be seen that the tapered surface has a taper angle TA. In some embodiments, the minimum diameter of the aperture 81c is located at the underside, bone face surface 80a. However, it is understood that the minimum diameter can be located intermediate of these top and bottom surfaces of the platform of staple 80, such that the minimum diameter is located midway along the thickness. However, it is further understood that the aperture 81 of staple 80 may also be generally smooth and rounded, and in some embodiments partly spherical.

Referring again to FIG. 5, the staple interface 31b of fastener 30 has a maximum outer diameter that is less than the maximum inner diameter of aperture 81, but larger than the minimum diameter of aperture 81. By this sizing, it can be seen that a fastener X30 (whether rotatably coupled to a head assembly 40 or not) can be received from the top opening located in the head proximate to the receiving pocket 83. However, because the maximum diameter of the staple interface 31 is larger than the minimum diameter of the aperture 81, the fastener is unable to pass completely through the aperture, and instead comes into an interfering-type contact with the aperture 81 of staple 80. It can be understood from FIG. 5 that tightening of fastener X30 into a vertebra will result in compression of staple 80 into the vertebra once this interfering contact has been established.

In device 20, the fastener has a staple interface 31b that is rounded or spherical, and fits within a conically tapered aperture 81c, such that the interface between the fastener and the staple can be considered a line of contact. However, because of the spherical (or semi-spherical) outer surface 31b, this line of contact may trace as a circle on aperture 81c, or as an ellipse in those instances where the centerline of aperture 81 is not coincident with the centerline of the fastener (such as when the head/fastener assembly 40/30 is tilted relative to the centerline of the staple 80). By this interaction of a conical surface with a spherical surface, device 20 permits a degree of angular misalignment between the staple and the head/fastener assembly.

Figure 2:
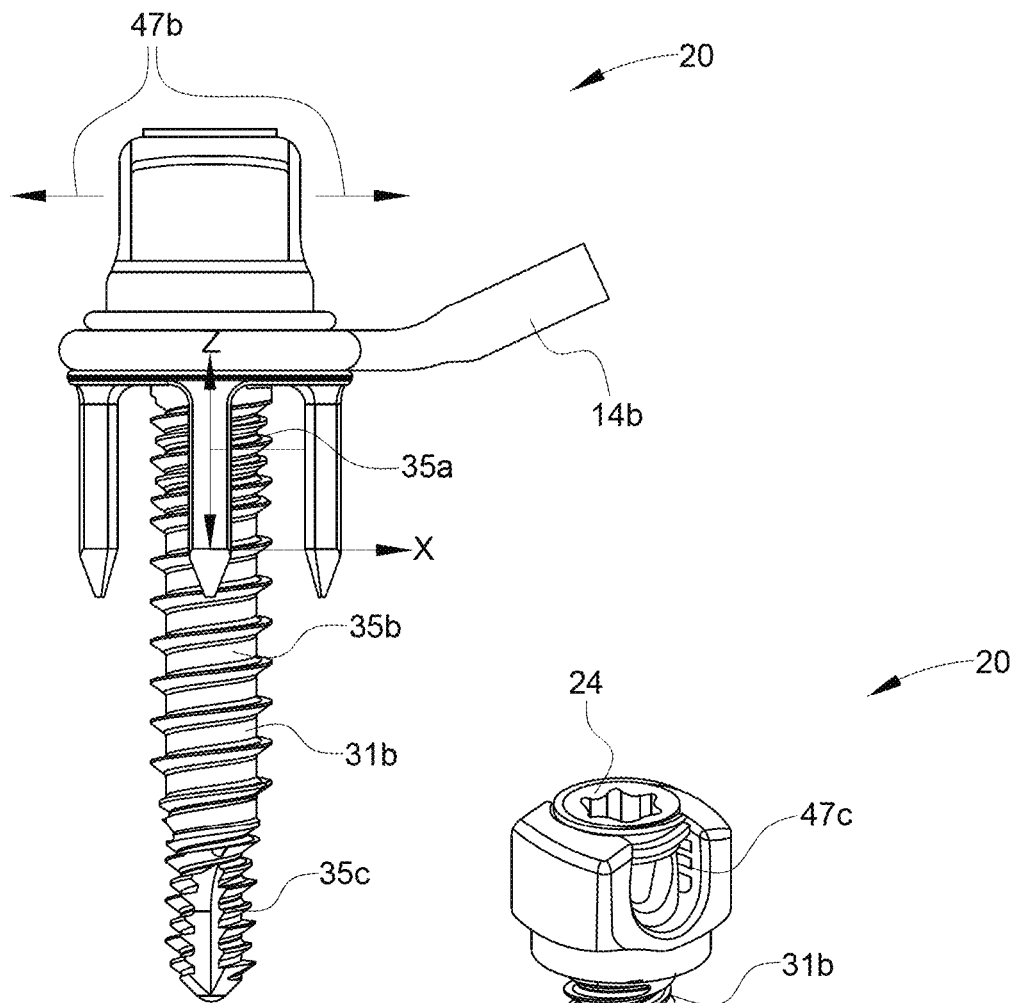
FIG. 2 is a side elevational view of the apparatus of FIG. 1B.
Figure 3:
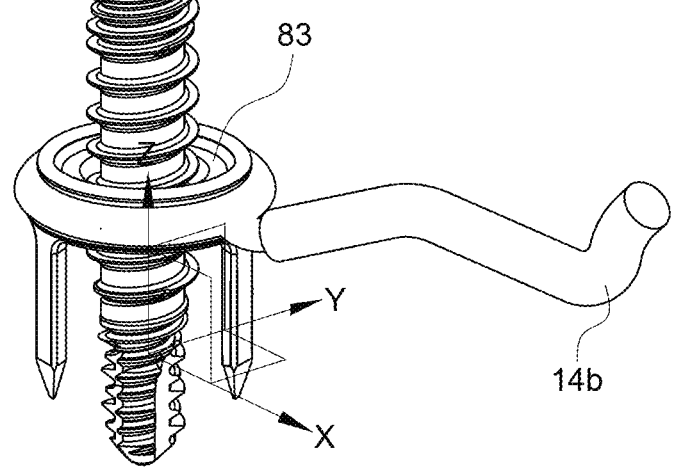
FIG. 3 is a partially exploded perspective view of the apparatus of FIG. 2.

Components 50 and 60 are loaded into a head 40a through the bottom side 43 (as best seen in FIGS. 4 and 5). It can be seen that a saddle member 50 includes a cylindrical base or pedestal 56, with a pair of upwardly extending arms 57 defining a corridor 57b between them. Referring to FIGS. 1B, 2 and 5, it can be seen that the corridor 57b is nested within the tether pathway 47b, with the corridor and the pathway being generally aligned. Preferably, the arms 57 extend at least partly between the threaded portions 47c of body 40a, as shown in FIGS. 1B and 5. In some embodiments, a saddle 50 includes arms 57 having top surfaces 57a, with at least one of these top surfaces 57a coming into contact with a bottom abutting surface 24a of a set screw 24.

In this manner, and referring again to FIGS. 1B and 5, it can be seen that in some embodiments this hard abutting contact between the set screw and the saddle establishes a region in the corridor 57b that has a fixed cross sectional area. In some embodiments, this cross sectional area is approximately D-shaped, although yet other embodiments contemplate any manner of shape created by the abutment of the set screw and at least one of the arms 57. In some embodiments, this cross sectional area is selected to provide a predetermined amount of compression onto a flexible member placed within the corridor. In still further embodiments, the set screw is tightened to frictionally restrain the tether within the corridor, but without any abutting contact between the set screw and the saddle member. In those embodiments utilizing certain tethering materials fabricated from organic polymers, the predetermined, fixed cross sectional area of the corridor can be less than about fifty percent of the free, uncompressed cross sectional area of the tether, and in still further embodiments less than about thirty percent of the free, uncompressed tether cross sectional area. Those of ordinary skill in the art will recognize that the selection of the geometric features for the fixed cross sectional area of the corridor of the fully assembled head 40 can be selected based on the type of material used for the flexible material (noting for example differences between a wound metallic material and a polymer), as well as for differences in the method of manufacturing (comparing for example loosely packed polymer material vs. densely packed polymer material).

Referring to FIG. 5, as the set screw 24 is tightened, the saddle member 50 becomes frictionally captured between the bottom surface 24a of the set screw and the top surface of the head 32 of fastener 30. By this tightening, a predetermined compression is applied to the flexible connector (by way of the fixed cross sectional area referred to above), the saddle member is frictionally locked in place, and the head assembly 40 is frictionally locked in place.

Referring to FIG. 11, a plurality of devices 20 are shown attached to different vertebrae, and interconnected to one another. A first device 20.1 is attached to a first vertebra 10.1, a second device 20.2 is attached to an adjacent vertebra 10.2, and a third device 20.3 is shown attached to a vertebra 10.3. It can be seen that the flexible connector 14.3 from connector 20.3 extends from the loop 14a.3 and through the head assembly 40.2, with the distal free end 14b.3 extending beyond fastener 20.2. In this manner, a single segment of tether can provide tension between vertebrae 10.2 and 10.3. Likewise, a similar connection is shown between vertebrae 10.1 and 10.2 by way of tether 14.2. Although what has been shown and described are a plurality of adjacent anchoring devices 20 attached in pairs, it is also understood that the free end 14b of a tether 14 can be long enough to extend to yet a third attachment head, such as if free end 14b.3 were attached to head 40.1.

FIGS. 12-31 depict various views of a tethering assembly 120 according to another embodiment of the present invention. In a manner similar to that described for device 20, device 120 includes a head assembly 140 that is rotatably captured to a fastener 130, with assembly 140 and fastener 130 being substantially coaxial.

Figures 12, 13:
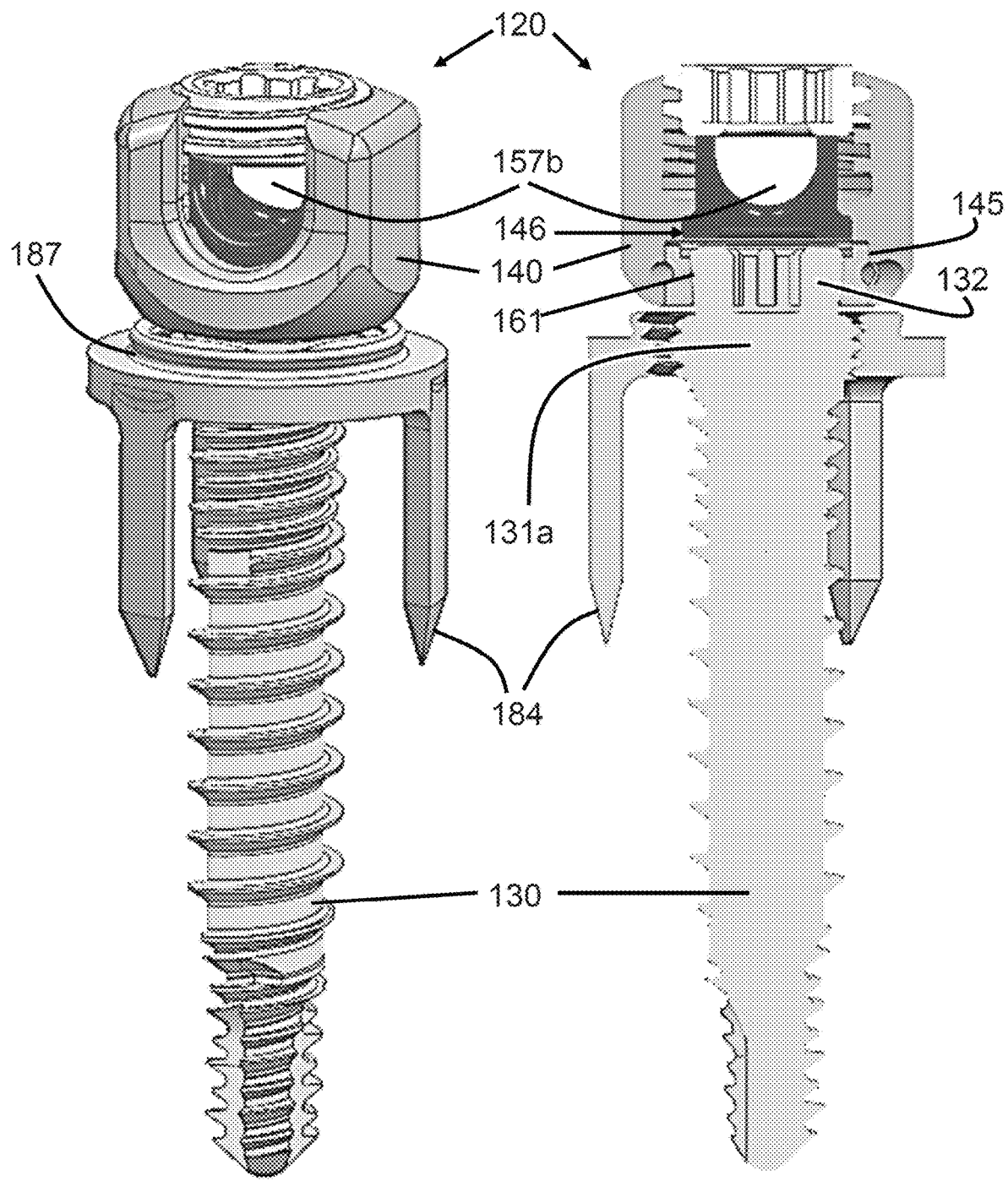
FIG. 12 is a perspective, side elevational CAD surface representation of an anchoring device according to another embodiment of the present invention.
FIG. 13 is a side elevational cross sectional representation of the apparatus of FIG. 12.

In some embodiments, this captured assembly of 140 and 130 are threadably received within a member 180 that is attached to the bone. As shown in FIGS. 12 and 13, the attachment of device 180 is by way of a plurality of sharp projections 184 that are adapted and configured to penetrate the cortical structure of a bone. However, member 180 can be attached to a bone in any manner.

Figures 15, 16:
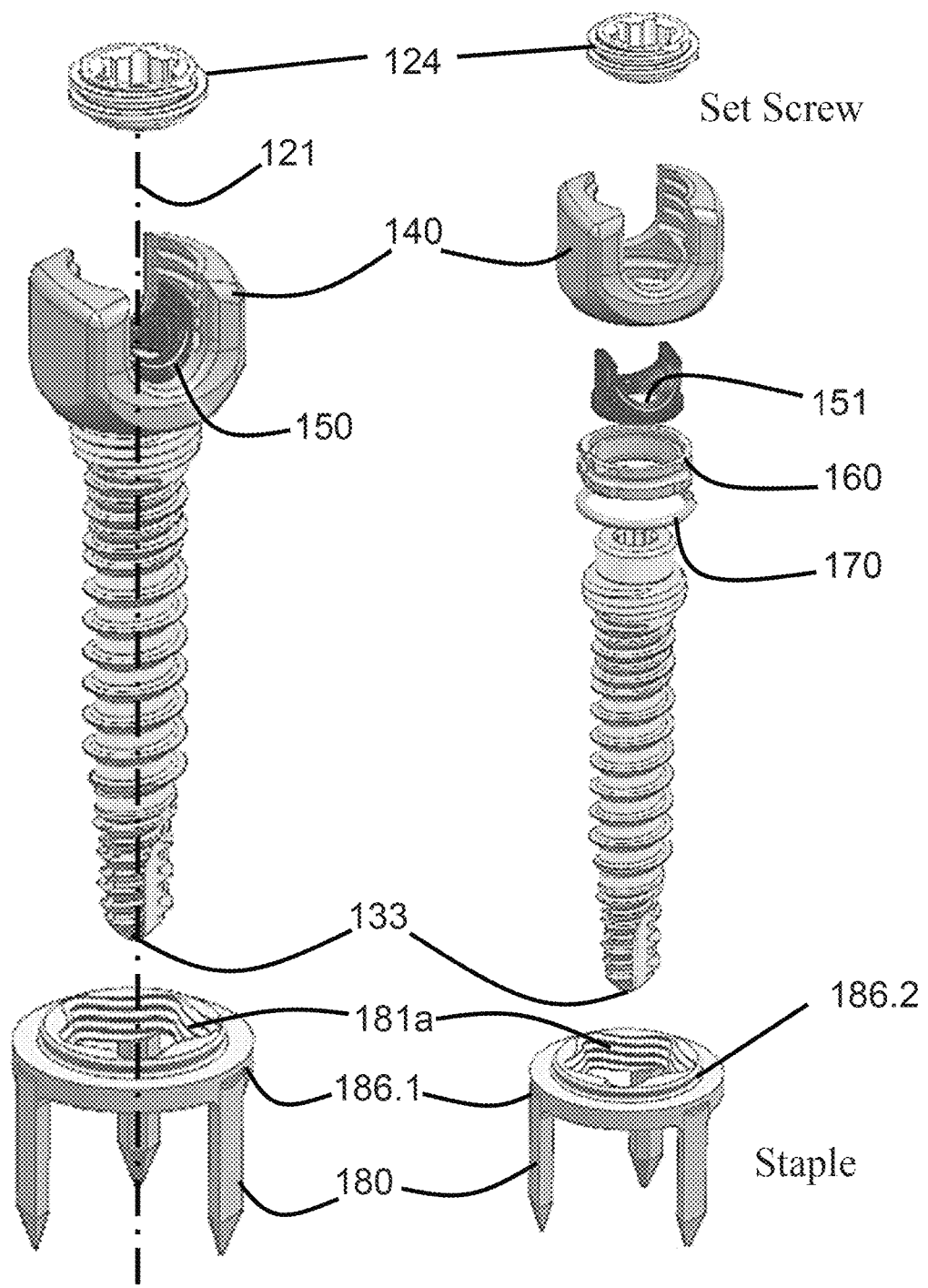
FIG. 15 is a perspective, partially exploded view of the apparatus of FIG. 12.
FIG. 16 is a perspective exploded view of the apparatus of FIG. 15.

In one embodiment, fastener 130 includes a threaded interface 131a that is received within a threaded aperture 181a of a staple 180. In some embodiments, the threaded interface between the fastener and the staple is adapted and configured to provide frictional locking, although in other embodiments yet other threaded interfaces are contemplated. One example of a locking interface is shown in FIGS. 15 and 16, although other embodiments contemplate any type of locking interface.

Members 180 and 80 can differ with regards to the configuration of their periphery. As previous discussed, in some embodiments staple 80 includes a peripheral groove 86 adapted and configured to receive within it a loop of a flexible connector. In device 120, the outermost periphery 186.1 of staple 180 can be plain and grooveless. In some such embodiments, it is not contemplated that staple 180 receive a loop of flexible connector. However, it is recognized that in yet other embodiments a staple 180 will include a smaller diameter peripheral surface 186.2, which can include a groove for looping attachment to a flexible connector.

FIGS. 13 and 17-31 depict the various component features that provide interfaces among the body 140a, collar 160, and saddle 150. Those of ordinary skill in the art will recognize the substantial similarity with features shown in FIG. 5 and discussed with regards to device 20.

Referring to FIGS. 27-31 and 13, it can be seen that a body 140a for a head assembly includes a base 140b with a pair of upwardly extending opposing arms 147a. These arms define between themselves a first, larger tether passageway 147b, which in some embodiments is oriented laterally, and substantially perpendicularly, to the centerline 121. In some embodiments, each of the arms 147a include internal threads adapted and configured to threadably receive a set screw 124. However, in yet other embodiments yet other locking interfaces are contemplated, including as one example a one-way, press-to-fit, ratcheting interface between a device 124 and arms 147b.

Figure 14:
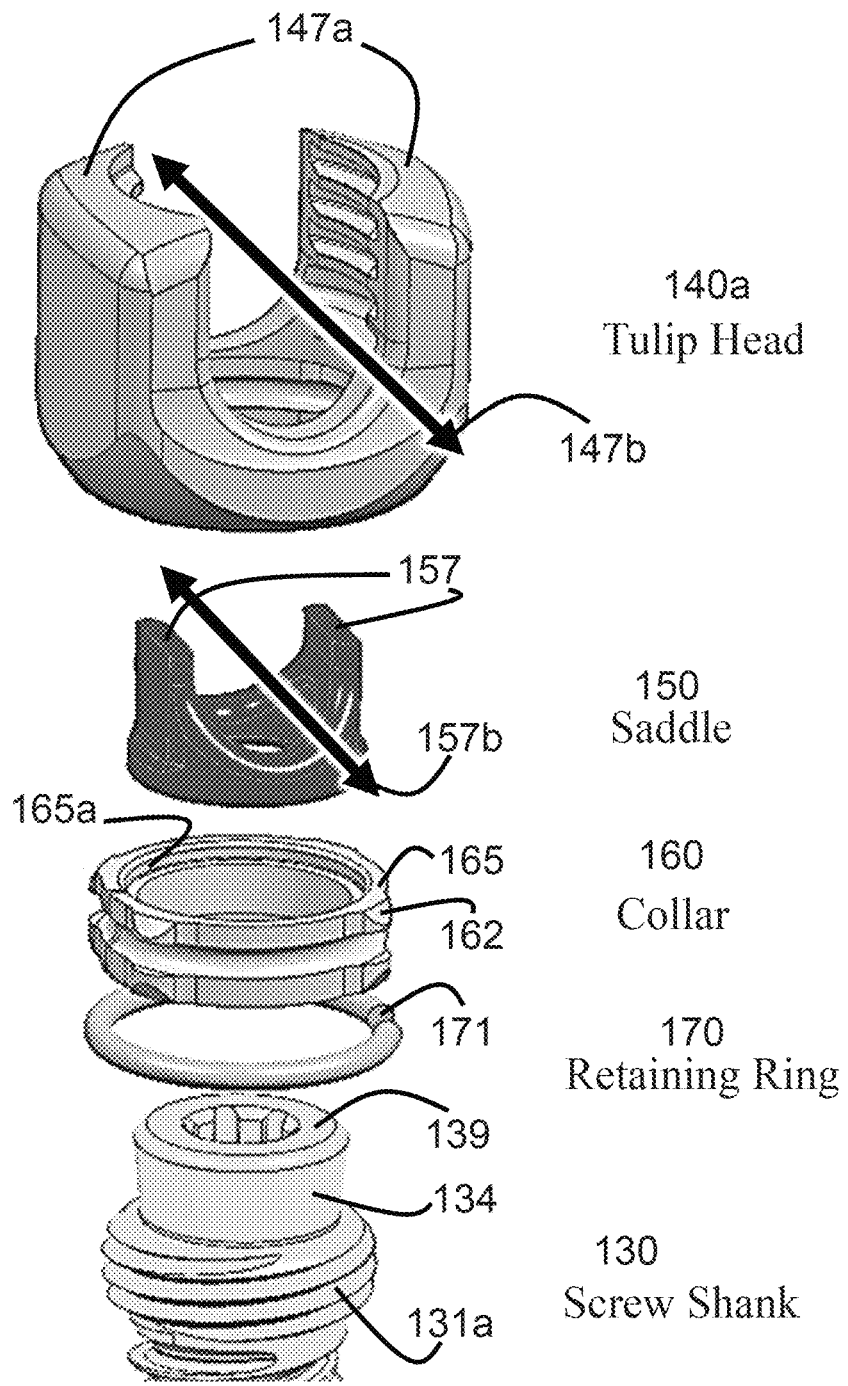
FIG. 14 is an exploded perspective view of a portion of the apparatus of FIG. 12.
Figures 27, 28, 29, 30, 31:
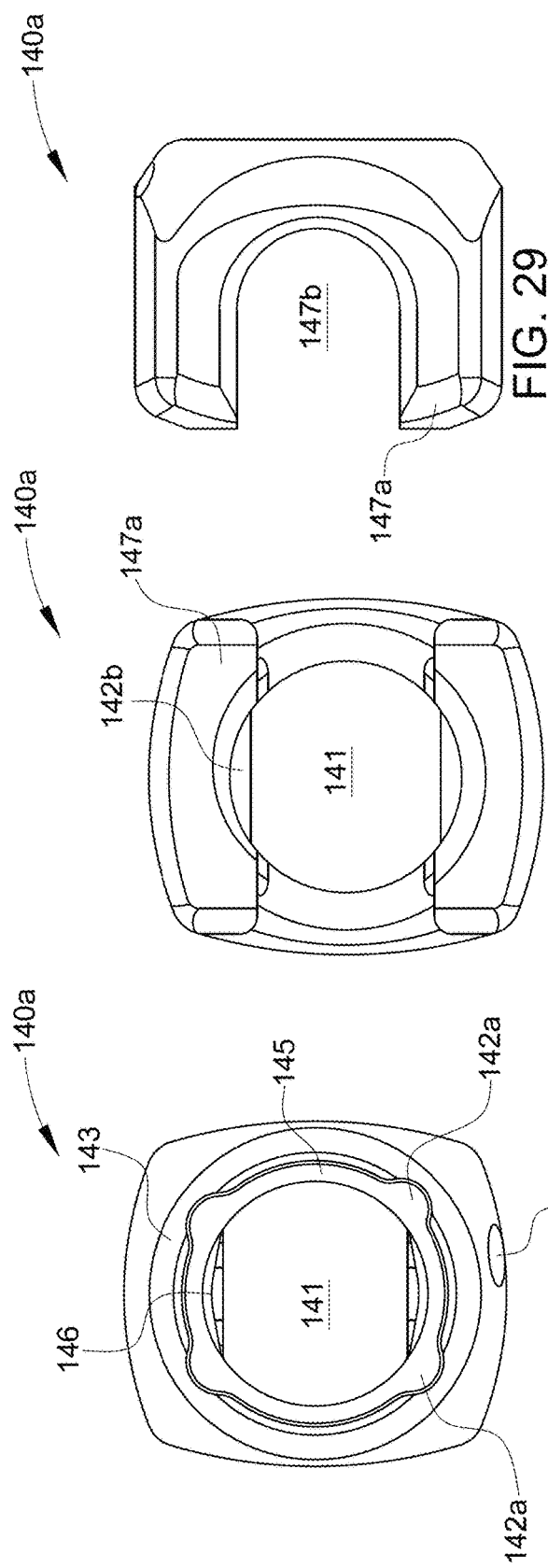
FIG. 27 is a bottom plan view of a portion of the apparatus of FIG. 14.
FIG. 28 is a top plan view of the apparatus of FIG. 27.
FIG. 29 is side elevational view of the apparatus of FIG. 28, and presented orthogonally to FIG. 28.
FIG. 30 is a side elevational view of the apparatus of FIG. 28, and presented orthogonally to FIG. 28.
FIG. 31 is a side, top, perspective representation of the apparatus of FIG. 27.

Components 150 and 160 are loaded into a head 140a through the bottom side 143 (as best seen in FIG. 27). Referring also to FIGS. 13 and 27, it can be seen that a saddle member 150 includes a cylindrical base or pedestal 156, with a pair of upwardly extending arms 157 defining a corridor 157b between them. Referring to FIGS. 12 and 14, it can be seen that the corridor 157b is nested within the tether pathway 147b, with the corridor and the pathway being generally aligned. Preferably, the arms 157 extend at least partly between the threaded portions 147c of body 140a, as shown in FIGS. 5, 13, 33, and 34. In some embodiments, a saddle X50 includes arms X47a having top surfaces X57a, with at least one of these top surfaces X57a coming into contact with a bottom abutting surface X24a of a set screw X24.

In this manner, and referring again to FIGS. 3, 13, 33, and 34, it can be seen that this hard abutting contact between the set screw and the saddle establishes a region in the corridor 157b that has a fixed cross sectional area. In some embodiments, this cross sectional area is approximately D-shaped, although yet other embodiments contemplate any manner of shape created by the abutment of the set screw and at least one of the arms X57. In some embodiments, this cross sectional area is selected to provide a predetermined amount of compression onto a flexible member placed within the corridor. In those embodiments utilizing certain tethering materials fabricated from organic polymers, the predetermined, fixed cross sectional area of the corridor can be less than about fifty percent of the free, uncompressed cross sectional area of the tether, and in still further embodiments less than about thirty percent of the free, uncompressed tether cross sectional area. Those of ordinary skill in the art will recognize that the selection of the geometric features for the fixed cross sectional area of the corridor of the fully assembled head X40 can be selected based on the type of material used for the flexible material (noting for example differences between a wound metallic material and a polymer), as well as for differences in the method of manufacturing (comparing for example loosely packed polymer material vs. densely packed polymer material).

The pedestal 156 of saddle 150 is received within a corresponding saddle pocket 146 of body 140a. Saddle 150 further includes at least one registration feature 152, such as the flat sides shown in FIGS. 18 and 19. A registration feature 152 of saddle 150 is placed proximate to a corresponding, complementary-shaped registration feature 142b of body 140a. By means of the interaction of the saddle and body registration features, rotation of the saddle relative to the body is prevented.

After a saddle is loaded from the bottom into a body 140a, the partially assembled head assembly 140 presents a recess 145 into which a fully expanded, free state split ring collar 160 can be received. In one embodiment, the split ring collar 160 is first coupled to the head 132 of a fastener. In some embodiments, this pre-assembly of the collar onto the fastener may require a spreading tool (not shown) to slightly spread open (preferably elastically) the aperture 161 of the collar to permit the minimum diameter of the tapered aperture of the collar to fit over the top of the tapered outer surface of head 132. After this pre-assembly, the collar returns to its free state and can be placed into the recess 145. The peripheral locating registration features 162 of the collar are received within corresponding, complementary-shaped features 142a near the bottom of body 140a, which resists rotation of the collar relative to the body. In some embodiments, it may be helpful to partially compress the collar prior to insertion of the pocket 145.

Once the collar is inserted, the rotatably coupled head 132 of fastener 130 is able to rotate about the central axis 121. In order to retain the partial assembly of fastener and collar into body 140, a retainer ring or wire 170 (as shown in FIG. 14) can be inserted through a feed opening 149a (FIG. 27), and then slid circumferentially into the locking grooves 149 (of body 140a) and 169 (of collar 160). Referring to FIG. 13, the placement of ring 170 into this combined groove retains the collar and fastener within body 140a. Any attempt to remove the fastener is resisted by this interference fit of the two piece groove with the retainer ring.

Similarly, during attachment of fastener 130 to a bone, a fastening tool (not shown) is received within a pocket in the top of head X32, as can be seen in FIG. 14. This tool is able to extend through the central apertures X51 of saddle member X50 as well as aperture X61 of collar X60. After the fastener X30 has been suitably tightened into the bone, the flexible connector can be placed within a corridor X57b of saddle X50 of an adjacent anchoring device X20. Following that placement, the user attaches set screw X24 onto the arms X47c of the adjacent anchoring device to compress and restrict movement of the flexible connector.

FIGS. 32 and 33 depict a device 220 similar to that of device 120. One difference between the two embodiments can be found in the instrumentation grasping feature 248 located on the outer surface of body 240a. In one embodiment, opposing dovetail grooves are placed on the outer surfaces, through which a complementary-shaped tool can be inserted. However, it is further understood that the various head bodies X40a disclosed herein can include any type of features for coupling to instrumentation, including the overall shape of the plan form of the body.

Figure 34:
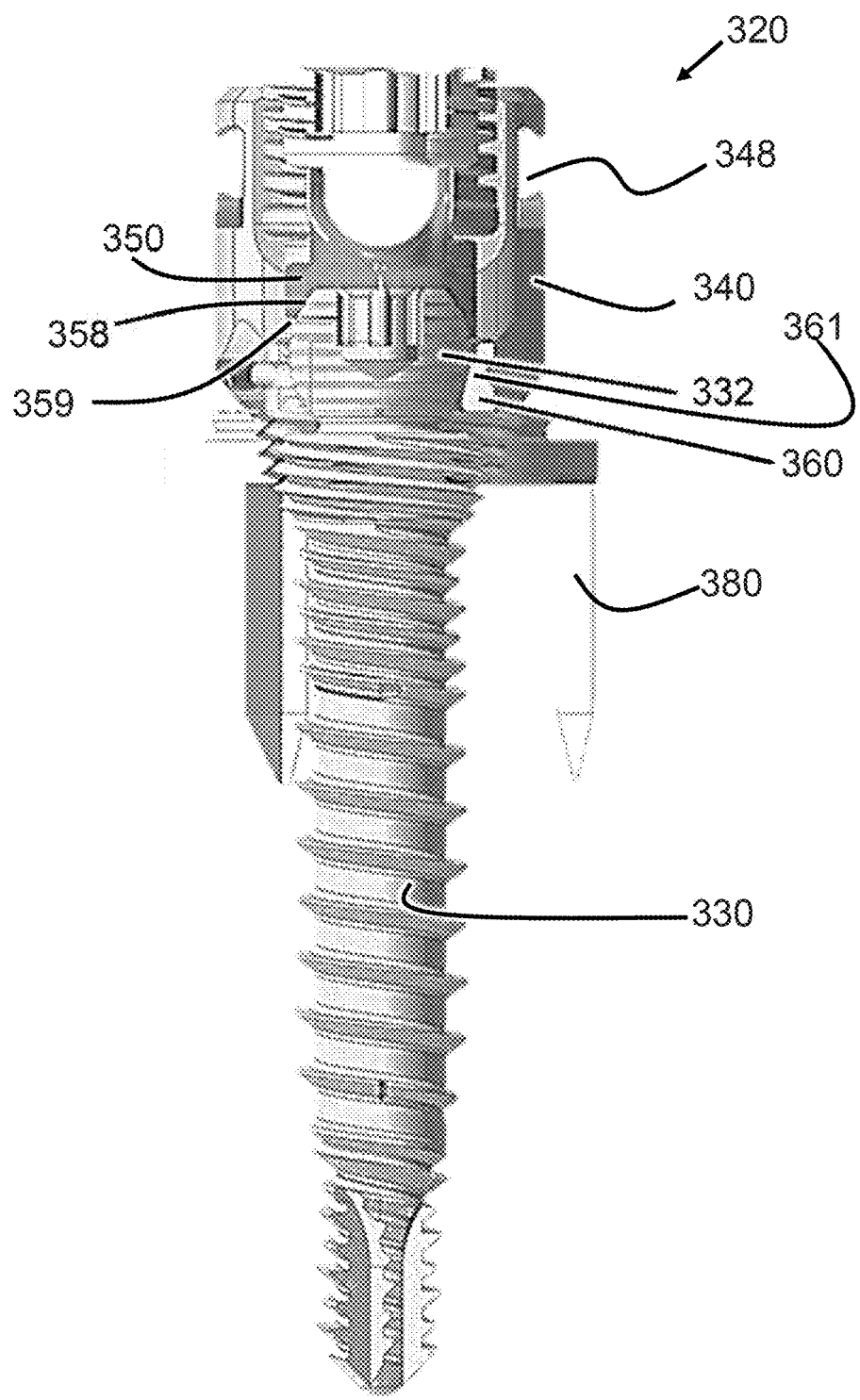
FIG. 34 is a side elevational, CAD surface representation of an anchoring device according to another embodiment of the present invention.
Figure 35:
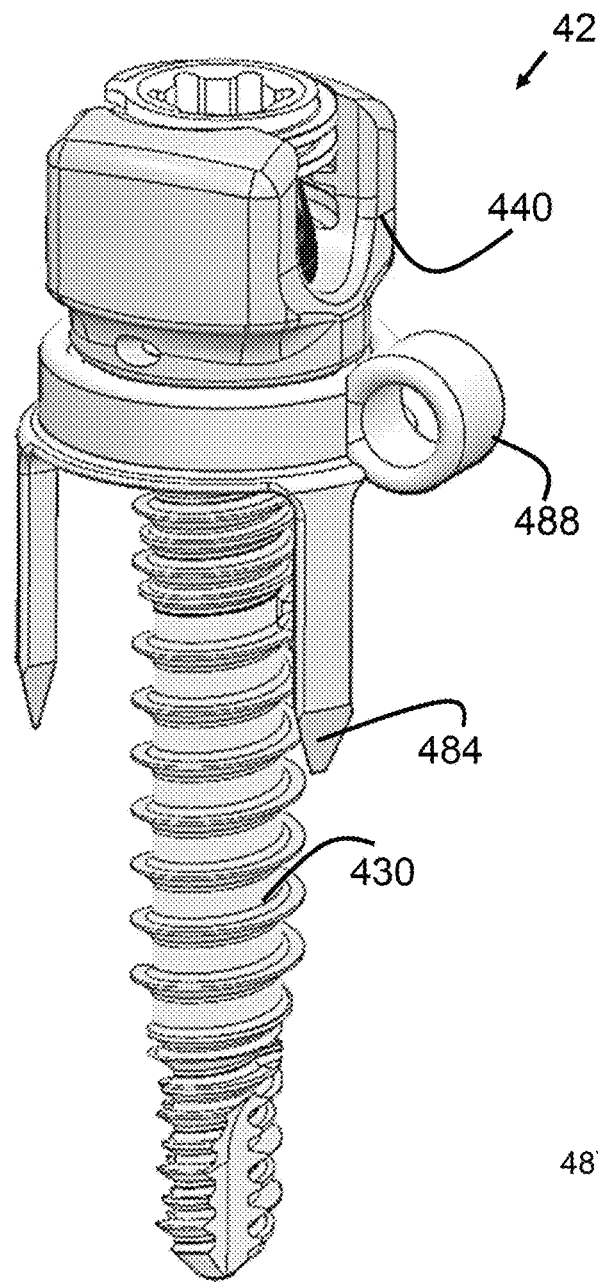
FIG. 35 is a side elevational, perspective, CAD surface representation of an anchoring device according to another embodiment of the present invention.

FIG. 34 shows an embodiment 320 similar to that of device 220, but including a spherically-shaped head 332 that is received within a corresponding spherically-shaped aperture 361 of collar 360. In some embodiments, the base 350 includes a bottom surface 356 that includes spherically-shaped peripheral surfaces. Preferably, head assembly 340 is polyaxially pivotal relative to fastener 330, and able to pivot in three orthogonal dimensions (roll, pitch, and yaw) for improved placement of the corridor 357b.

Figure 36:
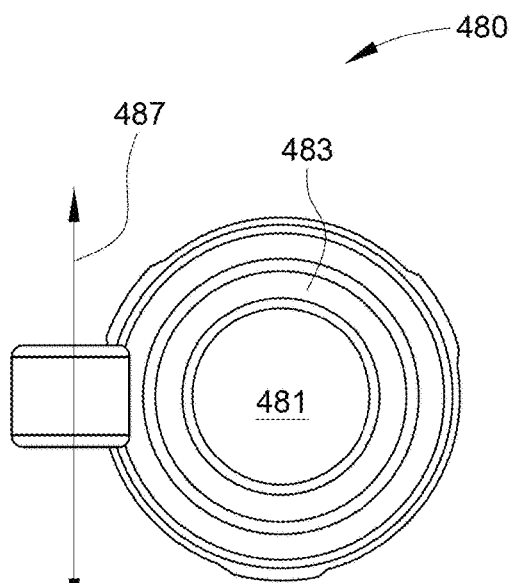
FIG. 36 is a top plan view of a portion of the apparatus of FIG. 35.
Figure 37:
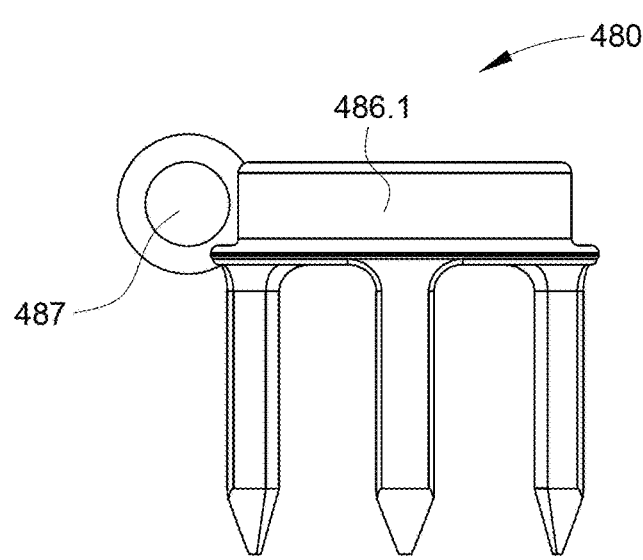
FIG. 37 is a side elevational view of the apparatus of FIG. 36, and presented orthogonally to FIG. 36.

FIGS. 35-38 show various embodiments of an anchoring device 420 according to another embodiment of the present invention. Anchoring device 420 is similar to that of embodiments 20, 120, or 320, except that staple 480 includes an eyelet 488 that preferably extends radially outwardly from one side of outer surface 486.1. Preferably, eyelet 488 defines a central aperture that provides a tether pathway 487. Referring to FIGS. 36 and 37, it can be seen that staple 480 includes a central aperture 481 having an axis that is preferably substantially perpendicular to the tether pathway 487. However, it is understood that the eyelet can be oriented in any manner from the outer surface of the staple, and further the tether pathway can have any angular orientation relative to the central aperture of the staple. It is understood that the interface between the staple and the fastener can be of any type described herein.

Figure 38:
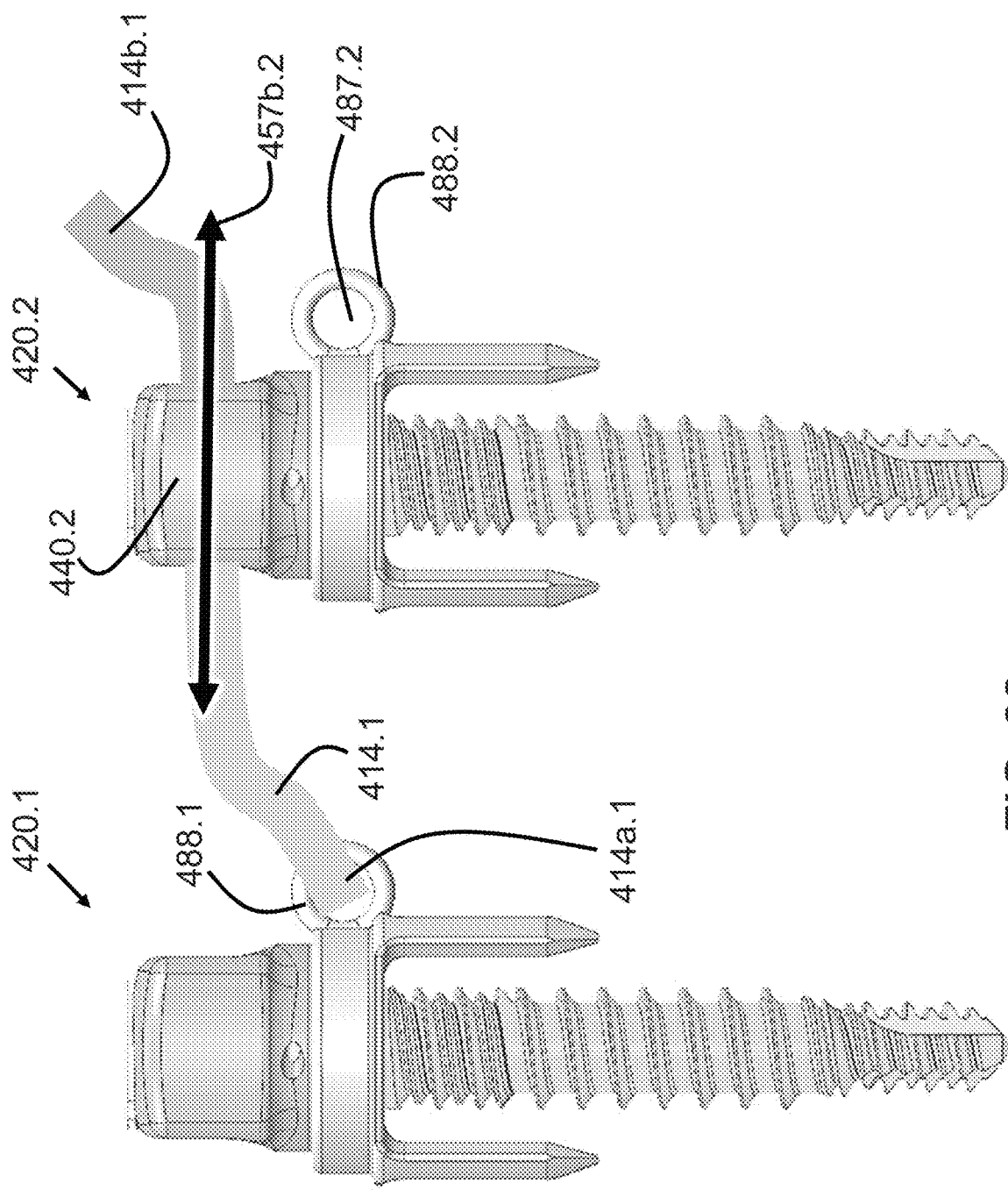
FIG. 38 shows a plurality of the devices of FIG. 35 interconnected by a flexible connection.

FIG. 38 shows a pair of devices 420.1 and 420.2 that are adjacent to one another. In one embodiment, a loop 414a.1 extends around eyelet 488.1 and through aperture 487.1. The remainder of the section of tether 414.1 extends through a corridor 457b.2 of adjacent anchoring device 420.2, and is frictionally captured within head 440.2. The free end 414b.1 of tether 414.1 extends loosely out from head 440.2. It is further understood that in some embodiments an eyelet such as eyelet 480.2 can serve as a guiding pathway for a section of tether that has one end connected to a first tethering device (not shown), with the remainder of the tether extending out of eyelet 488.2 to a second tethering device (not shown), such that the tether extends through the eyelet of an anchoring device, but is not anchored to the tether corridor of that same device.

FIGS. 39-49 show various aspects of a bone anchoring mechanism 520 that has some similarities to anchoring mechanism 320 previously described, and further to other anchoring members X20 presented herein, but with one or more different components or functions as will be described.

Referring first to FIGS. 39-43, it can be seen that bone assembly 520 in one embodiment includes a head assembly 540 receiving within it a releasably coupled and preferably separable saddle member 550. The body 540a of head assembly 540 is preferably pivotally coupled to the rounded head 532 of a bone fastener 530. In some embodiments, the head 532 of fastener 530 is preferably pivotally captured within the base 540b by a collar 560.

Figures 39, 40:
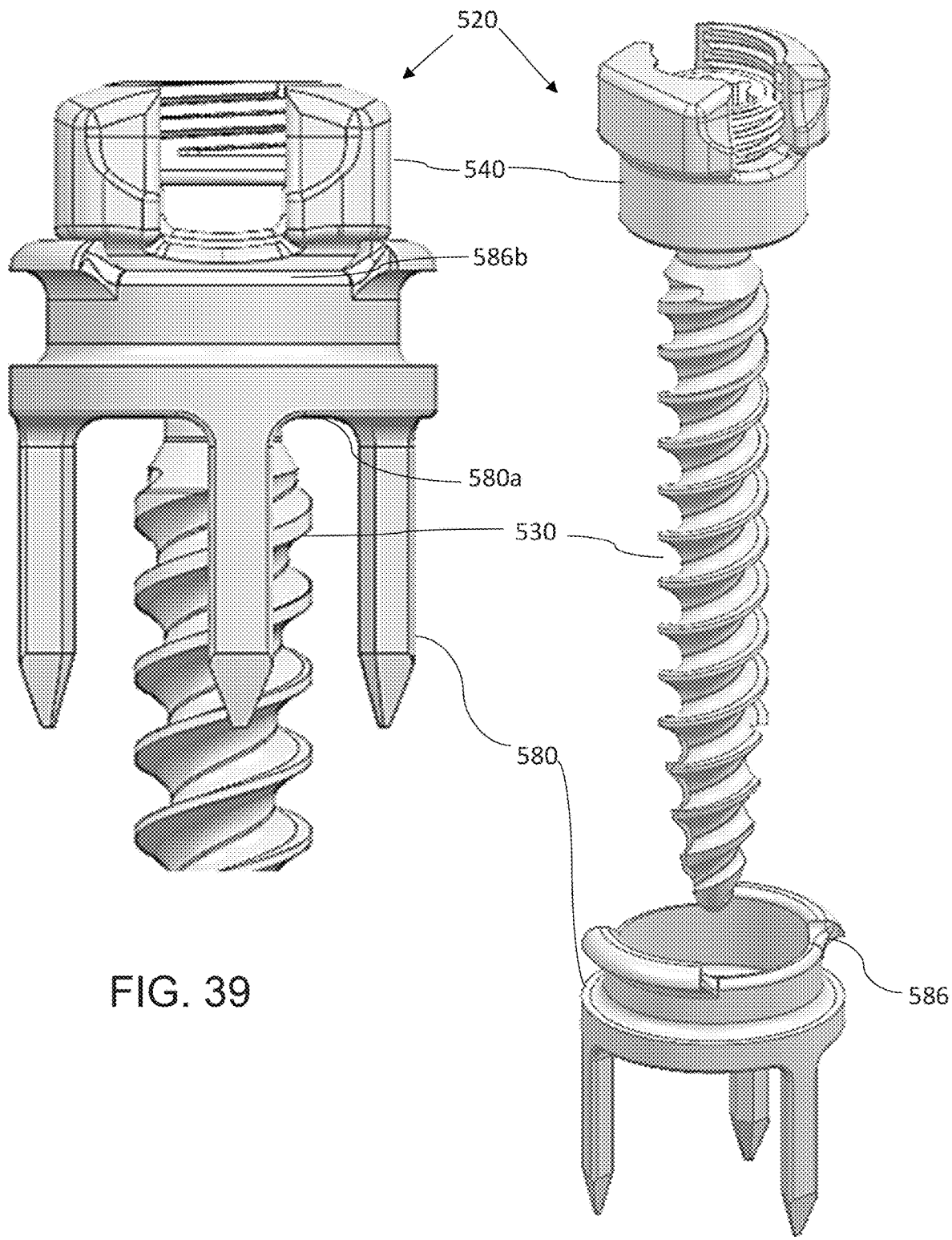
FIG. 39 is a CAD generated side elevational partial representation of a bone anchor assembly according to yet another embodiment of the present invention.
FIG. 40 is a partially exploded view of the apparatus of FIG. 39.
Figure 43:
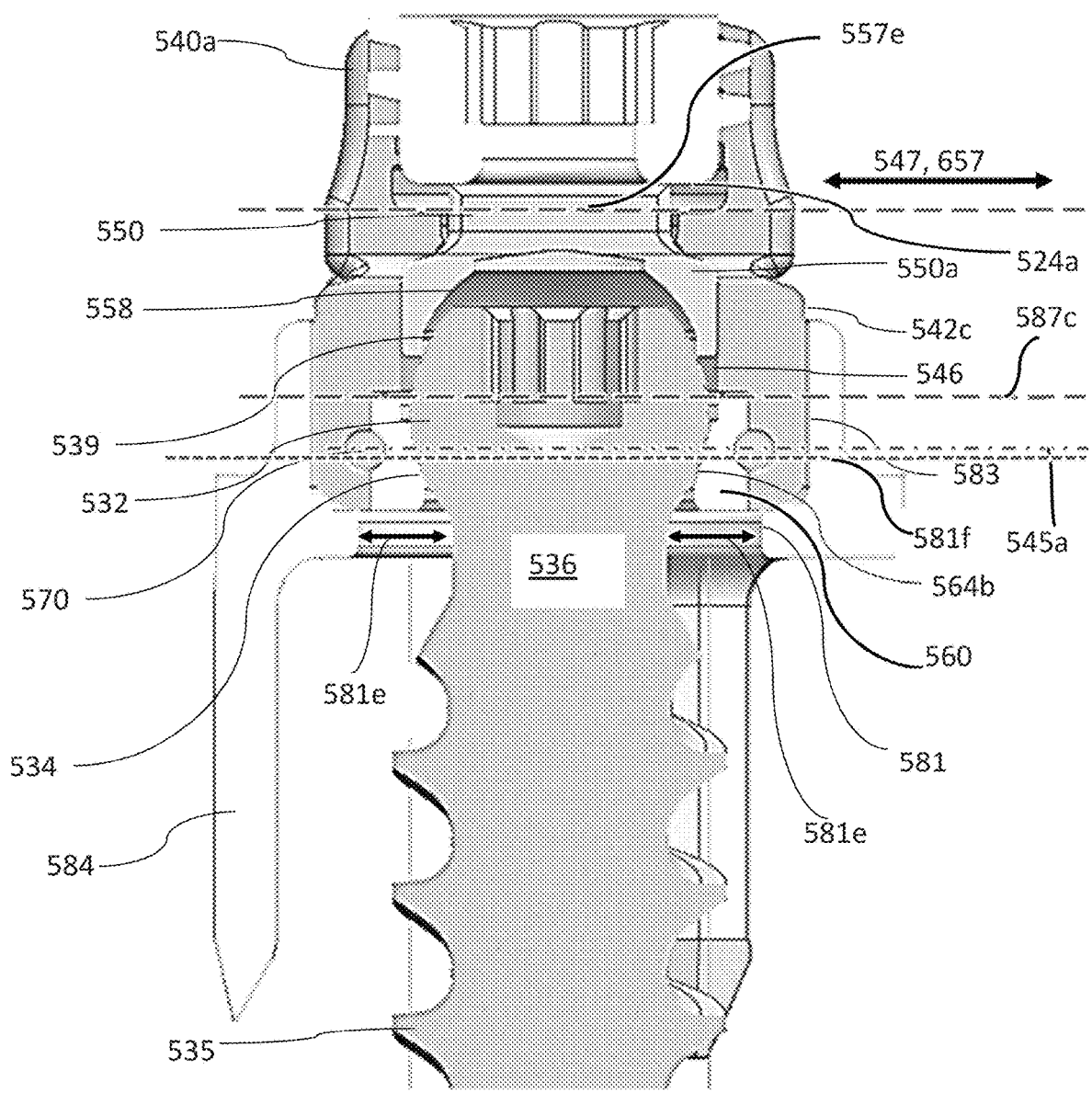
FIG. 43 is a cutaway view of the apparatus of FIG. 39.
Figure 44A:
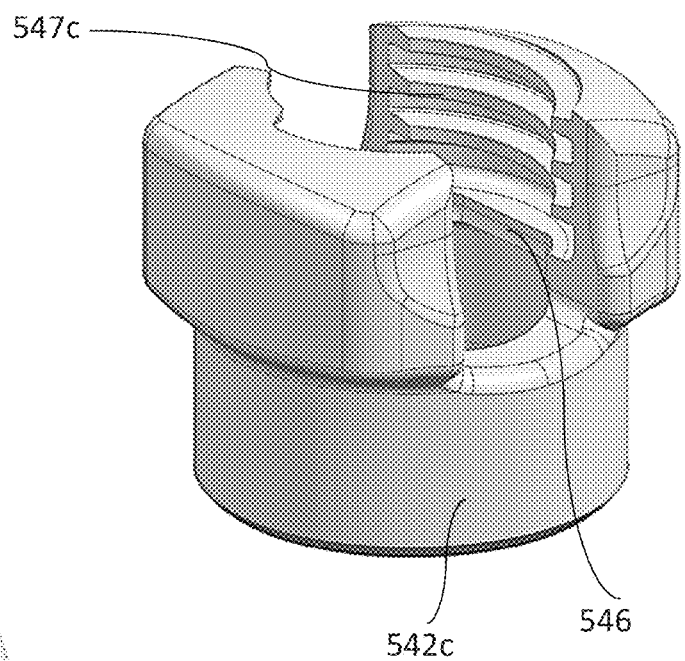
FIG. 44A is a top, side perspective representation of a component of the apparatus of FIG. 39.
Figure 44B:
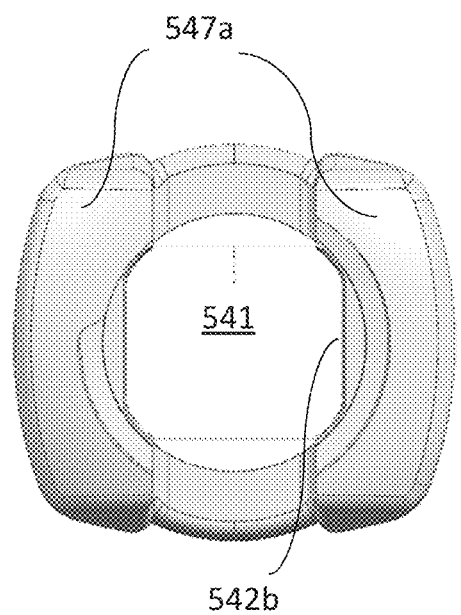
FIG. 44B is a top plan view of the apparatus of FIG. 44A.
Figure 44C:
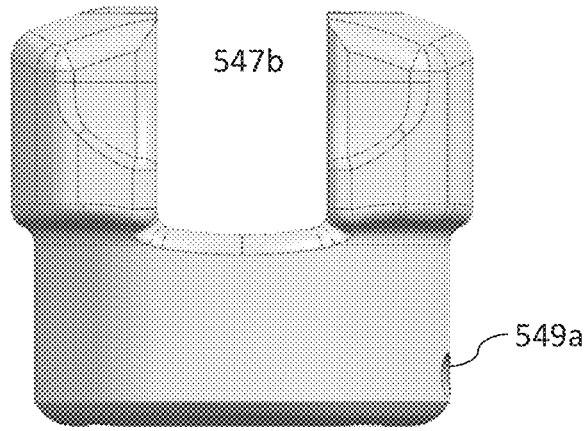
FIG. 44C is a side elevational view of the apparatus of FIG. 44A, and orthogonal to FIG. 44B.
Figure 44D:
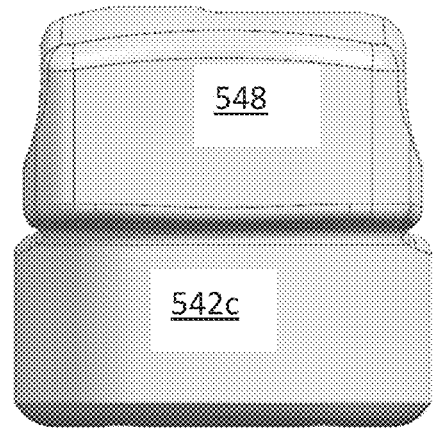
FIG. 44D is a side elevational view of the apparatus of FIG. 44A, and orthogonal to the FIG. 44C.
Figure 47A:
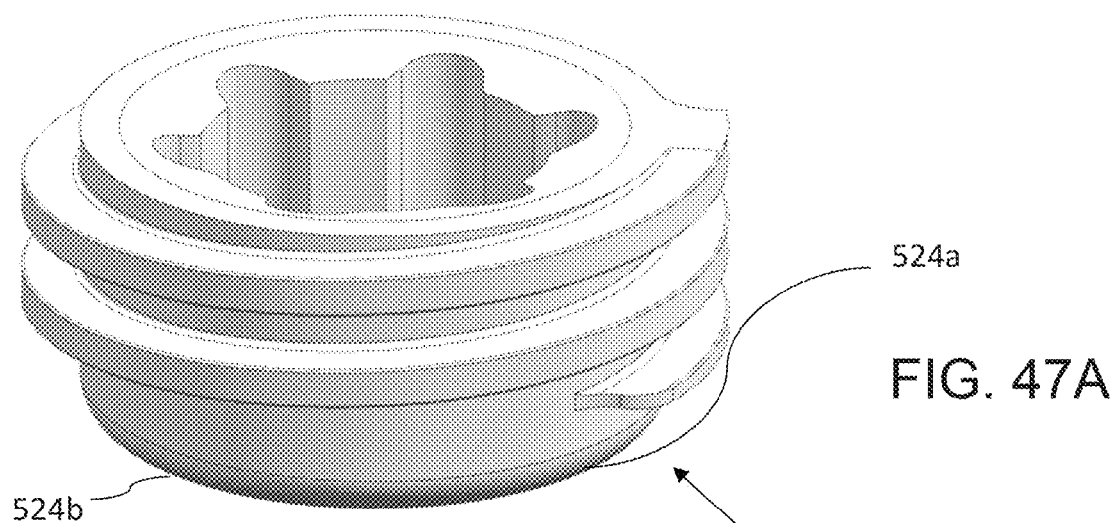
FIG. 47A is a side, top perspective representation of a portion of the apparatus of FIG. 39.
Figure 47B:
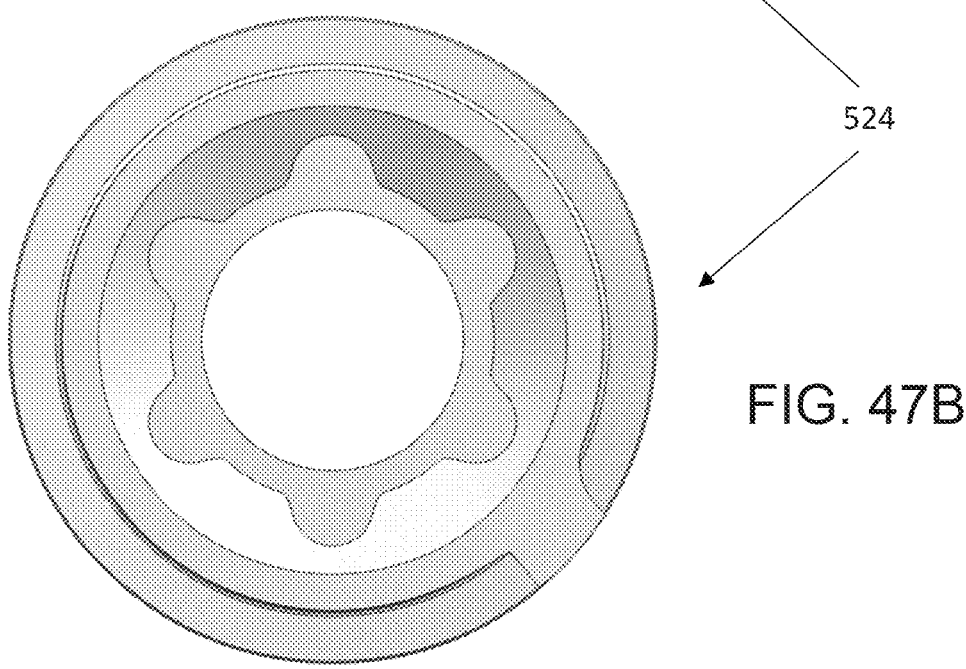
FIG. 47B is a top plan view of the apparatus of FIG. 47A.
Figure 48A:
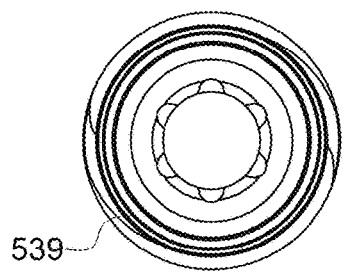
FIG. 48A is a top plan view of portion of the apparatus of FIG. 39.
Figure 49A:
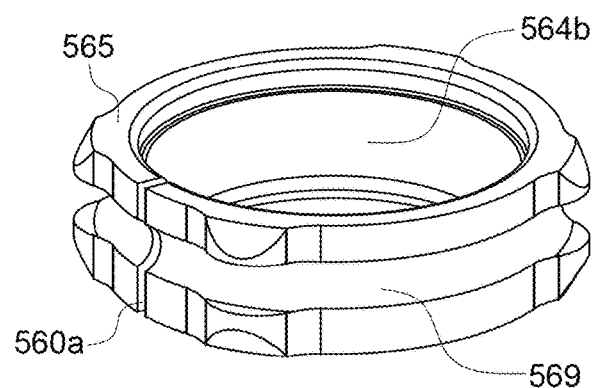
FIG. 49A is a top, side perspective representation of a component of FIG. 39.
Figure 48B:
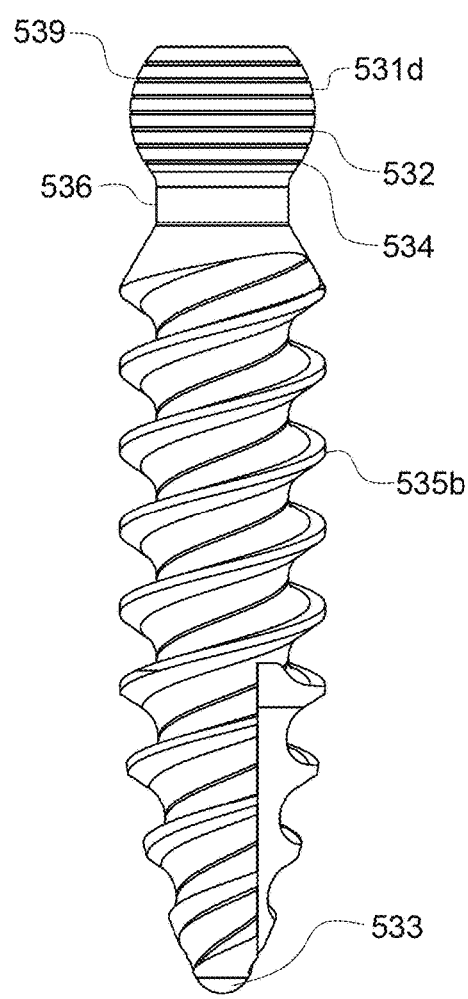
FIG. 48B is a side elevational view of the apparatus of FIG. 48A, and presented orthogonally to FIG. 48A.
Figure 49B:
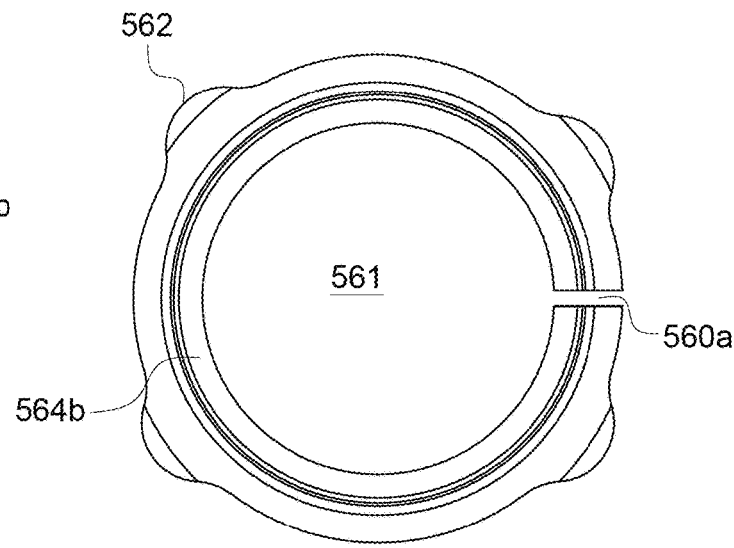
FIG. 49B is a top plan view of the apparatus of FIG. 49A.

Referring to FIGS. 39 and 43, it can further be seen that anchor 520 includes a staple 580 having a base 580b that defines a head receiving pocket 583. Referring to FIG. 43, it can be seen that base 540b of head assembly 540 includes an outer diameter 542c and a bottom surface 543 which are received within pocket 583. In some embodiments, the body 540a is a close fit within pocket 583, although with sufficient clearance to permit limited relative rotation and limited relative radial movement.

Figures 41, 42:
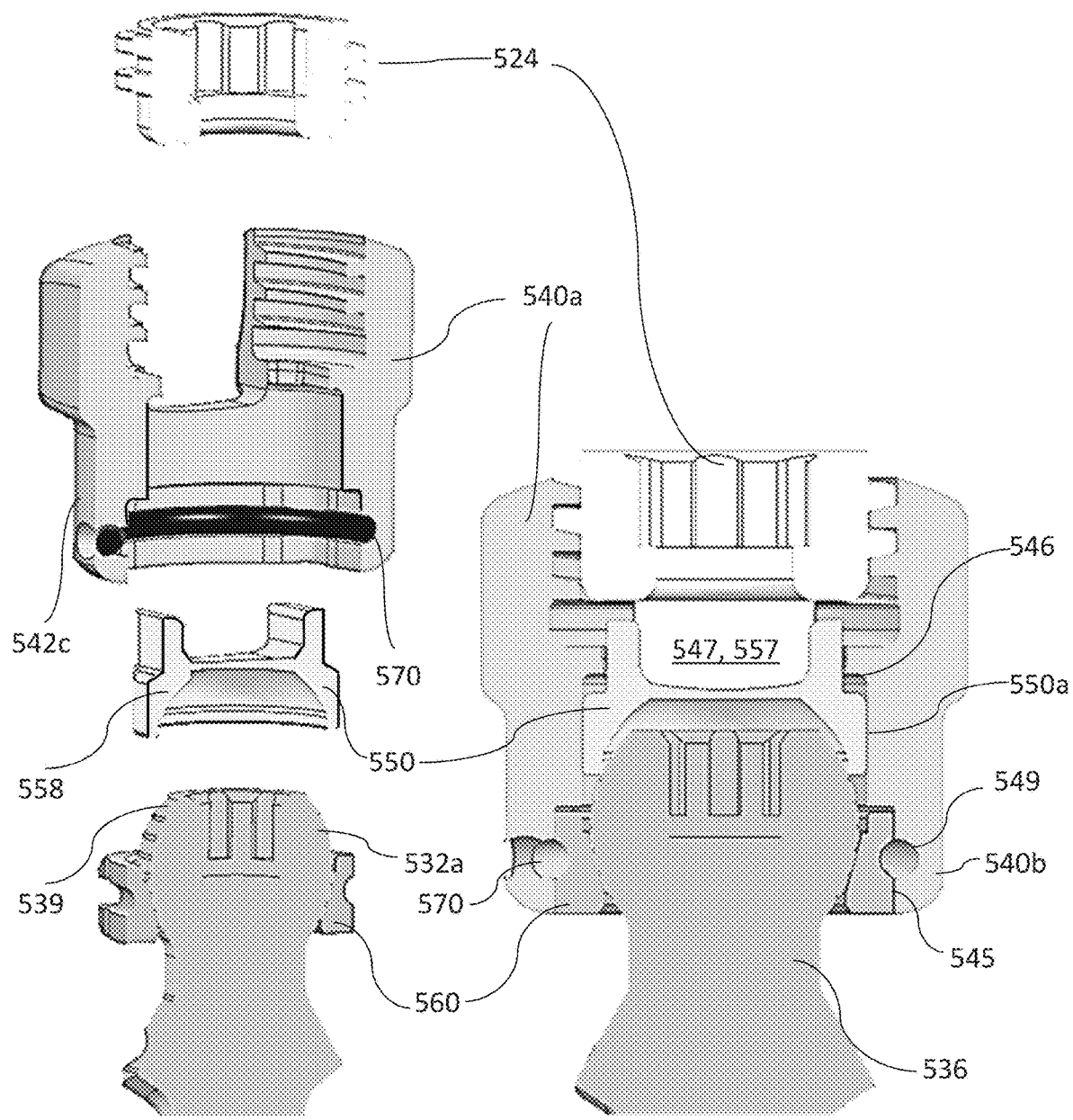
FIG. 41 is an exploded cutaway drawing of the apparatus of FIG. 39.
FIG. 42 is an assembled representation of the apparatus of FIG. 41.

In some embodiments, head 532 of fastener 530 is of the polyaxial type, having a head is that is rounded so as to permit the head to pivot in two orthogonal directions relative to head assembly 540. As best seen in FIGS. 42 and 43, it can be seen that that in some embodiments on the underside of head 532 the rounded (or preferably spherical) collar interface 534 rests against a complementary rounded (or preferably spherical) fastener head interface surface 564b of collar 560. The top rounded (or spherical) surface of head 532 is received at least partially within a complementary rounded (or preferably spherical) surface 558 of saddle 550. The bottom surfaces 559 of saddle 550 are received and sandwiched between the surface of head 532 and the inner diameter of saddle pocket 546. It can be seen in FIGS. 42 and 43 that as long as the head assembly 540 is loose (i.e., set screw 524 is not tightened) then bone fastener 530 can exhibit limited two dimensional pivoting relative to head assembly 540.

Referring to FIG. 43, it can be seen that in some embodiments the fastener 530 includes a reduced diameter neck 536 between the larger rounded or spherical head 532 and the threaded shank 535. When the assembly of head assembly 540 and fastener 530 are placed within pocket 583 of staple 580, there is a radial gap or clearance 581e between the outer diameter of the neck 536 and the inner diameter 581 of the staple aperture. In this manner, the staple aperture does not limit pivoting. Instead, the limit to relative pivoting motion between anchor 530 and staple 580 is established by placement of the projections 584 in some circumstances. However, the present invention further contemplates those embodiments in which the threaded shank 535 of fastener 530 is able to fit between adjacent projections 584, such that the pivoting motion is limited by contact between the threaded shank and aperture 581, or as a further alternative the pivoting motion is limited by contact between the threaded shank and projections 584.

FIG. 43 shows apparatus 520 when set screw 524 has been tightened within the threaded receptacle of head 540a. The bottom surface 524b includes at least one portion 524a that is adapted and configured to abut with a corresponding top surface 557a of saddle 550. However, yet other embodiments of the present invention contemplate any manner of contact between a set screw X24 (or other fastener) and any surface of saddle X50.

This contact between the set screw and the saddle compresses saddle 550 within pocket 546 until the bottom surface 559 wedges between the rounded, top surface of fastener 530 and the inner diameter of pocket 546. This compressive force further pushes the bottom of head 532 against the inner surfaces 564b of collar 560. Since collar 560 is locked and prevented from vertical motion by retainer 570 within grooves 549 and 569, the tightening of set screw 524 establishes a lockup of head assembly 540 relative to fastener 530.

In those embodiments the present invention incorporating a rounded or spherical interface, the centerline of the head assembly 540 can be nonparallel relative to the centerline of fastener 530. However, as can be seen in FIG. 43, even though there can be a nonparallel relationship between head assembly 540 and fastener 530, because of the placement of outer diameter 542c within head receiving pocket 583, head assembly 540 has a fixed (preferably coaxial) angular relationship relative to staple 580. Thus, any angular offset between the head assembly and the bone fastener is likewise an angular offset between the bone fastener and the staple.

Yet another difference between apparatus 520 and some of other bone anchors X20 herein is the shape of the corridor 557 of saddle 550. Referring to FIGS. 45A and 45B, it can be seen that the corridor 557 has a height 557h that is less than the width 557w, such that the corridor 557 has in some embodiments a generally rounded rectangular shape. In those embodiments in which the flexible connector received within the corridor is a flat tape, the retention of that flat tape can be achieved within corridor 557 with an improved distribution of tensile, compressive, and contact stresses, thus making the flexible connector less susceptible to failure. Still further, it can be seen in FIGS. 45B and 45C that the overall height of the arms 557b are shorter than the saddle arms or saddle member 350. Referring back to FIG. 39, it can be seen that assembly 520 in some embodiments has a lower overall profile between the bone contacting surface 580a and the top surface of either the body 540b or the top of the set screw 524.

A still further difference of bone anchor assembly 520 relative to bone anchor 320 is with regards to staple 580. Referring to FIGS. 39 and 46, it can be seen that staple 580 includes a base 580b that defines within it a circumferentially extending groove 586 that is adapted and configured to receive within it a loop of flexible connector within a tether pathway 587. Preferably, this tether pathway 587 has a circumferential extent 587a that extends at least partially (and preferably completely) around the body of staple 580. In some embodiments, the tether pathway 587 extends for a transverse distance 587b that is preferably greater than the diameter of the flexible connector. In this manner, the loop of flexible connector can move transversely (i.e., vertically as shown in FIG. 46B) within the tether pathway. This transverse clearance permits the flexible connector to be placed (or to self-locate) in a position of lower stress during tensioning of the flexible connector.

In some other embodiments, staple 580 further includes an overhanging circumferential lip 586a that is adapted and configured to discourage any unseating of the flexible connector from pathway 587. In some embodiments, the radially outward overhang of this lip 586a relative to the outer diameter of groove 586 is preferably equal to or more than about one-half of the thickness of the flexible connector.

In still further embodiments, the overhanging lip 586a has a limited circumferential or angular extent. Referring to FIG. 46A, it can be seen that in one embodiment the overhanging lip 586a is located on two generally opposite sides of aperture 581. In between these sectors 586a is a sector 586b in which the lip has been relieved or removed. Although what is shown is a complete removal of the lip in FIG. 46B, it is understood that this relieved section can include some semblance of the lip, such as with reduced overhang. It has been found that these relieved sections assist in reducing the installed stress concentrations within the flexible connector. In those embodiments in which the flexible connector includes a free end that extends out of the plane of the pathway 587, this portion of the flexible connector can move out radially away from the staple body with less stress than those embodiments not having the relieved section.

Figures 55A, 55B:
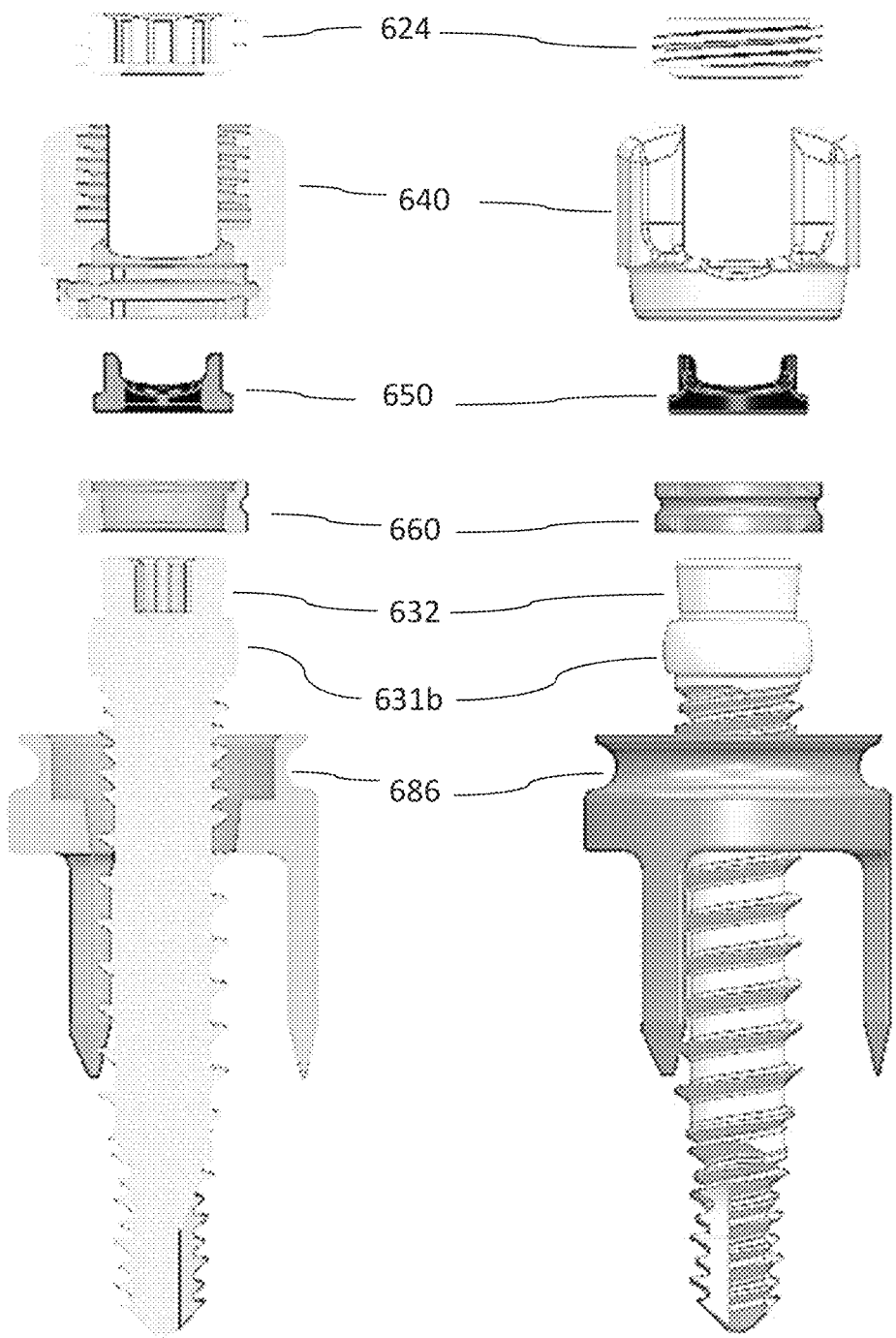
FIG. 55A is a side elevation, exploded, cross sectional view of the apparatus of FIG. 54A.
FIG. 55B is an exploded view of the apparatus of FIG. 54A.
Figure 56:
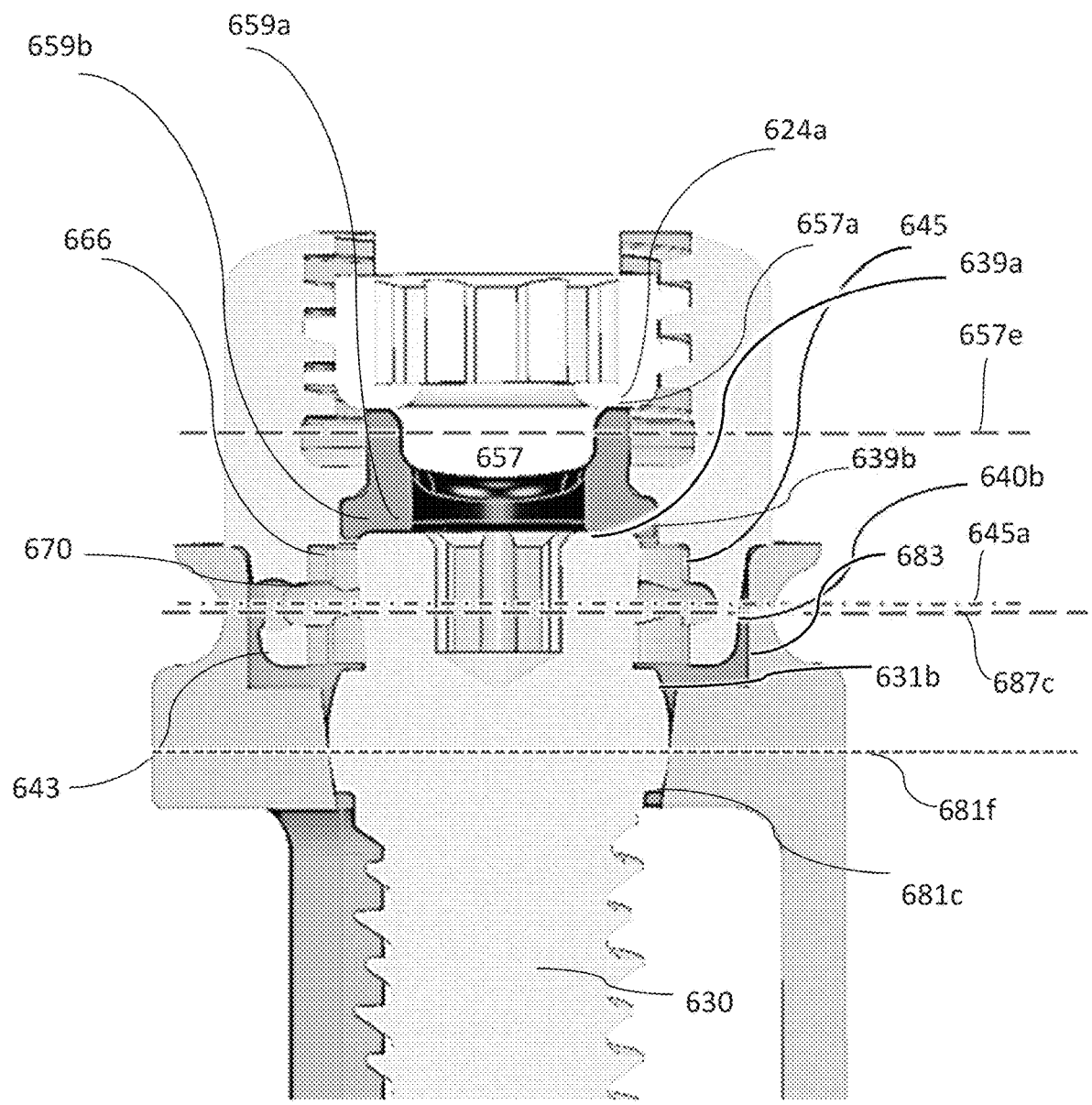
FIG. 56 is a side elevational, cross sectional view of the apparatus of FIG. 54A.

FIGS. 54-56 depict various aspects of a bone anchoring assembly 620 according to another embodiment of the present invention. In some respects, bone anchor 620 is similar to anchor 20 previously described, except for some differences in the shape of the components and certain functions that will now be described.

Referring to FIGS. 55A and 55B, it can be seen that saddle member 650 has a corridor 657 between arms 657*a* and the bottom of set screw 624 that has a cross sectional shape similar to that described for bone anchor 520. However, as best seen FIG. 56, saddle member 650 interfaces with the head 632 of fastener 620 in a manner more similar to that of saddle member 20. Preferably, fastener 630 includes a generally smooth, rounded (or preferably spherical) interfacing surface 631*b* that is adapted and configured to contact the preferably conical surface 681*c* of staple 680. In yet another difference, it can be seen that the bottom, fastener interface surface 659 of saddle 650 includes a relief pocket and outer ridge that receive within them the top surface of fastener 630. FIG. 56 shows that the upper, top surface 639 of the fastener head is preferably in contact with the underside of pocket 659*a*, and further that the rounded outer shoulder of the fastener head is preferably in contact with a portion of ridge 659*b*.

A still further difference between bone anchor 20 and bone anchor 620 is with regards to the relative placement of the tether pathway of the staple body relative to the point of fastener contact of the staple body. Referring to FIG. 56, staple 680 includes a pathway groove 686 having a tether loop load line 687*c* that extends midway across the transverse extent of the tether pathway. It can be seen that the plane of contact 681*f* between fastener surface 631*b* and staple interface 681*c* is preferably located below plane 687*c* through which the load from the tether loop is applied to bone anchor 680.

In bone anchor X20, the frictional retention of the flexible connector within the corridor X57 establishes a line X57*e* along which the tension load can be considered to be acting, and in some embodiments this line passes through the centroid of the defined cross sectional area of corridor X57 (it being understood that this line passing through a centroid of an area lies within a corresponding plane that passes through a corresponding volume within the corridor). Likewise, the frictional retention of the flexible connector within the pathway X87 establishes a line X87*c* along which the tension load of the loop can be considered to be acting, and in some embodiments this line passes through the centroid of the defined cross sectional area of groove X86. Still further, in those embodiments in which the head body X40*a* is retained by a collar and retainer X60 and X70, respectively, that the head X32 of fastener X30 is retained relative to body X40*a* along a line of contact X45*a*. In some of the embodiments shown herein, a loop of tether X14*a* passes a load to a staple or bone anchor X80 that is pivotally coupled to the head of a fastener. In FIG. 5, it can be seen that the application of the loop tension from load line 87*c* is substantially coincident with the transfer of load line 81*f* between fastener 30 and staple 80. By comparison, the application of the loop tension from higher load line 687*c* load to lower contact plane 681*f* shown in FIG. 56 applies a torque or moment from the tether loop to the staple 680.

Various embodiments of the present invention contemplate different relative placements of loadings along lines X57*e*, X87*c*, X81*f*, and X45*a*, which correspond to different moment arms applied to one bone anchor assembly X20 from another bone anchor assembly, and from a bone anchor or staple X80 to the fastener X30, which can be useful in some embodiments relative to considerations of torque applied to different components of assembly X20. Further, different relative placements of load lines X57*e*, X87*c*, X81*f*, and X45*a*, also correspond to geometric and spatial aspects of a bone anchor assembly X20, which can be useful in some embodiments relative to considerations of placement within the body of the person receiving the implantation.

These different relative placements of load application lines or planes can be seen by comparing FIGS. 5, 43, and 56. For example, referring to the center of the tether pathway X87*c*, it can be seen that in FIG. 3, the plane of contact 45*a* between the fastener and the head is above load line 87*c*. In FIG. 43, it can be seen that the load line 545*a* is located below the center 587*c* of the tether pathway. In FIG. 56, it can be seen that the center 687*c* of the tether pathway and the plane of contact 645*a* are roughly coincident. Therefore, the application of a torque between tether load lines X87*c* and head to fastener line X58*a* result in the application of a torque in one direction in FIG. 5, and the application of a torque in the opposite direction in FIG. 43. In FIG. 56, the lines are roughly coincident, meaning that the applied torque is relatively low. A still further difference can be seen with regards to the relative spacing between the plane of contact X81*f* between the fastener surface and the staple interface relative to load line X87*c*, the center of the tether contact area of the staple. In FIG. 5 it can be seen that load paths 87*c* and 81*f* are generally coincident. In FIGS. 43 and 56 it can be seen that the load line X81*f* is located below load line X87*c*, such that the application of tension in the tether applies a torque between the components.

Referring to FIG. 56, the line 657*e* of the center of the tether pathway is spaced apart from and located above the plane of contact 645*a* between the fastener and the head. Further, the load lines 687*c* and 645*a* are roughly coincident. In bone anchor 20, and briefly referring to FIG. 5, it can be seen that the central plane 87*c* of the tether pathway 87 of the staple 20 is spaced apart from and beneath the plane of contact 45*a* between fastener 30 and head 640. With the close relationship of load paths 645*a* and 687*c* as shown in FIG. 56, it is possible to bring the tether pathway 687 closer to tether corridor 657. This reduced vertical offset between the two tether pathways can be useful in those embodiments in which a tether within the corridor 657 of a first anchor is coupled to the tether pathway 687 of an adjacent anchor. By reducing this vertical spacing change from one anchor and one lower pathway to an adjacent anchor and a higher pathway can assist in reducing localized stresses within the flexible connector, such as those stresses due to abrasion. Further, the reduced vertical offset between the tether pathways results in a lower moment between the two adjacent anchors, since this vertical offset acts as a moment arm. However, in the relative orientations shown in FIG. 5, different loadings can be applied to the interface between head 40*a* and fastener 30, since the loading along 57*e* is above 45*a*, and the loading along 87*c* is below 45*a*. A still further arrangement of load lines 557*e*, 587*c*, and 545*a* can be seen and appreciated in FIG. 43.

FIGS. 57-65 show various aspects of a bone anchor 720 according to another embodiment of the present invention. It will be seen that some aspects of bone anchor 720 are similar to that of anchor 20 previously discussed. Although bone anchor 720 is not shown with a corresponding staple, it is understood that such a staple X80 of any type shown herein can be used with anchor 720.

Figures 57, 58:
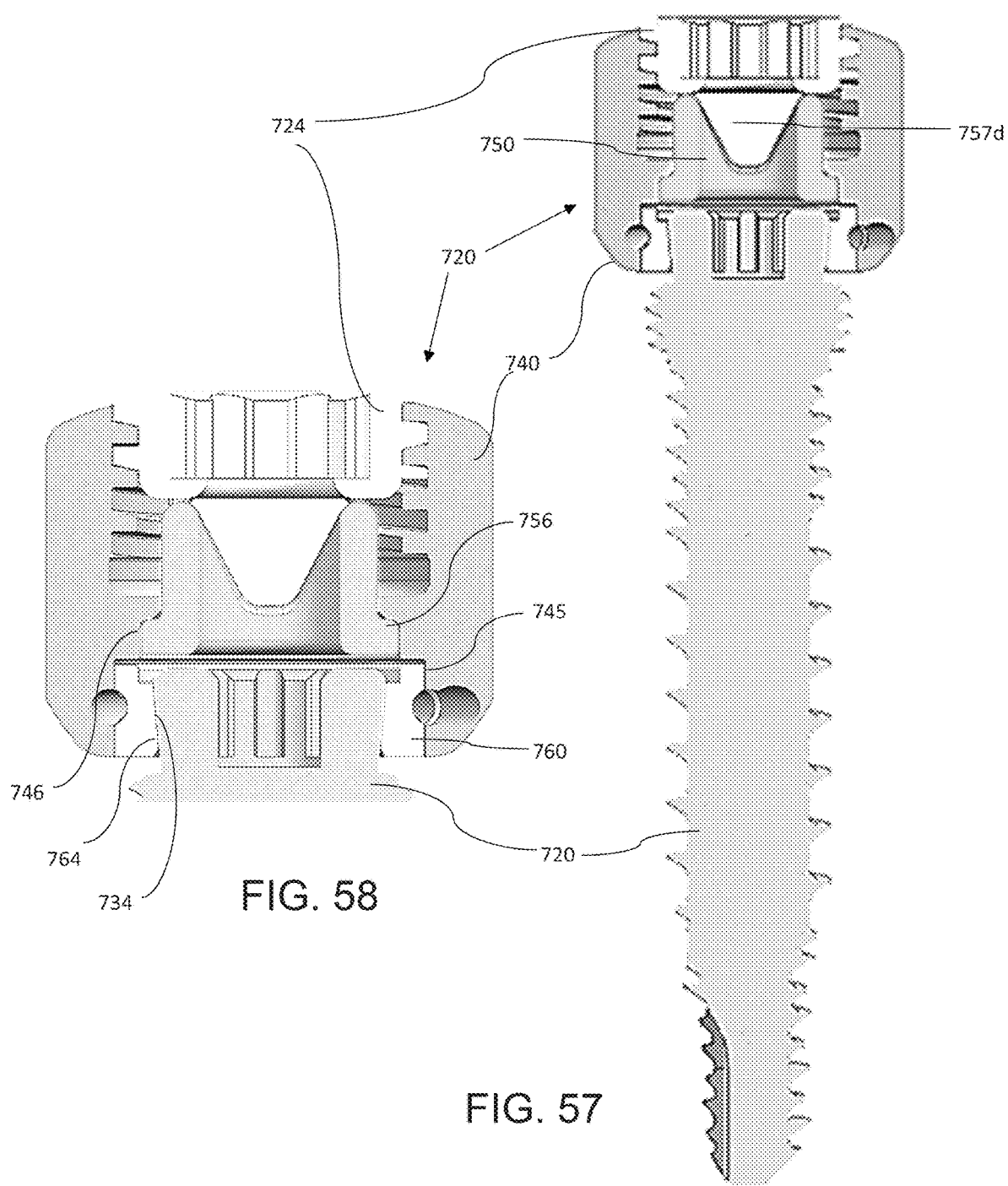
FIG. 57 is a CAD generated side elevational, cross sectional view of a bone anchoring assembly according to another embodiment of the present invention.
FIG. 58 is an enlargement of a portion of FIG. 57.

Comparing FIGS. 58 and 5, it can be seen that in one embodiment both the head 732 of fastener 730 includes a collar interface 734 that is preferably tapered. Likewise, collar 760 includes a complementary tapered inner surface 764 that is adapted and configured for frictional contact with surface 734, thereby locking the fastener relative to both collar 760 and the body 740a. However, although what has been shown and described includes a tapered fastener within a tapered collar, it is understood that yet other embodiments contemplate any of the fastener and collar interfaces described herein, including rounded or spherical fastener head surfaces located within collars with tapered inner surfaces, and further convex rounded or spherical fastener heads placed within concave rounded or spherical collar surfaces.

A frictional locking between the collar and fastener head occurs when set screw 724 is fully tightened within the threaded receptacle of head assembly 740, such that the bottom surface of the set screw contacts one or more of the arms (or other features) of saddle member 750. This tightening drives saddle member 750 downward such that the bottom surface of the saddle member contacts the top of the fastener head. This contact is not shown in FIG. 58.

Comparing FIGS. 57 and 5, it can further be seen that saddle member 750 includes a corridor 757d that has a converging shape from the top (in contact with the bottom of the set screw) to the bottom (proximate to the fastener head). In contrast, tether pathway 57 of FIG. 5 is partly straight at the entrance, with the sides coming together with a rounded bottom surface. In some embodiments, the tether corridor 57 has a general U-shape, whereas corridor 757d has a general V-shape. In some embodiments, this general V-shape is more effective at pinching and frictionally retaining the tether within the corridor, as compared to a general U-shape. In yet other embodiments, the general U-shape may be more effective at reducing peak contact stresses within the frictionally captured portion of the flexible connector within the corridor.

Referring to FIG. 60, it can be seen that in some embodiments the arms 757b are angled as indicated by converging angle 757d, such that the cross sectional area of the corridor 757 reduces as the flexible connector is pushed downward between the arms 757b by the tightening of the set screw.

Figure 59A:
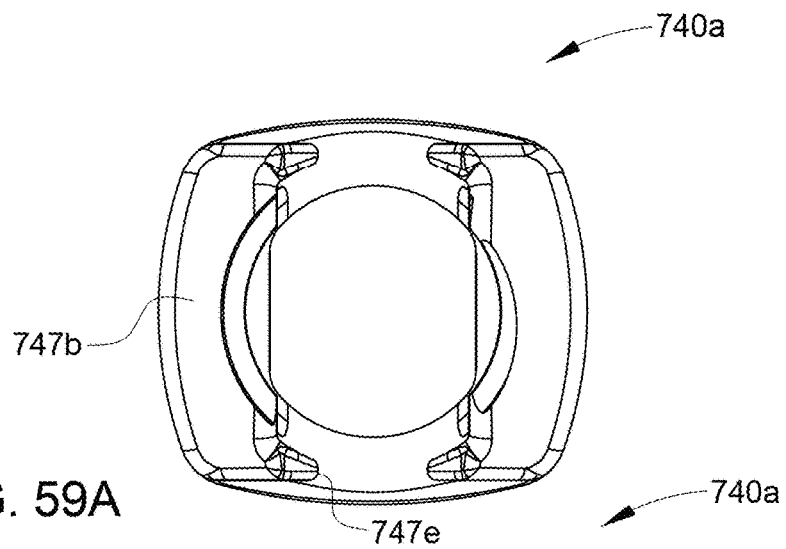
FIG. 59A is a top plan view of a component shown in FIG. 57.
Figure 59B:
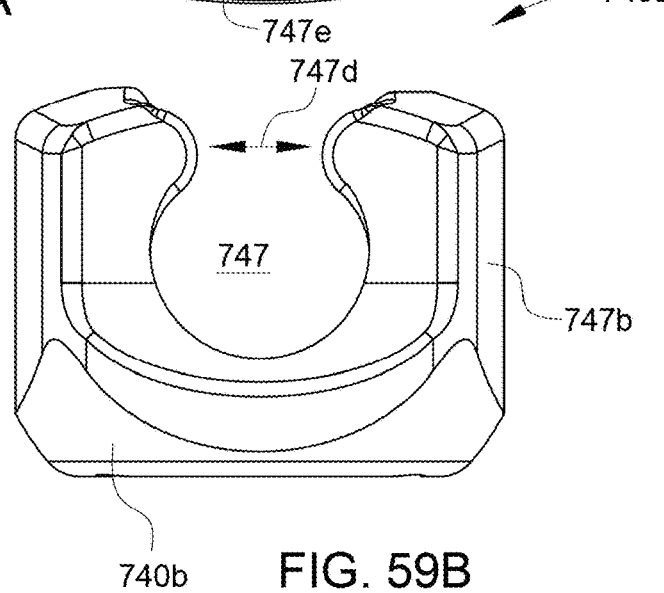
FIG. 59B is a side elevational view of the apparatus of FIG. 59A, shown orthogonally to FIG. 59A.

FIG. 59 depict another difference between head body 740a and the body 40a of anchor 20. As best seen in FIG. 59B, the arms 747b extend generally upward from base 740b, and establish a two-level tether pathway 747 therebetween. In some embodiments, the upper level tether pathway is adapted and configured for the temporary, low stress positioning of a flexible connector prior to tensioning. The lower level pathway is a preferably wider pathway adapted and configured to provide clearance relative to the frictionally-restraining corridor 757. These opposing arms 747b in some embodiments include a threaded receptacle 747c for coupling to a set screw.

Figure 59C:
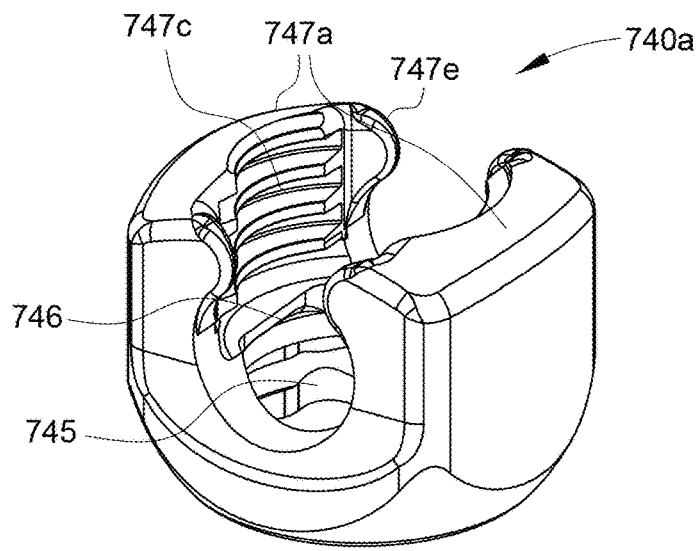
FIG. 59C is a top, side perspective view of the apparatus of FIG. 59A.

The opposing arms 747b of body 740a establish a pathway 747 of variable width. It can be seen that the pathway 747 opens with a greater width at the topmost surface 747a, and then reduces to a minimum width 747d that is established between opposing faces 747e of the arms. As best seen in FIGS. 59A and 59C, these opposing surfaces 747e are provided radially outward from the threaded portion 747c, and preferably are provided at the laterally opposite entrance and exit of pathway 747. Preferably, there are two pairs of opposing faces 747e, one at the tether pathway entrance, and a second pair at the tether pathway exit (i.e., this upper level tether pathway between faces 747e contacts the flexible connector at four discrete locations). However, yet other embodiments include only a since pair of opposing faces (i.e., two points of contact with the flexible connector). In addition, yet other embodiment contemplate a serpentine upper level of contact (i.e., such as with three points of contact; two being on one side of the tether pathway and the other point being on the other side, between the two opposing points). Still further, referencing to FIG. 59B, it can be seen that the plan view shape of the tether pathway is generally symmetrical, with each of the opposing faces 747e extending equally inward toward a centerline. However, other embodiments of the invention are not so constrained, and contemplate opposing faces of the arms that establish the minimum pathway distance 747d asymmetrically.

Figure 64:
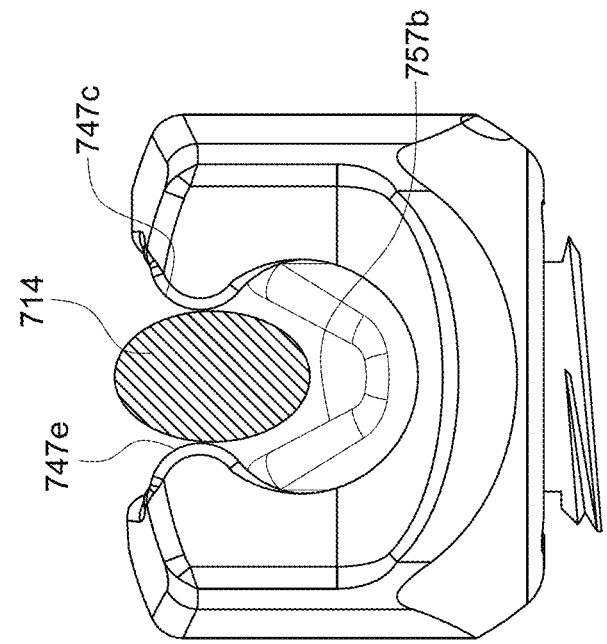
FIG. 64 is a view of the apparatus of FIG. 61 including a tether temporarily located by the head assembly.

Referring to FIG. 64, it can be seen that this minimum distance 747d and the opposing faces of the arms are adapted and configured to lightly compress therebetween a flexible connector 714. When the flexible connector is placed between these opposing surfaces, it is frictionally held in place sufficient to keep the connector coupled to the connector as the surgeon moves other parts of the flexible connector to other bone anchors. However, the compression between the opposing faces of the flexible connector is not so great as to require significant effort to temporarily affix the connector between the opposing faces.

Figure 61:
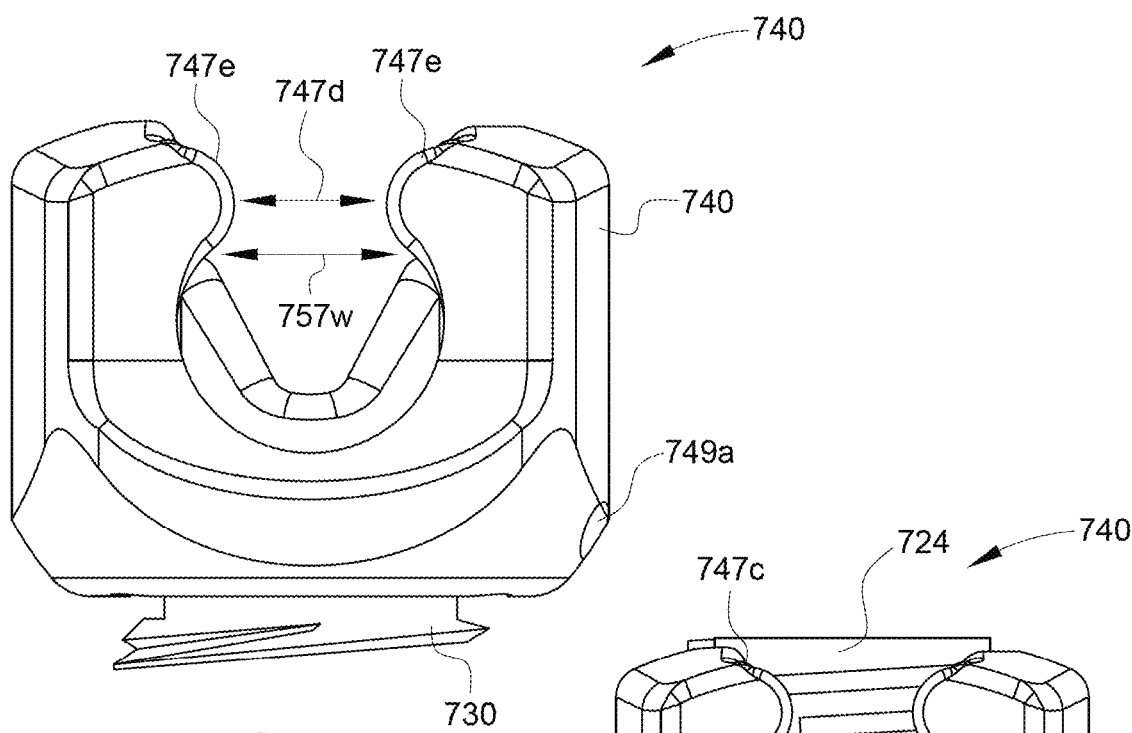
FIG. 61 is a side elevational view of a portion of the apparatus of FIG. 57.
Figure 62:
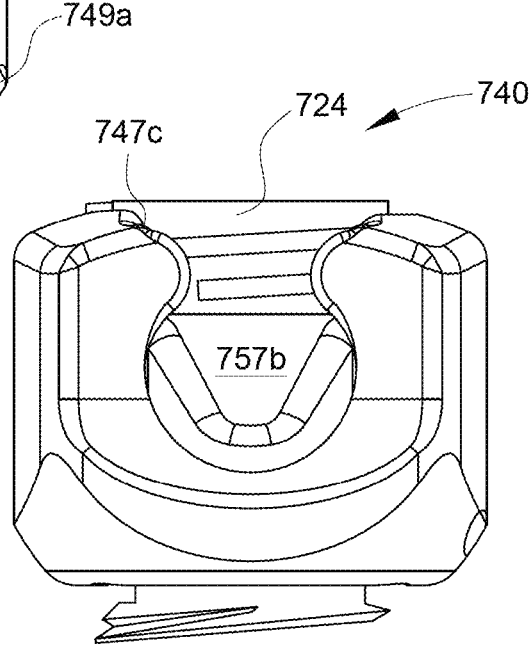
FIG. 62 is a side elevational view of a portion of the apparatus of FIG. 57.
Figure 63:
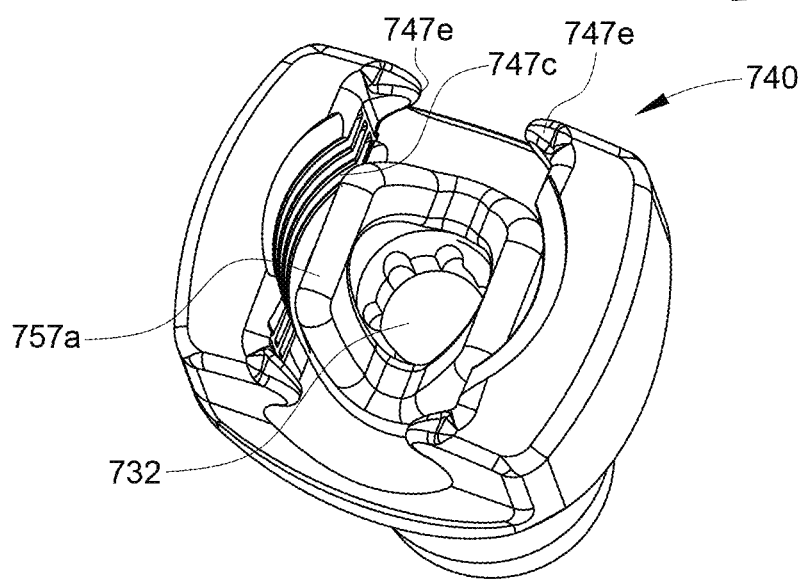
FIG. 63 is a top, side perspective view of the apparatus of FIG. 61.
Figure 65:
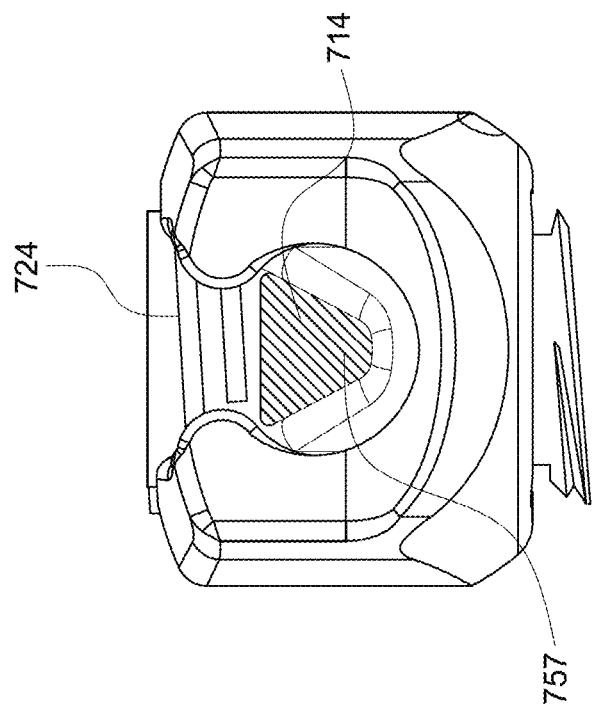
FIG. 65 is a side elevational view of the apparatus of FIG. 64, except with the set screw tightened so as to frictionally lock the tether within the corridor of the saddle member.

Referring to FIG. 61, it can be seen that this minimum distance 747d of tether pathway 747 is located above the flexible connector corridor 757 in which the flexible connector will ultimately be locked. In some embodiments, the entrance to the corridor 757 has a width 757w that is greater than the width 747d between opposing faces. Therefore, when the flexible connector is pushed into corridor 757 by the surgeon, the opposing faces assist in keeping the non-compressed flexible connector from escaping upward out of corridor 757. Referring to FIGS. 62 and 65, it can be seen that placement of the set screw 724 within the threaded receptacle of body 740 pushes the flexible connector downward past the opposing face 740e, and affixed within a corridor 757 that is roughly triangular in shape.

Figure 50A:
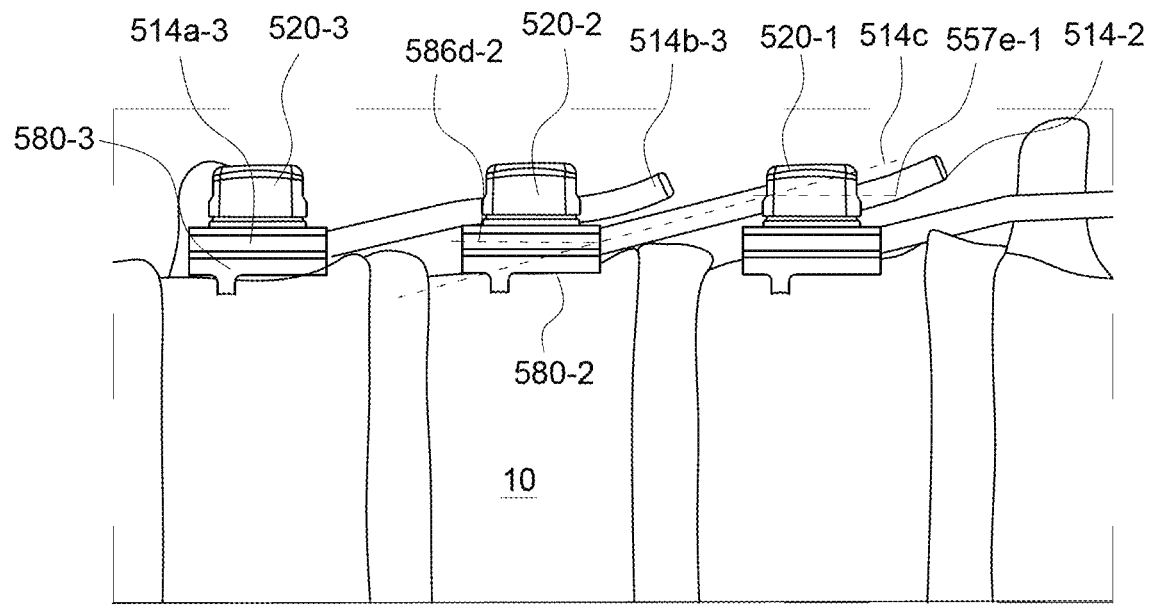
FIG. 50A is a side elevational view of a plurality of the interconnected bone anchor of FIG. 39.
Figure 50B:
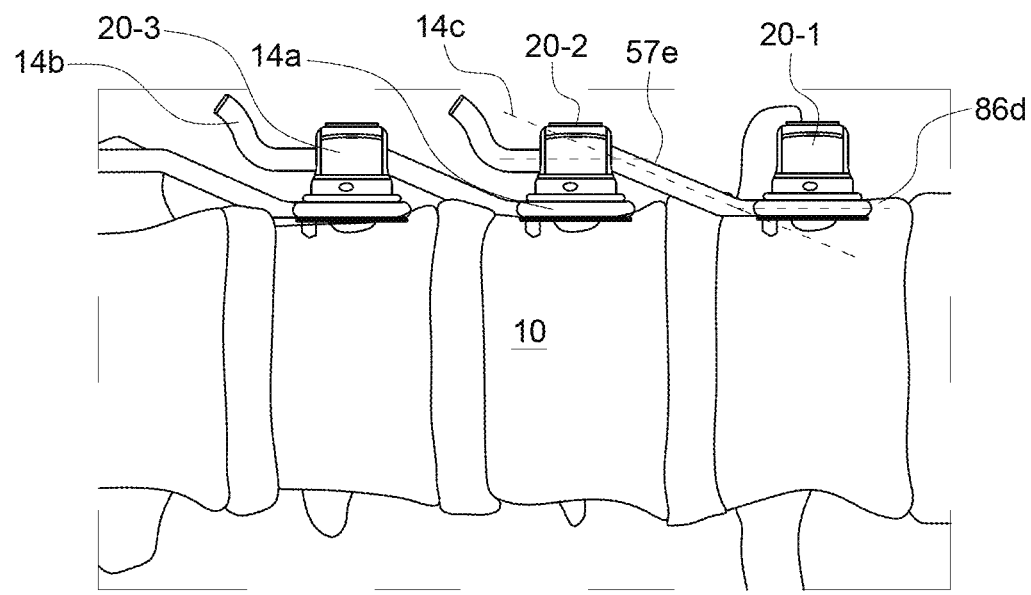
FIG. 50B is a side elevational view of a plurality of the interconnected bone anchor of FIG. 5.

FIGS. 50A and 50B depict installations of a plurality of installed anchors according to different embodiments of the present invention. A discussion and comparison of these two figures illustrate how different embodiments of the present invention can provide alternate ways of loading adjacent vertebrae corresponding to the spatial separation distance between a lower level tether pathway (such as around a staple) and a higher level tether corridor or pathway, such through the anchoring head.

FIG. 50A shows a plurality of adjacent vertebra 10 with each having fastened to it a bone anchor 520, 620, or 720. For the sake of simplicity bone anchor 520 is shown installed in each of the vertebrae, but it is understood that the description that follows applies to any of these three bone anchors.

Viewing FIG. 50A from left to right, it can be seen that a leftmost vertebra has implanted in it a bone anchor 520-3, with a flexible member 514-3 looped around the staple 580-3. The free end 514b-3 passes through and out of the tether corridor of an adjacent bone anchor 520-2. A loop of a flexible connector 514-2 couples to anchor 580-2, with the free end extending through the corridor 575-1 of the rightmost bone anchor 520-1. It is understood that the free ends shown and described in some embodiments have no function and carry no load, and therefore are candidates for removal by the surgeon.

It can be seen that tether 514-2 passes through the midway 557e-1 of the corridor of anchor 520-1. The two anchors 520-2 and 520-1 are interconnected by spatially separated pathways. FIG. 50A and FIG. 50B each represent scaled drawings according to one embodiment of the present invention, although it is understood that this scaling (and the tether angles shown) are examples, and non-limiting. It can be seen that the tensioned, interconnecting portion of flexible member 514-2 between anchors 520-2 and 520-1 follows an interconnection angle 514c from the groove of one staple to the corridor of the adjacent bone anchor.

FIG. 50B shows a construction of a plurality of bone anchors 20 in a fashion similar to that of FIG. 50A, although with the direction of the interconnections being opposite (i.e., right to left). As discussed previously, the vertical distance between the center 86d of groove 86 to the center 57e of the flexible connector corridor is a greater separation than that shown for bone anchors 520 in FIG. 50A. It is understood that the tethering angle shown in FIG. 50A maybe be helpful in those situations in which the surgeons desires to utilize an anchor having a lower overall height (i.e., distance of the top surface of the bone anchor from the bone), or those situations in which it is desired to load two adjacent vertebra with a lesser degree of rotation, a lesser degree of shear, and a higher degree of intravertebral compression. In contrast, the construction shown in FIG. 50B can be helpful in those situations in which more internal clearance is available for the fastener head (so as to provide an easier implantation), or in those situations in which it is desired to have a higher degree of intravertebral rotation, a higher degree of shear, and a lesser degree of compression.

FIG. 51 show various aspects of a bone anchor and a flexible connector adapted and configured for implantation proximate to the apex of a curved spine. The single-tailed segmental flexible connections 714 and 14 shown in FIGS. 50A and 50B can be used when the surgeon is building his construct from top-to-bottom or from bottom-to-top. However, some surgeons prefer to build their constructs from the apex (center) of the construct outwards. For an apex-out approach, the single-tailed tethers may create an inconsistent scenario from a technique perspective. On one side of the construct the tails will be pointing to the apex while on the other side of the construct the tails will be pointing to the end of the construct.

Another embodiment of the present invention pertains to a "Double-Segmental" flexible connection 814 adapted and configured for usage at the apex of the spinal curve. This tether 814 has a central loop that wraps around the staple but is now created with two tails that point to either end of the construct. When the surgeon is building an apex-out construct with this Double-Segmental tether 814, the tails of all the tethers in the construct are pointing towards their respective end of the construct.

Figure 51A:
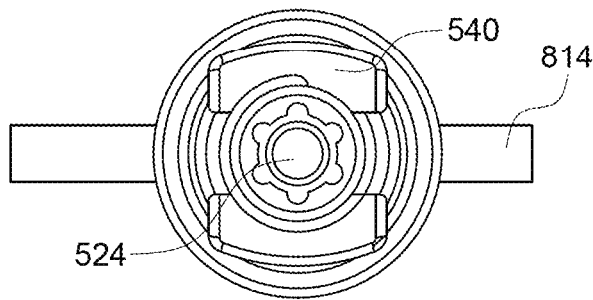
FIG. 51A is a top plan view of a bone anchor according to one embodiment of the present invention including a flexible connector according to another embodiment of the present invention.
Figure 51C:
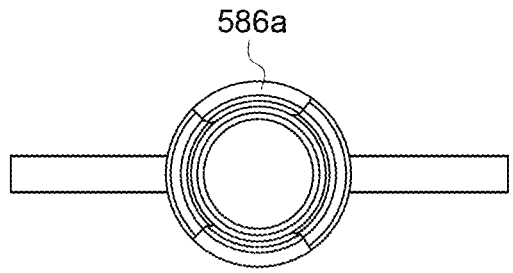
FIG. 51C is a top plan view of the apparatus of FIG. 51A, with a portion of the bone anchor removed.
Figure 51B:
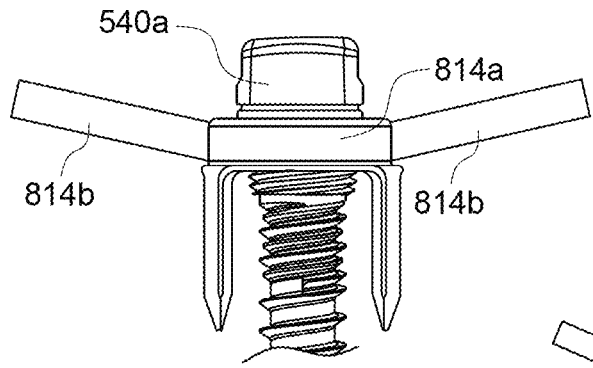
FIG. 51B is a side elevational view of the apparatus of FIG. 51A.
Figure 51D:
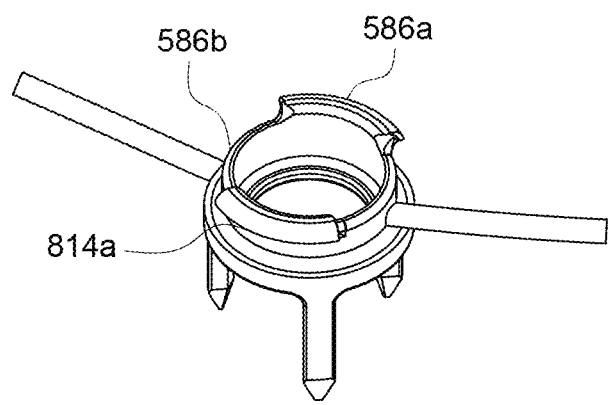
FIG. 51D is a side, top perspective view of the apparatus of FIG. 51C.
Figure 51E:
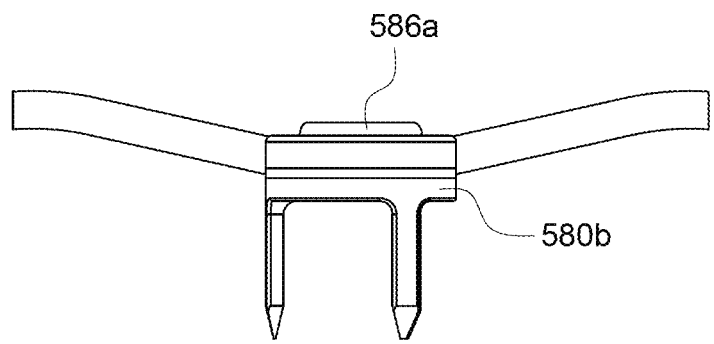
FIG. 51E is a side elevational view of the apparatus of FIG. 51C.

FIG. 51A shows a top plan view of a tethering bone anchor utilizing a double-tailed flexible connector 814 according to another embodiment of the present invention. It is understood that the depiction of connector 814 with a bone anchor 520 is by way of example only, and the double-tailed flexible connector 814 can be used with any bone anchor assembly that can couple to a loop. Referring to FIG. 51B, it can be seen that the free ends 814b extend in generally opposite directions from a flexible connector loop 814a. FIGS. 51C and 51D further show how in some embodiments it is preferable to use the flexible connector 814 with a groove that includes a relieved sector such as sector 586b in locations proximate where the free ends 814b extend from loop 814a. In this manner of incorporating relief in the groove, it can be appreciated from FIGS. 51B and 51E that in those situations in which the free ends extend at an angle to a tether corridor that is vertically displaced, that there will be less abrasion for any portion of the flexible connector 814 that moves vertically out of the groove X86.

FIG. 52 show a variety of tethering assemblies and their components according to various embodiments of the present invention.

Figure 52A:
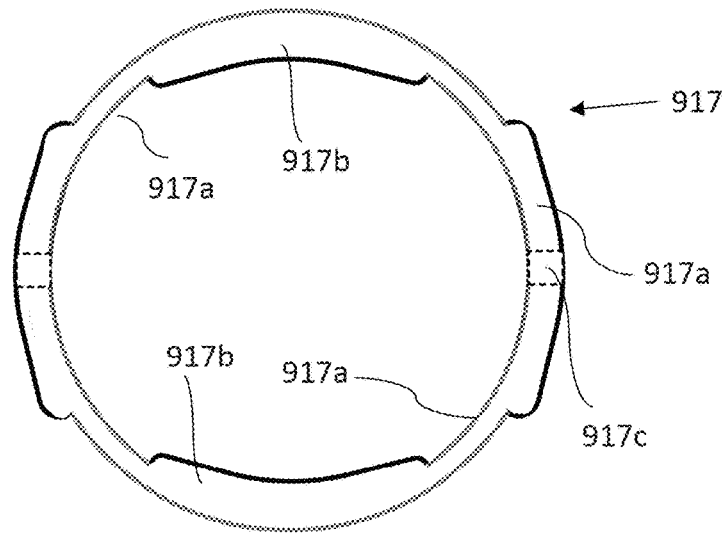
FIG. 52A is top plan view of an anchoring ring according to one embodiment of the present invention.

FIG. 52A is a top view of an anchoring ring 917 that is adapted and configured to interlock with the top of bone anchor 580 according to one embodiment of the present invention. Referring to FIG. 46A, it can be seen that the top of bone anchor (or staple) 580 includes a circumferential groove 586 having a top overhanging circumferential lip 586a that extends over two angular, oppositely located sectors of anchor 580. Between these two overhanging sectors 586a, are two lip-relieved sectors 586b that have an angular extent, and opposing locations, and placement between the overhanging sectors 586a. This arrangement can also be seen in FIG. 46B.

Referring back to FIG. 52A, anchoring ring 917 has inner and outer circumferential regions that are adapted and configured to fit over the top of a bone anchor 580 (or any other implantable anchoring member), with ring 917 having two angular sectors 917a that are sized and configured to fit over the overhanging lip portions 586a of anchor 580. The sectors 917a have larger diameter inner surfaces than the smaller diameter inner surfaces of the interfering sectors 917b. These oppositely placed interfering sectors 917b are sized and configured to fit within and under the corresponding relieved sectors 586b of an anchor 580. Comparing FIGS. 52A and 46A, it is appreciated that the image of anchor 917 as shown will fig over top of the image shown in FIG. 46A. When the anchoring ring and bone anchor 580 are so aligned, the anchoring ring 917 will pass vertically downward (i.e., into the page), and locate within tether pathway 587.

After the anchoring ring is so placed, the ring 917 can then be rotated ninety degrees for interlocking and use during implantation surgery. It is understood that with the ninety degrees of rotation, that the inner diametrical surfaces of the interfering sectors 917b will thereafter be located under oppositely located overhanging lips 586a. Likewise, the relieved sectors 917a will be aligned with the relieved sectors 586b. In the orientation thus described, and anchoring ring 917 on the bone anchor 580 (as shown in FIG. 46A) will have the two oppositely placed passages 917c located at the top and bottom of the anchor 580, as shown.

Preferably, anchoring ring 917 is fabricated from a material that generally retains its shape when tension, compression, or shear loads along any axis are applied to it. Preferably, the anchoring ring is elastic, such that compressive, tensile, or shear forces placed on the ring cause the ring to deflect elastically, such that the ring returns to its shape after the load is removed (it being understood that this elastic behavior is only for loads within certain limits). In some embodiments, the ring is fabricated from a material such as titanium, stainless steel, or any other biocompatible material.

Figure 52B:
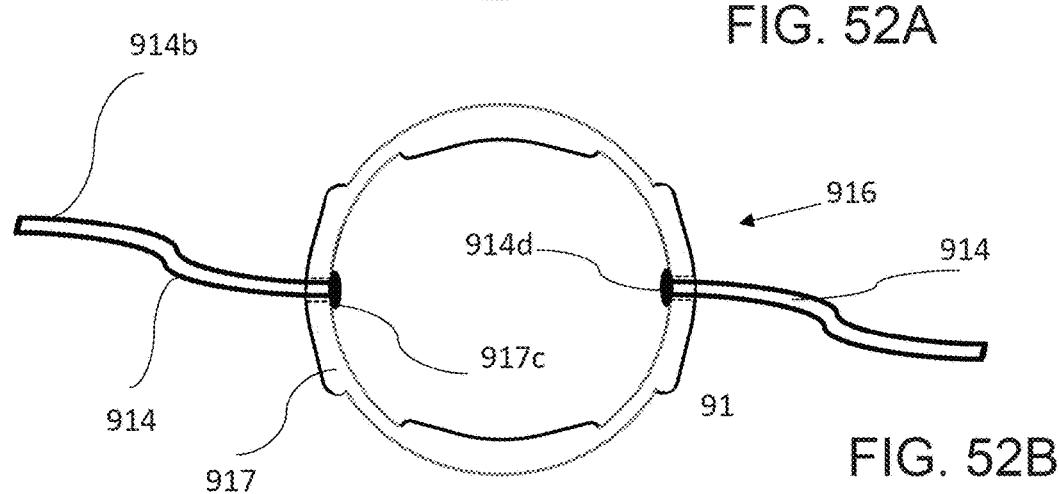
FIG. 52B is a top view of a tethering assembly according to one embodiment of the present invention.

FIG. 52B shows a tethering assembly 916 according to another embodiment of the present invention. Assembly 916 includes an anchoring ring 917, as well as, in some embodiments, a pair of flexible connector segments 914. As shown in FIG. 52B, each connector segment 914 includes a captured end 914d that is located proximate to an inner surface of relieved sector 917a. The remainder of the flexible connector segment 914 extends through passageway 917c. The free end 914b of the segment, when tensioned, extends a predetermined distance away from 917. As shown in FIG. 52B, the captured end 914d can be of any type, including a separate button or end connector coupled to the end of the segment 914, a knotted or doubled over portion of the connector 914 itself, or any other configuration suitable for retaining connector 914 on ring 917 when a tension load is applied to segment 914.

Figure 52C:
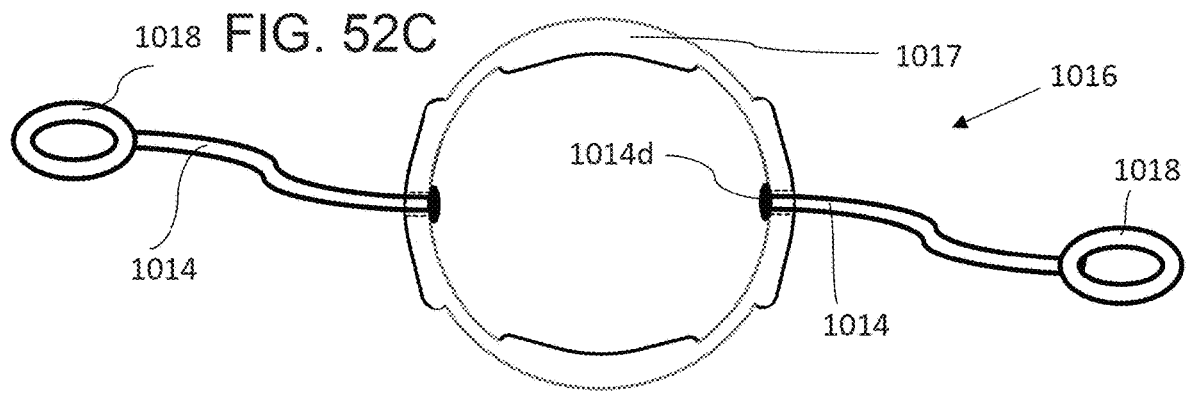
FIG. 52C is a top plan view of a tethering assembly according to another embodiment of the present invention.

FIG. 52C shows yet another tethering assembly 1016 according to another embodiment of the present invention. Assembly 1016 is generally the same as that shown and described for assembly 916, except that at least one of the free ends of the tether segments includes an end connector 1018, shown as an elliptical ring. This end connector is used during the implantation surgery to apply the tension load to the connector segment 1014, prior to segment 1014 being frictionally restrained in the head assembly of a bone anchor assembly. The configuration of end connector 1018 can be of any type. Preferably, the end connector is adapted and configured for temporary interconnection to an instrument that the surgeon uses to apply the tensile load, with the loop 1018 being removed after implantation. However, in yet other embodiments this ring section 1018 could also be attached to an adjacent bone anchor and remain a part of the implantation.

FIGS. 52D and 52F depict potions of anchoring rings according to yet other embodiments of the present invention. It is understood that all of the features useful in adapting anchoring rings 1117 or 1317 to a bone anchor such as staple 580 are not shown or described in these figures.

FIG. 52D shows certain aspects of a 2-part anchoring ring 1117. When the two rings are assembled, the assembly has 2 split or separated ends 1117*d* on either side of the assembled ring. Further, each split apart end includes an interlocking feature 1117*e* that is adapted and configured to connect and provide a carry through of tensile loads from one ring half to the other ring half. Anchoring ring 1117 further includes a pair of opposing through channels 1117*c* for passage therethrough of a segment of flexible connector (not shown).

FIG. 52F shows a ring 1317 according to another embodiment of the present invention. Ring 1317 is similar to rings used in the retaining of two components together. Ring 1317 includes a single split end 1317*d*, with a pair of through apertures on either side of the split end. An instrument (not shown) can be inserted into each of the two holes, and used to spread open the inner diameter of the ring, thus enabling it to fit over the top lip 586*a* of a bone anchor 580. On the ring has been expanded, placed in the groove 586, and then released back to its normal configuration, either of the tool holes 1317*f* can be used for connection to segment of flexible connector as previously described with regards to assembly 916. A second aperture 1317*c* is located on the ring generally opposite of the split end 1317*d*.

FIG. 52E shows one embodiment of a tethering assembly 1216. Assembly 1216 includes a central anchoring ring 1217, with a loop 1214*a* from a segment of flexible connector 1214 wrapped around the outer circumference of ring 1217.

FIG. 53A shows a collection of components used to construct a tethering assembly 1416. FIG. 53A shows a flexible connector 1414 that includes a loop 1414*a* on one end, and a free end 1414*b* separated from the loop by a distance that is preferably greater than the distance between adjacent implanted bone anchors X20. Also shown is a ring shape end connector 1414*a*, and an anchoring ring 1417.

FIG. 53B shows the assembly of the three components into a tethering assembly 1416. The loop 1414*a* is placed around the outer circumference of anchoring ring 1417. The end connector 1418 is attached to the free end 1414*b*, such that the end connector can be used to place the midsection of segment 1414 in tension. Further, the interconnection of segment 1414 and end connector 1418 is adapted and configured such that the end connector 1418 can be removed after a state of tension has been applied, without any damage to the tensile capabilities of segment 1414.

FIG. 53C shows and assembly of adjacent anchors 520. An anchoring assembly 1416-2 coupled within groove 586-2. The segment 1414-2 of flexible connector has been placed within the corridor 575-1 of adjacent bone anchor 520-1. The implantation as shown is suitable for the surgeon to place tension between the two anchors 520-1 and 520-2. By using an instrument to pull on end connector 1418-2, the surgeon places this segment in tension, and while doing so tightens the set screw 524-1. Once the state of tension has been achieved, the end connector and remaining free end 1414*b*-2 can be cut with an instrument, and removed from the implantation region.

Figure 53D:
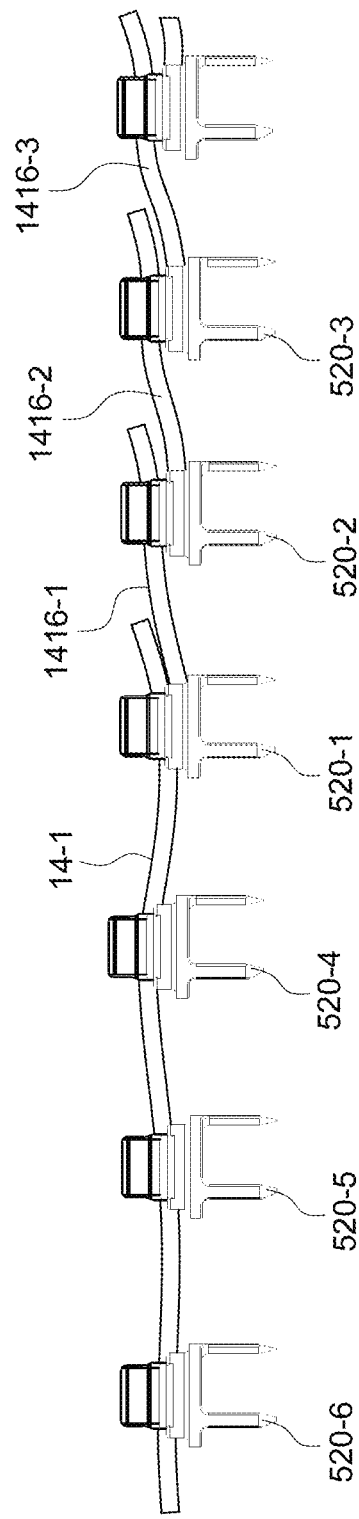
FIG. 53D is a side elevational CAD representation of a plurality of interconnected, tethered bone anchors according to one embodiment of the present invention.
Figure 53E:
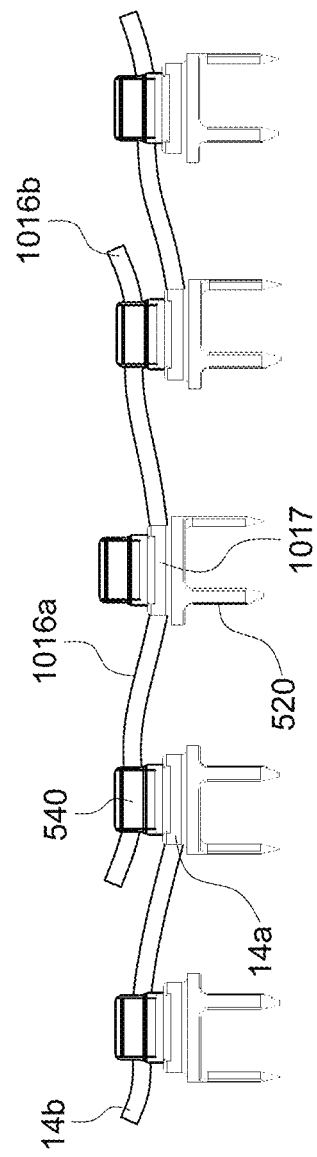
FIG. 53E is a side elevational CAD representation of a plurality of interconnected, tethered bone anchors according to another embodiment of the present invention.

FIGS. 53D and 53E show various arrangements of implantations as discussed previously herein. FIG. 53D shows on the left hand side of the figure a plurality of bone anchors 520-1, 520-4, 520-5, and 520-6 that are all interconnected with a continuous cord 14 through the corresponding tether corridors 575. In some embodiments, this continuous cord is frictionally restrained by set screws in each of the different bone anchors, although yet other embodiments of the present invention contemplate having one or more bone anchors (such as 520-5) in which the set screw has not been tightened (or is not present), such that the tether simply passes through anchor 520-5 and establishes tension between anchors 520-6 and 520-4.

On the right side of FIG. 53D are a plurality of bone anchors 520-1, 520-2 and 520-3 that are each interconnected by a tethering assembly such as assembly 1416. In each of these, the looping end of assembly 1416 is coupled to a lower pathway 587-1, while the segment free end passes through the corridor 575-2 of the adjacent bone anchor.

FIG. 53E shows the use of the connector assembly 1016 or 814 as previously discussed. This anchoring assembly 1016 or 814 is used with the anchor 520 placed proximate to the apex of the spinal curvature. The free ends extend outward in either direction to the adjacent bone anchors.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A bone anchor for a flexible connector, comprising:
   a head including a top including a threaded receptacle, an internal pocket, and a laterally extending pathway open to the top and adapted and configured for passage therethrough of a flexible connector;
   a member including a pedestal received within the pocket of said head and a pair of arms extending within the pathway of said head, said arms having an open corridor therebetween for passage of a flexible connector, at least one of said arms including a first abutting surface;
   a set screw having threads adapted and configured to threadably couple to the threaded receptacle of said head, said set screw having a bottom and a second abutting surface; and
   a base including an aperture and plurality of bone penetrating projections, and a bone fastener having a driving portion, a threaded portion adapted and configured to fasten to the bone, and an intermediate portion between the driving and threaded portion and receivable within the aperture, the intermediate portion adapted and configured to compress the base against a bone, wherein tightening of said set screw to said head brings the first and second abutting surfaces into contact, and the bottom of said set screw and said arms establish a fixed cross sectional area to the corridor, and wherein the intermediate portion of said bone fastener has a spherical outer surface and the aperture has an inner conical surface, the conical surface including a portion narrower than the spherical outer surface.

2. The bone anchor of claim 1 wherein the base has a periphery and the periphery includes a groove.

3. A bone anchor for a flexible connector, comprising:
a bone fastener having a top, a threaded portion adapted and configured to fasten to a bone, a longitudinal axis, and a rounded exterior surface intermediate of the top and the threaded portion;
a base including an aperture for receiving therein said bone fastener, the interior walls surrounding the aperture including a conically-shaped portion; a pocket surrounding the aperture, a circumferential groove adapted and configured for receiving a flexible connector; and at least one bone penetrating projection;
a head having a bottom adapted and configured to be received within the pocket, a top including a threaded receptacle, and an interior;
a member releasably coupled to the interior of said head, said member having a corridor for passage therethrough of a flexible connector; and
a set screw having threads adapted and configured to threadably couple to the threaded receptacle of said head;

wherein assembly of said bone fastener, said base, said head, and said member and subsequent tightening of said set screw within the threaded receptacle brings contact of the rounded exterior surface within the conically shaped portion, the contact being distal to the circumferential groove.

4. The bone anchor of claim 3 wherein said base is pivotal relative to said bone fastener in two orthogonal directions before said set screw is tightened in the threaded receptacle.

5. The bone anchor of claim 3 wherein tightening of said set screw within the threaded receptacle compresses said member between said bone fastener and said head.

6. The bone anchor of claim 3 wherein said head is rotatable within the pocket.

7. The bone anchor of claim 3 wherein said head includes a pathway between the top and the bottom, the pathway being adapted and configured for passage therethrough of a flexible connector.

* * * * *